(12) United States Patent
Freestone et al.

(10) Patent No.: US 11,844,903 B2
(45) Date of Patent: Dec. 19, 2023

(54) HEADGEAR ASSEMBLY

(71) Applicant: Fisher & Paykel Healthcare Limited, Auckland (NZ)

(72) Inventors: Paul Mathew Freestone, Auckland (NZ); Melissa Catherine Bornholdt, Auckland (NZ); Matthew Roger Stephenson, Auckland (NZ); Jake Baker Hocking, Auckland (NZ); Bruce Michael Walls, Auckland (NZ); Chris Onin Limpin Hipolito, Auckland (NZ); Jonathan Tong Lok Sng, Auckland (AU); Abby Rebecca Farrow, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 481 days.

(21) Appl. No.: 15/746,240

(22) PCT Filed: Jul. 22, 2016

(86) PCT No.: PCT/IB2016/054365
§ 371 (c)(1),
(2) Date: Jan. 19, 2018

(87) PCT Pub. No.: WO2017/017573
PCT Pub. Date: Feb. 2, 2017

(65) Prior Publication Data
US 2018/0207385 A1    Jul. 26, 2018

Related U.S. Application Data

(60) Provisional application No. 62/364,247, filed on Jul. 19, 2016, provisional application No. 62/196,730, filed on Jul. 24, 2015.

(51) Int. Cl.
*A61M 16/00* (2006.01)
*A61M 16/06* (2006.01)
*A61M 16/10* (2006.01)

(52) U.S. Cl.
CPC .... *A61M 16/0683* (2013.01); *A61M 16/0605* (2014.02); *A61M 16/0066* (2013.01);
(Continued)

(58) Field of Classification Search
CPC .............. A61M 16/06; A61M 16/0683; A61M 16/0605
See application file for complete search history.

(56) References Cited

U.S. PATENT DOCUMENTS 5,368,024 A     11/1994  Jones
7,296,575 B1 *  11/2007  Radney ................. A61M 16/06
                                                            128/207.11
(Continued)

FOREIGN PATENT DOCUMENTS

WO     WO 2010/066004         6/2010
WO     WO-2011077254 A2 *    6/2011  ............ A61M 16/00
(Continued)

OTHER PUBLICATIONS

Extended European Search Report, European Patent Office, Application No. PCT/IB2016/054365, dated Feb. 26, 2019, in 7 pages.
(Continued)

*Primary Examiner* — Samchuan C Yao
*Assistant Examiner* — Sarah B Lederer
(74) *Attorney, Agent, or Firm* — Knobbe, Martens, Olson & Bear, LLP

(57) ABSTRACT

A headgear assembly for retaining a respiratory mask on a user's face includes arrangements or components that allow for variation in a size of the headgear assembly. In some configurations, the headgear assembly includes one or more
(Continued)

hubs, each of which are configured to connect a top and rear strap together. The size of the headgear assembly can be determined by the size or configuration of the hub. In other configurations, the headgear assembly comprises one or more spacer elements within one or more straps of the headgear. The size of the headgear assembly can be determined by the size of the spacer element or a relative position between the strap and the spacer element.

14 Claims, 46 Drawing Sheets

(52) U.S. Cl.
CPC ..... *A61M 16/109* (2014.02); *A61M 2205/583* (2013.01); *A61M 2209/06* (2013.01); *A61M 2230/63* (2013.01)

(56) References Cited

U.S. PATENT DOCUMENTS

| | | | |
|---|---|---|---|
| 8,479,736 B2 | 7/2013 | Ging et al. | |
| 8,517,023 B2 | 8/2013 | Henry | |
| 2003/0145859 A1* | 8/2003 | Bohn | A61M 16/0616 128/206.28 |
| 2004/0133604 A1* | 7/2004 | Lordo | G16H 70/00 |
| 2004/0211428 A1* | 10/2004 | Jones, Jr. | A61M 16/0605 128/206.27 |
| 2007/0209663 A1* | 9/2007 | Marque | A61M 16/0616 128/207.11 |
| 2008/0178875 A1* | 7/2008 | Henry | A61M 16/0057 128/201.22 |
| 2009/0107508 A1* | 4/2009 | Brambilla | A61M 16/0644 128/207.11 |
| 2010/0000544 A1* | 1/2010 | Blaszczykiewicz | A61M 16/0683 428/221 |
| 2011/0197893 A1* | 8/2011 | Ziv | A61M 16/0633 128/207.13 |
| 2012/0190998 A1 | 7/2012 | Armitstead et al. | |
| 2012/0222680 A1* | 9/2012 | Eves | A61M 16/0875 128/206.24 |
| 2014/0000619 A1 | 1/2014 | Berthon-Jones et al. | |
| 2014/0261440 A1* | 9/2014 | Chodkowski | A61M 16/0627 128/206.24 |
| 2015/0007822 A1 | 1/2015 | Berthon-Jones et al. | |
| 2015/0136133 A1 | 5/2015 | Berthon-Jones | |

FOREIGN PATENT DOCUMENTS

| | | |
|---|---|---|
| WO | WO 2014/024086 A1 | 2/2014 |
| WO | WO 2014/175753 | 10/2014 |

OTHER PUBLICATIONS

European Patent Office, Examination Report, Application No. 16 829 929.5-1122, dated Nov. 20, 2019, in 5 pages.
Australian Government, Examination Report No. 1, Application No. 2016298653, dated Apr. 8, 2020, in 4 pages.
International Search Report, Application No. PCT/IB2016/054365, dated Oct. 5, 2016, in 7 pages.
European Patent Office, Examination Report, Application No. 16829929.5-1122, dated Oct. 8, 2020, in 6 pages.

\* cited by examiner

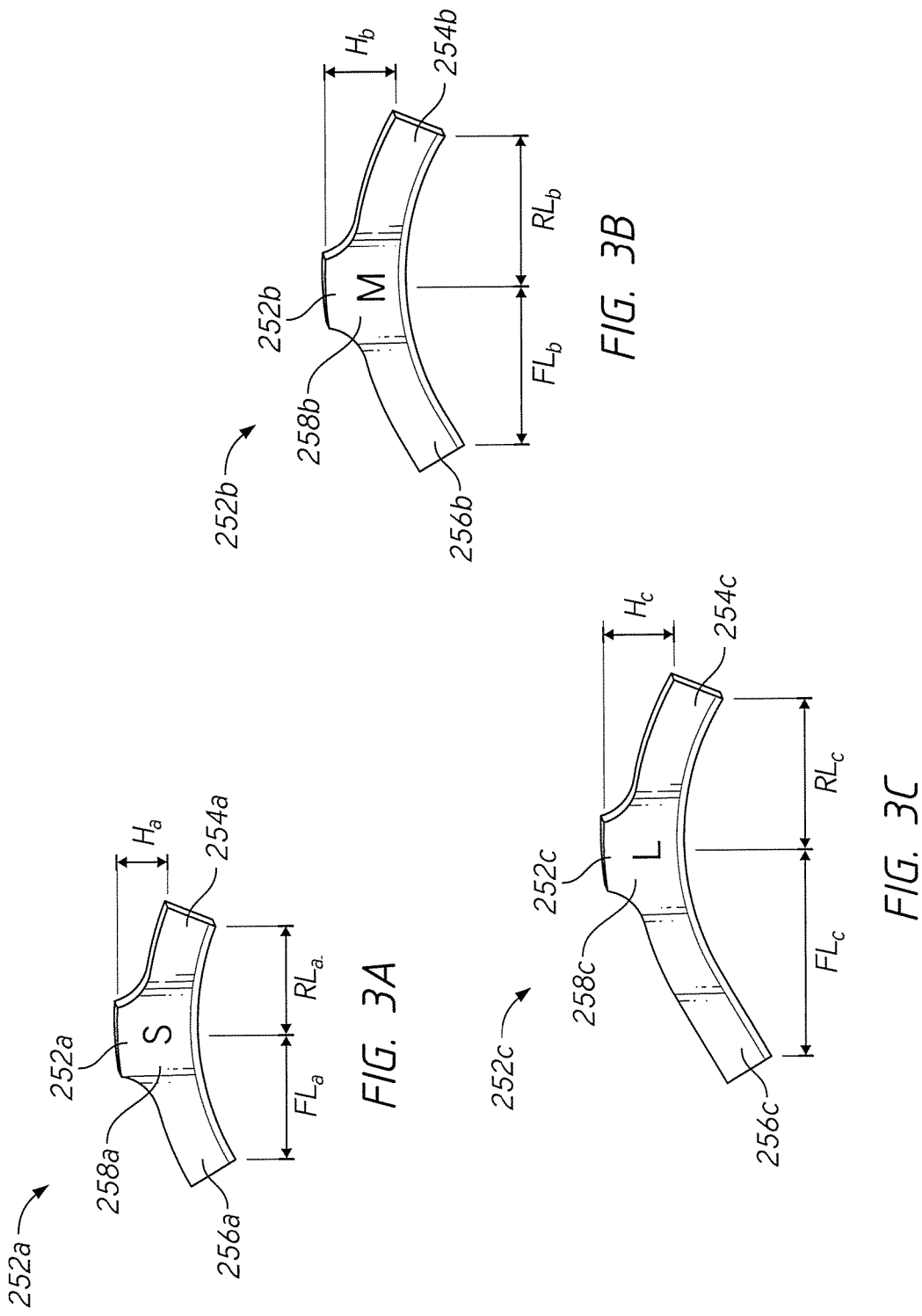

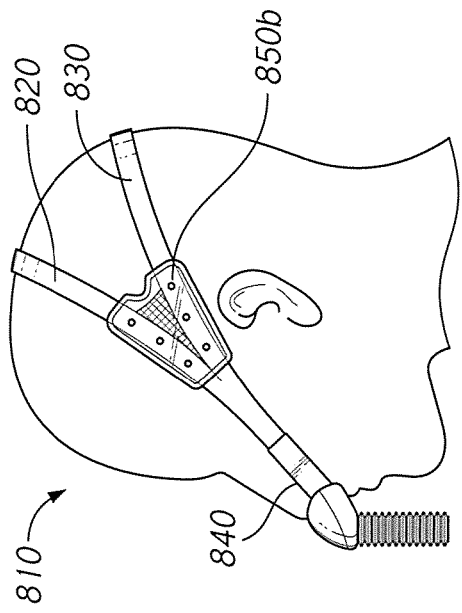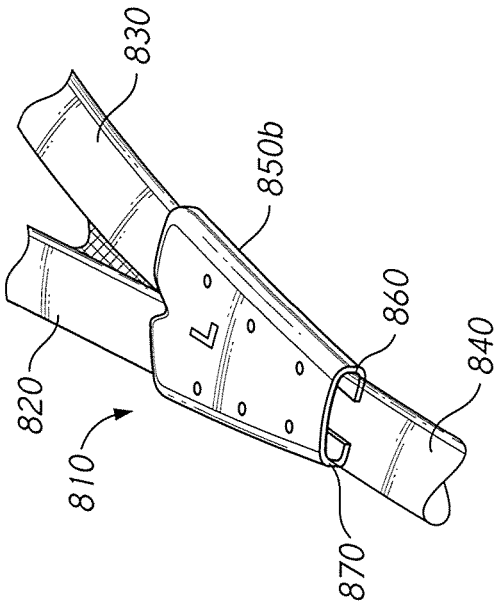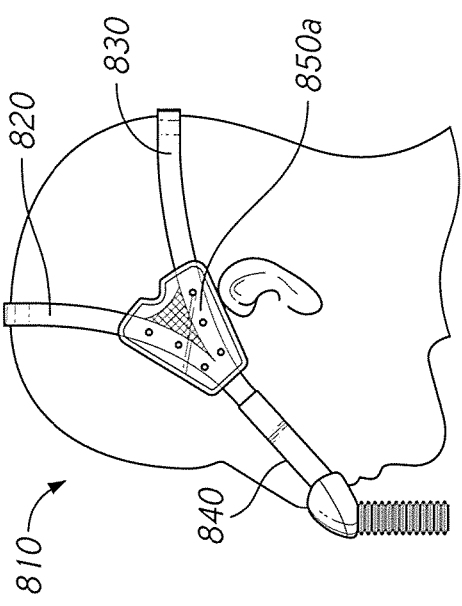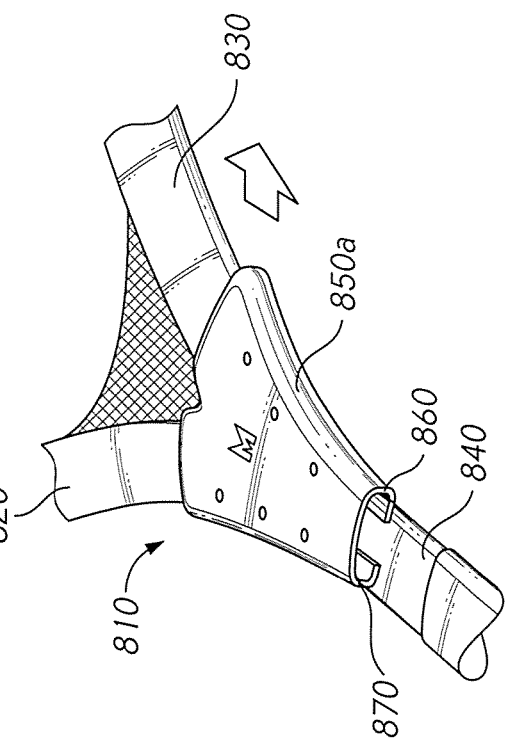

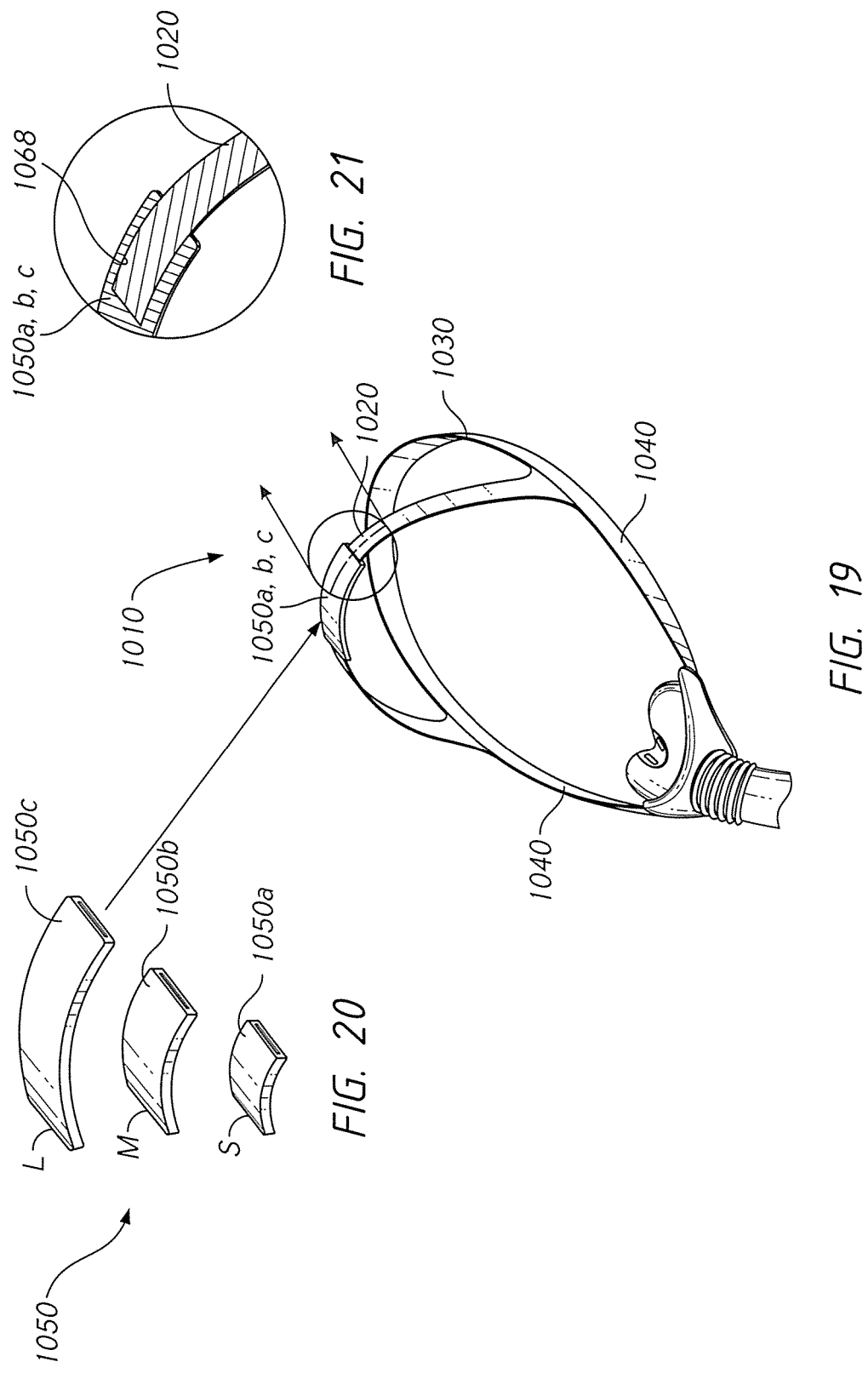

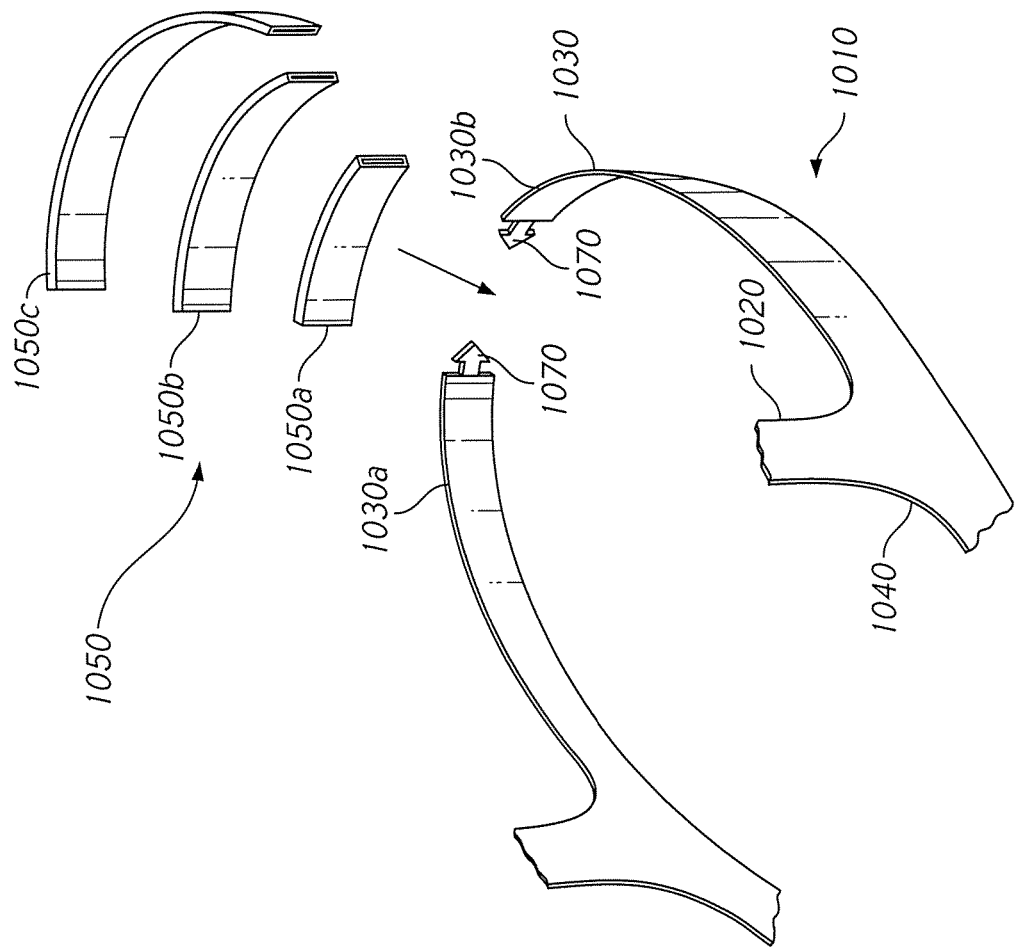

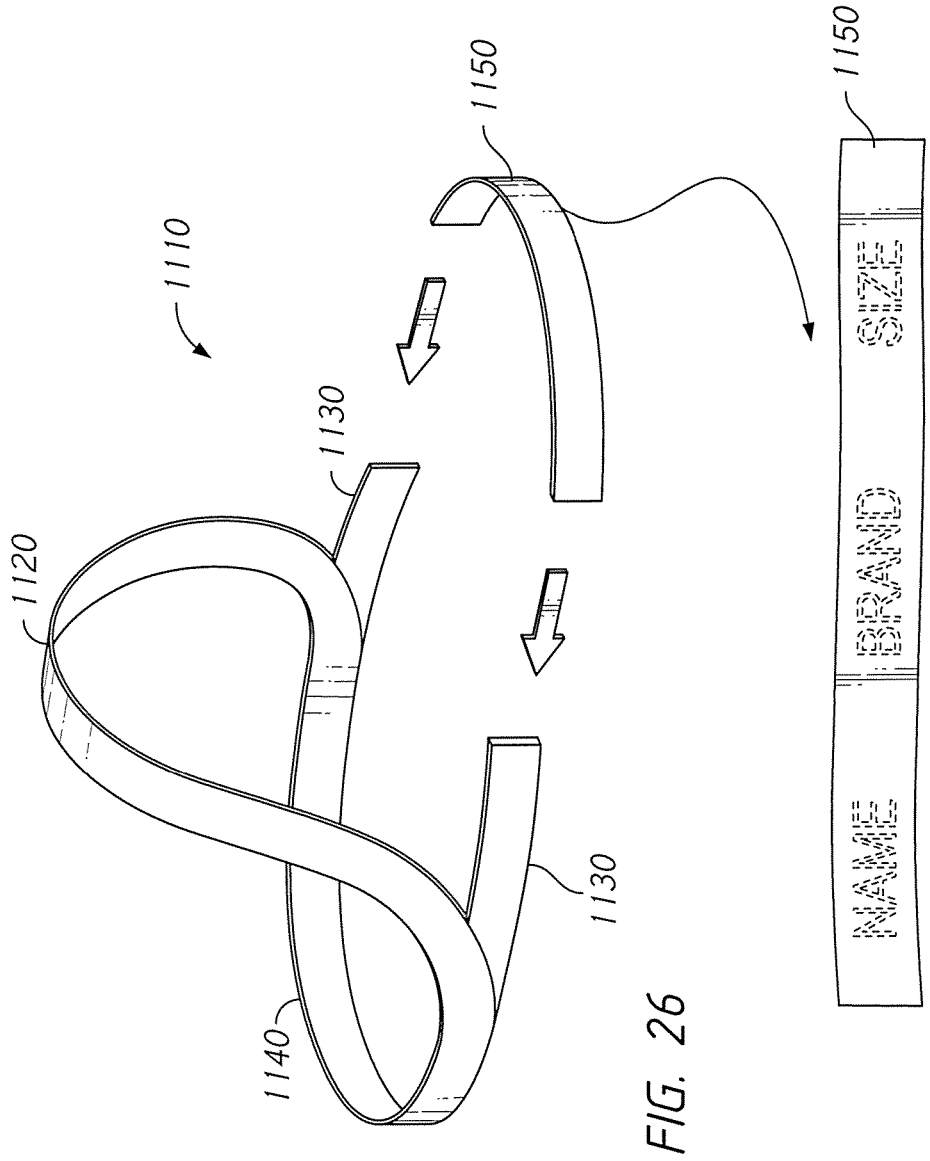

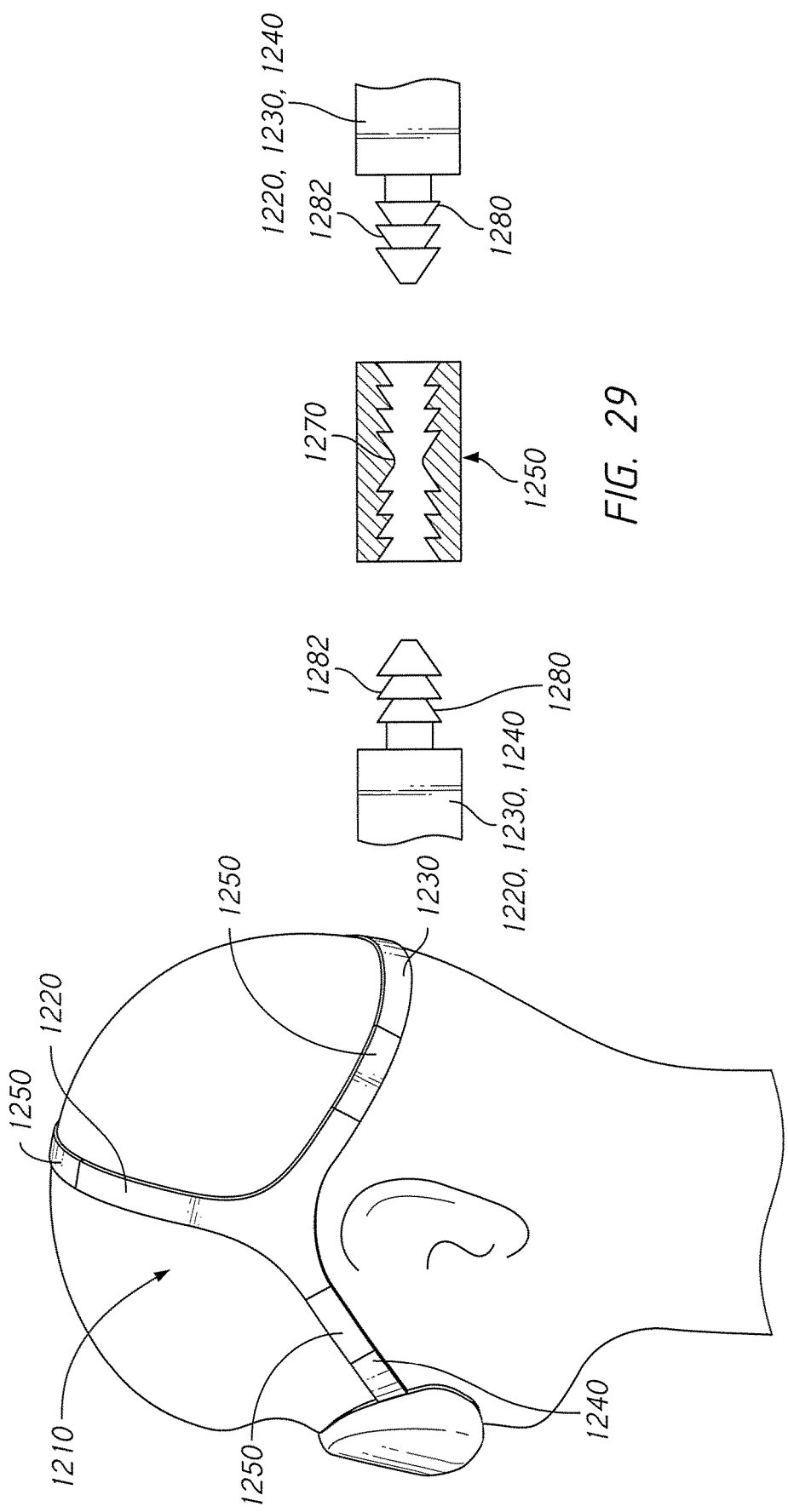

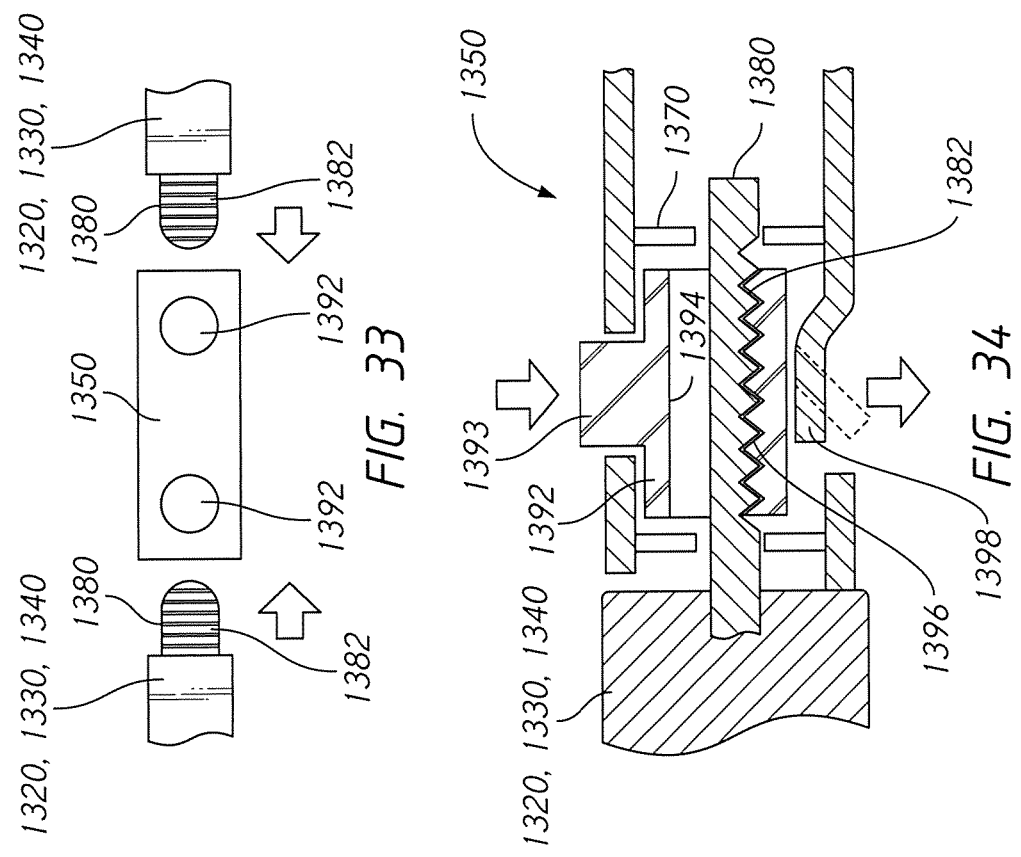
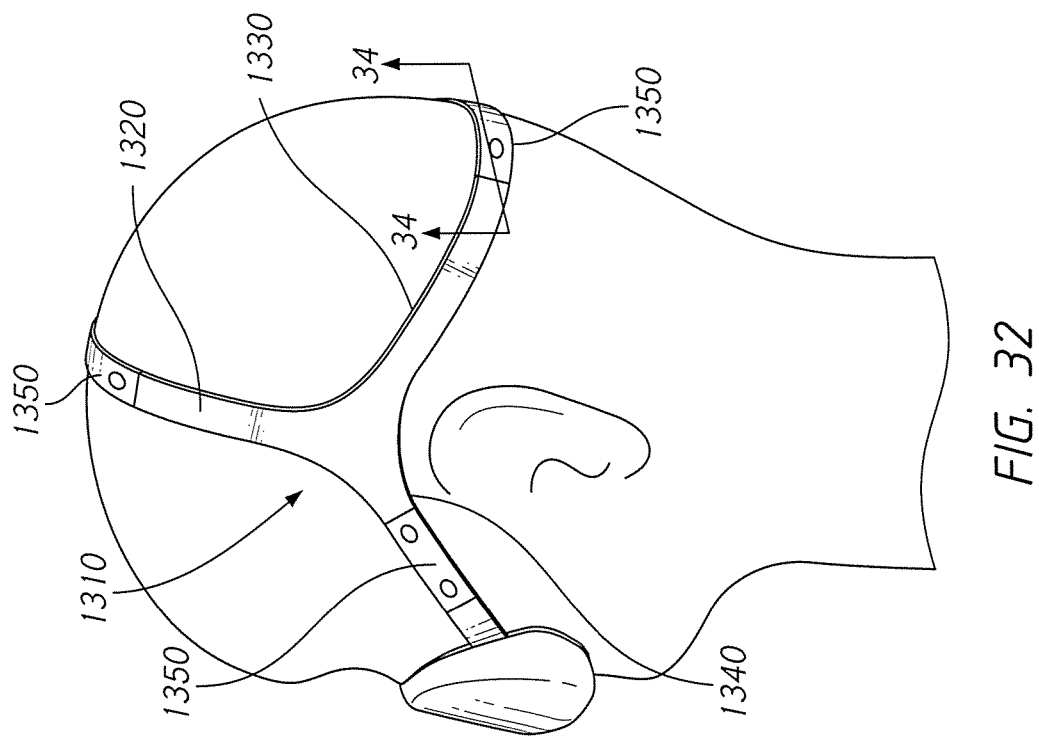

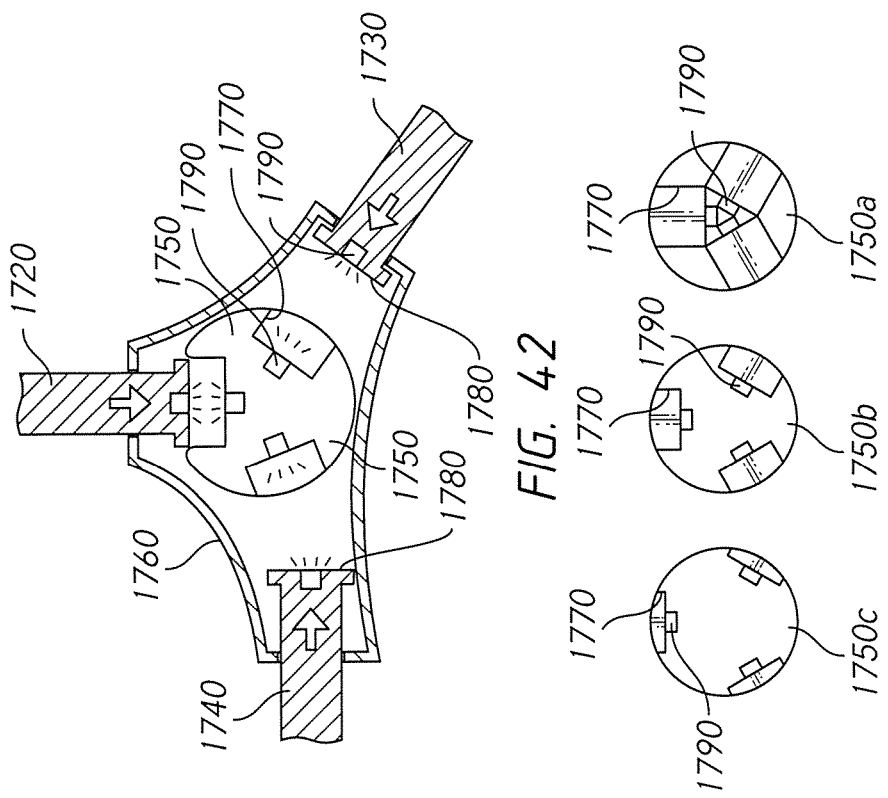
FIG. 42
FIG. 43
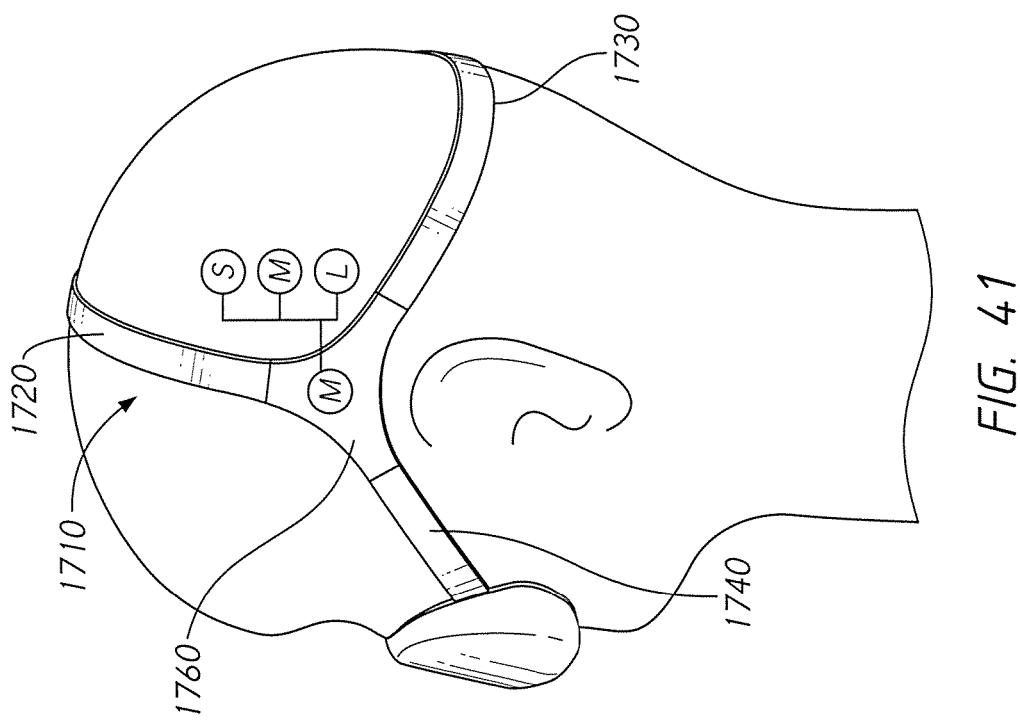
FIG. 41

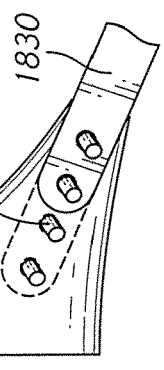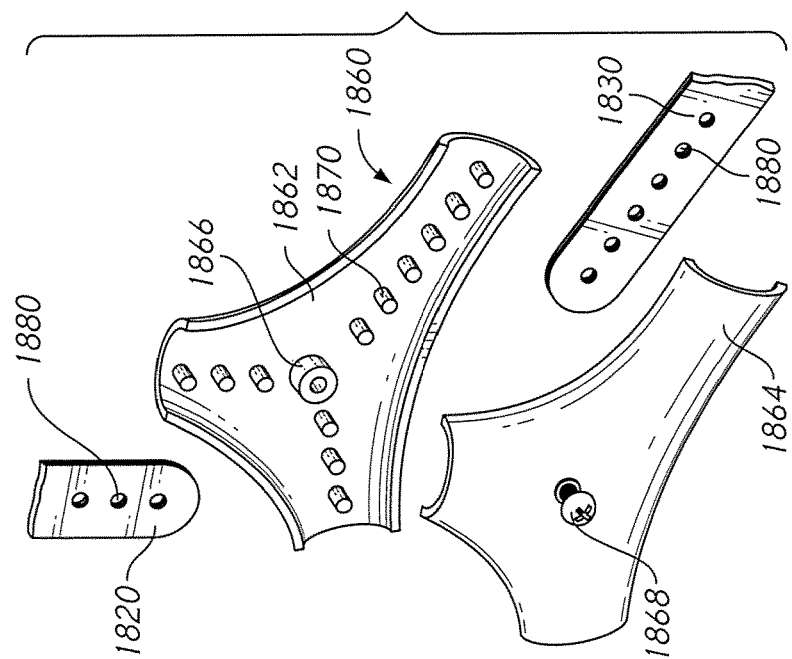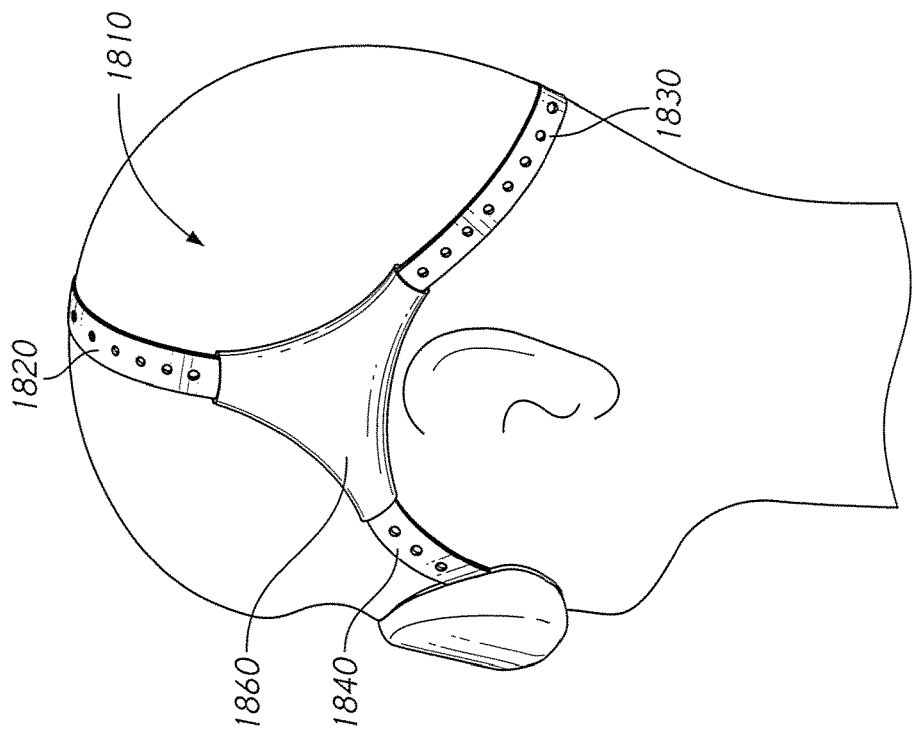

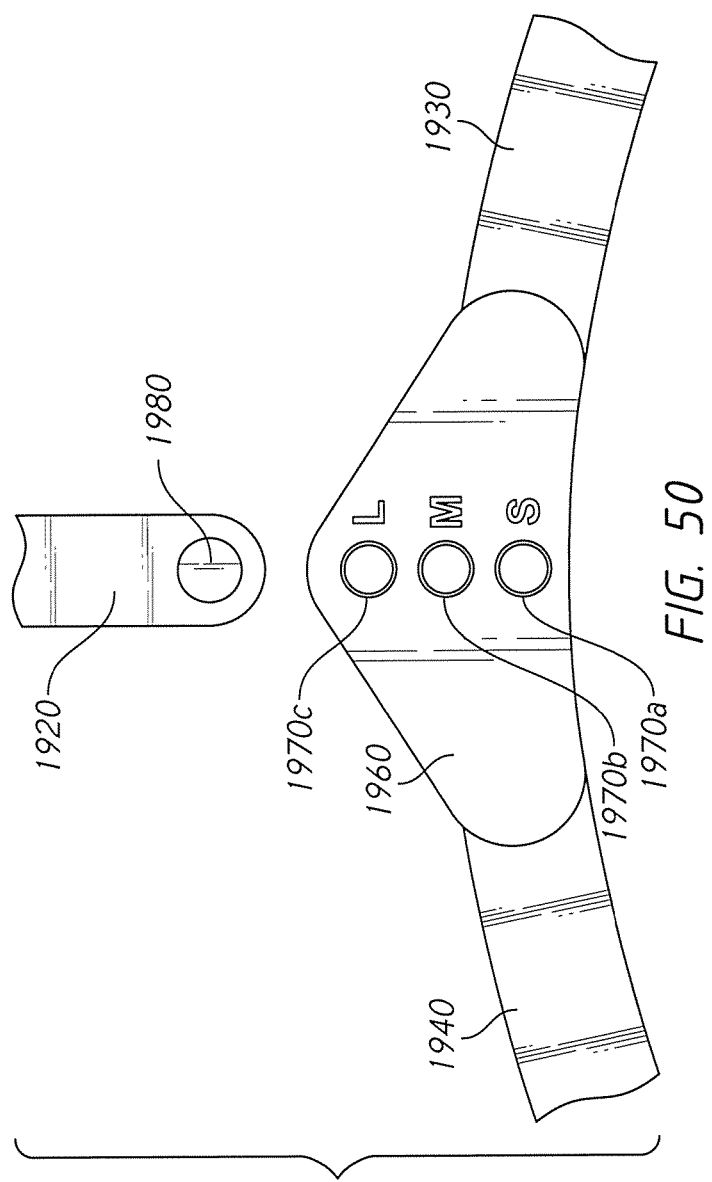
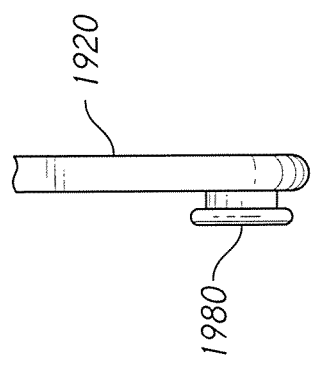

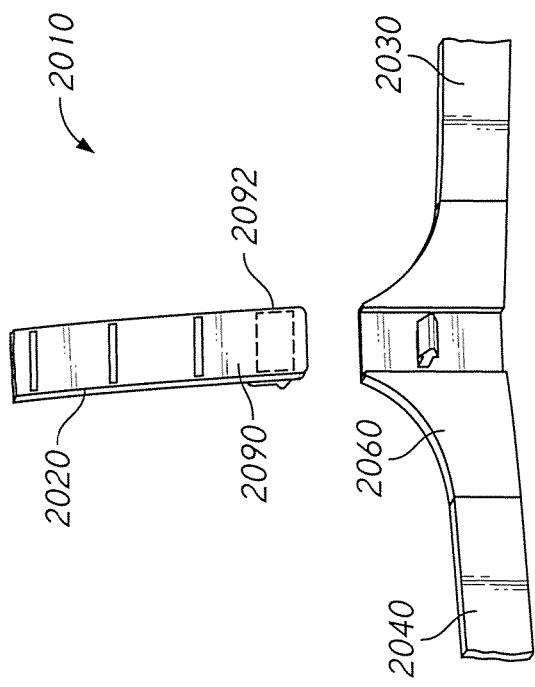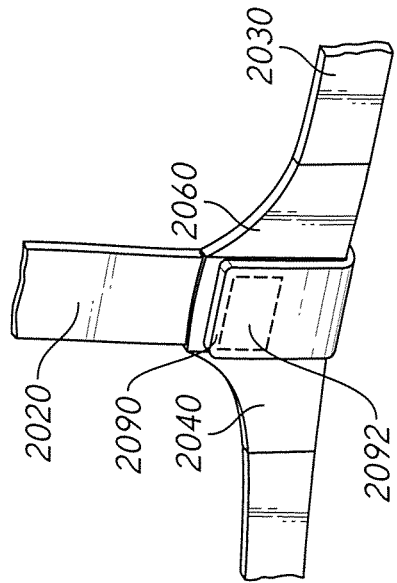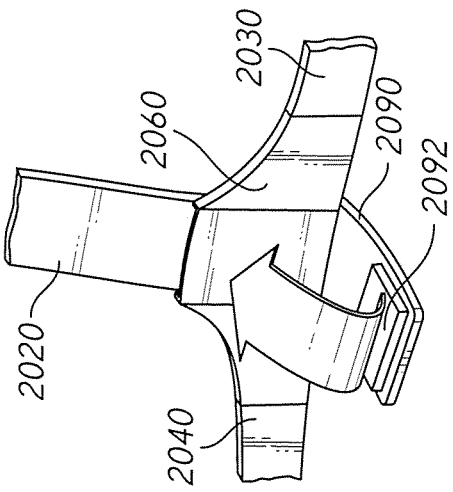
FIG. 53
FIG. 55
FIG. 54

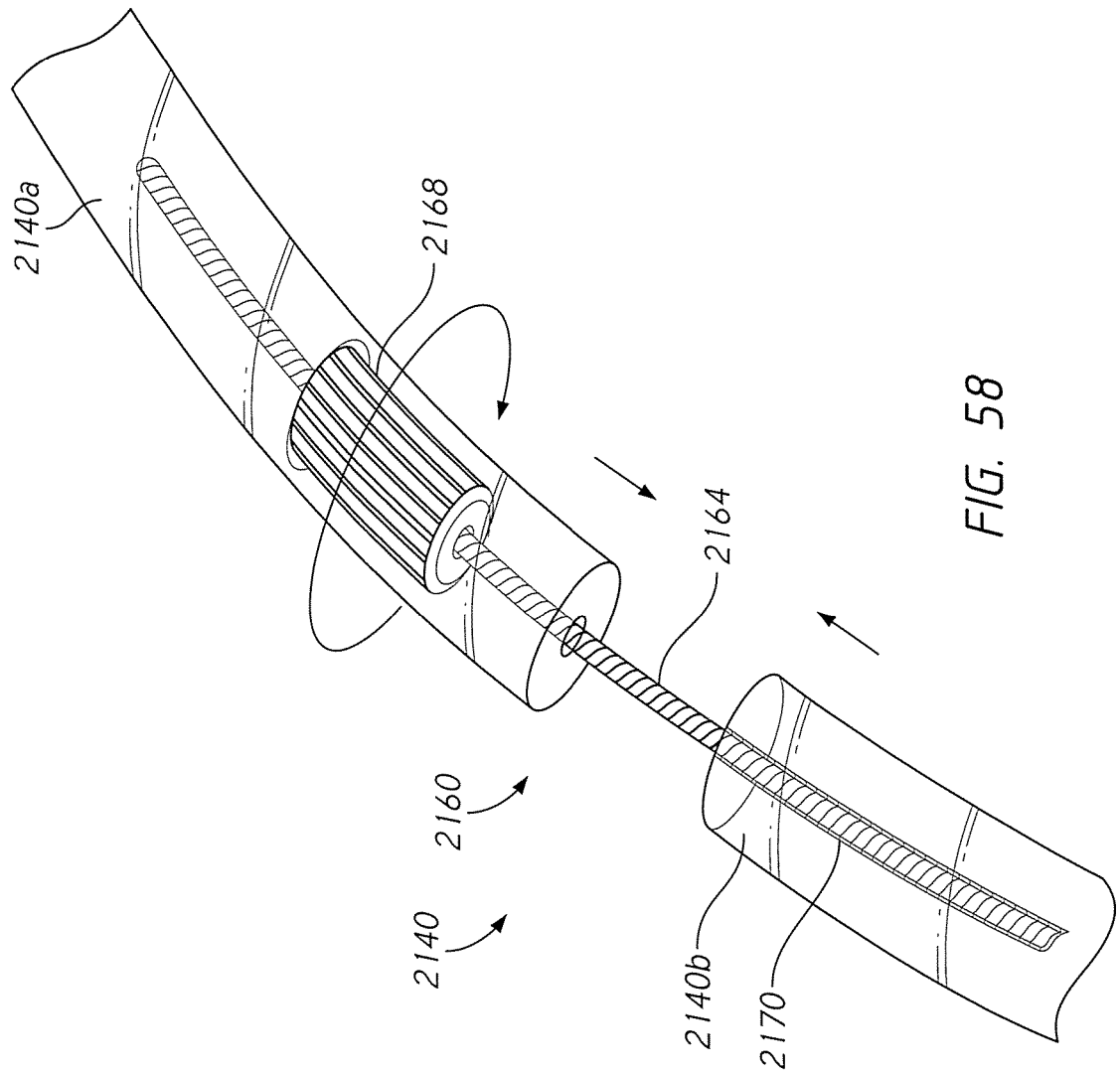

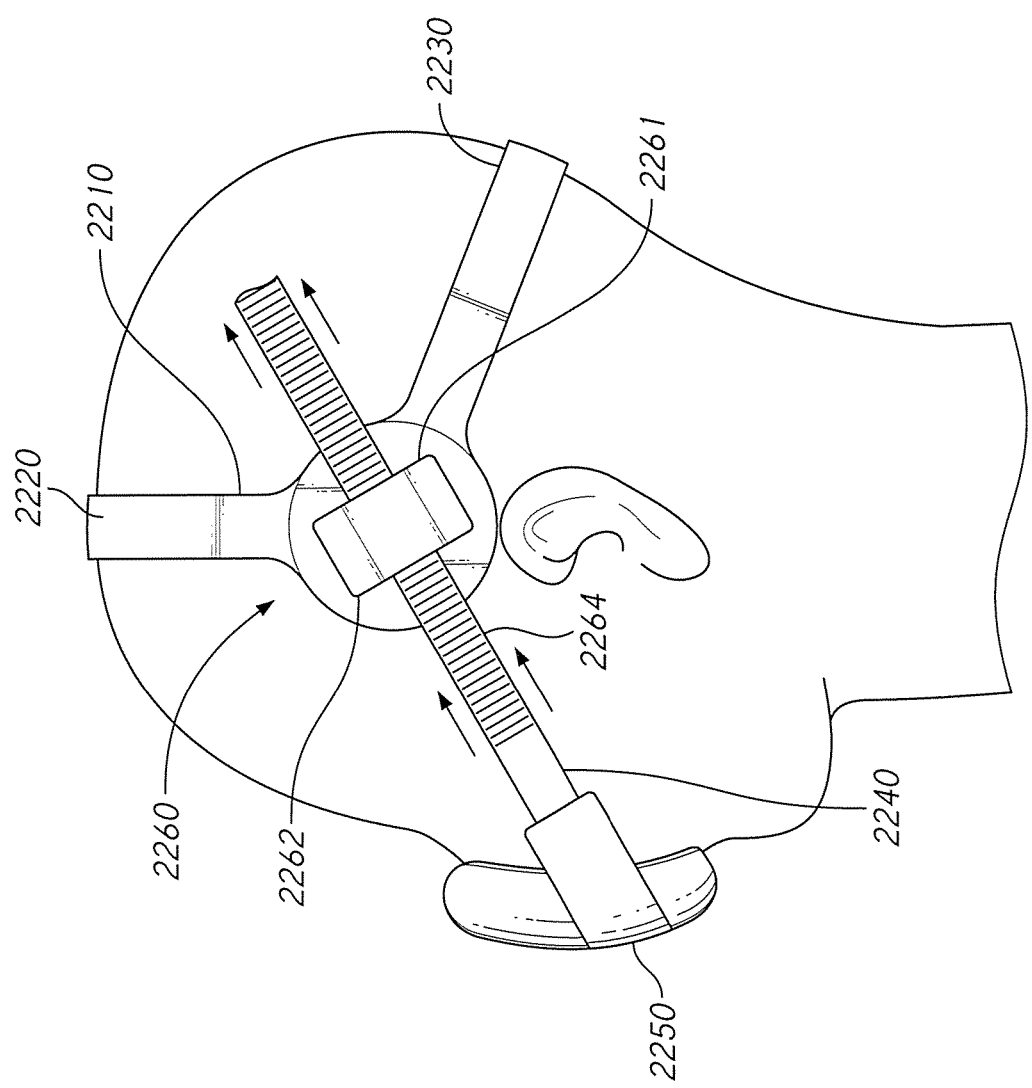

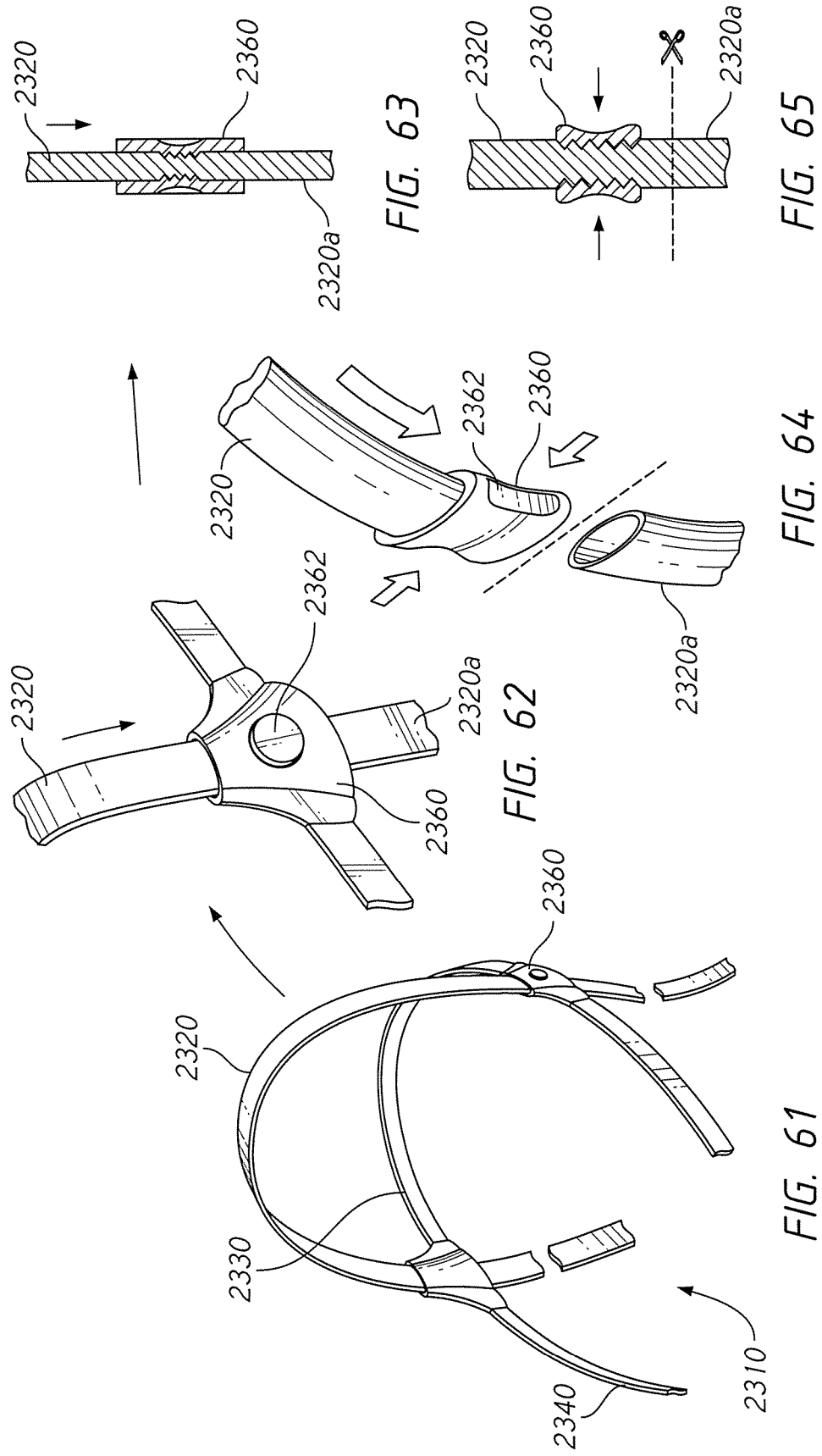

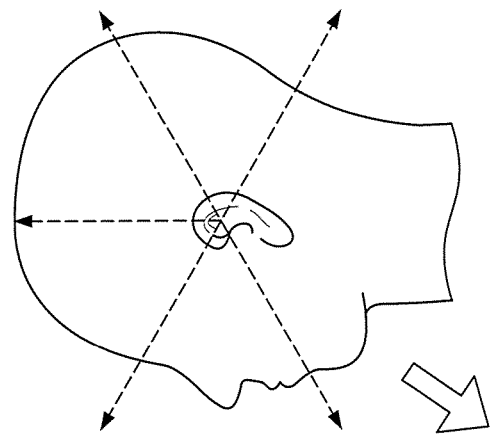
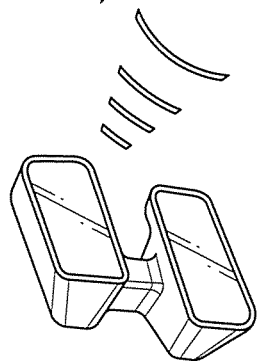
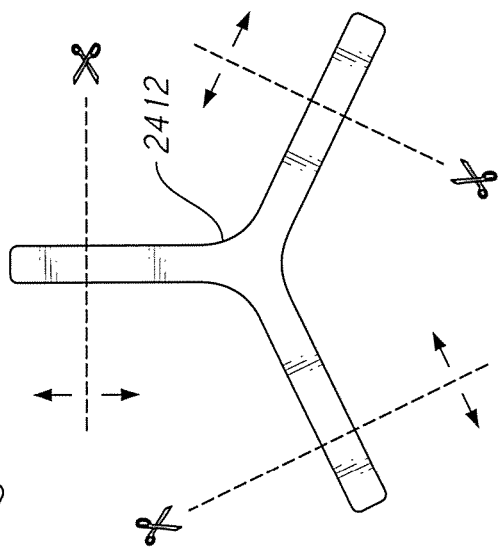
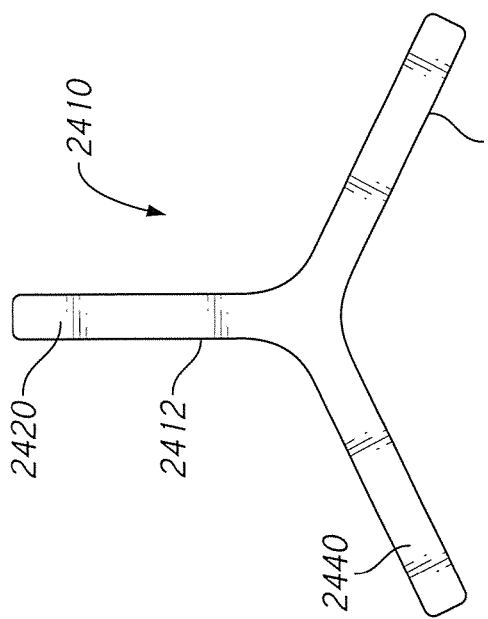
FIG. 66
FIG. 67
FIG. 68

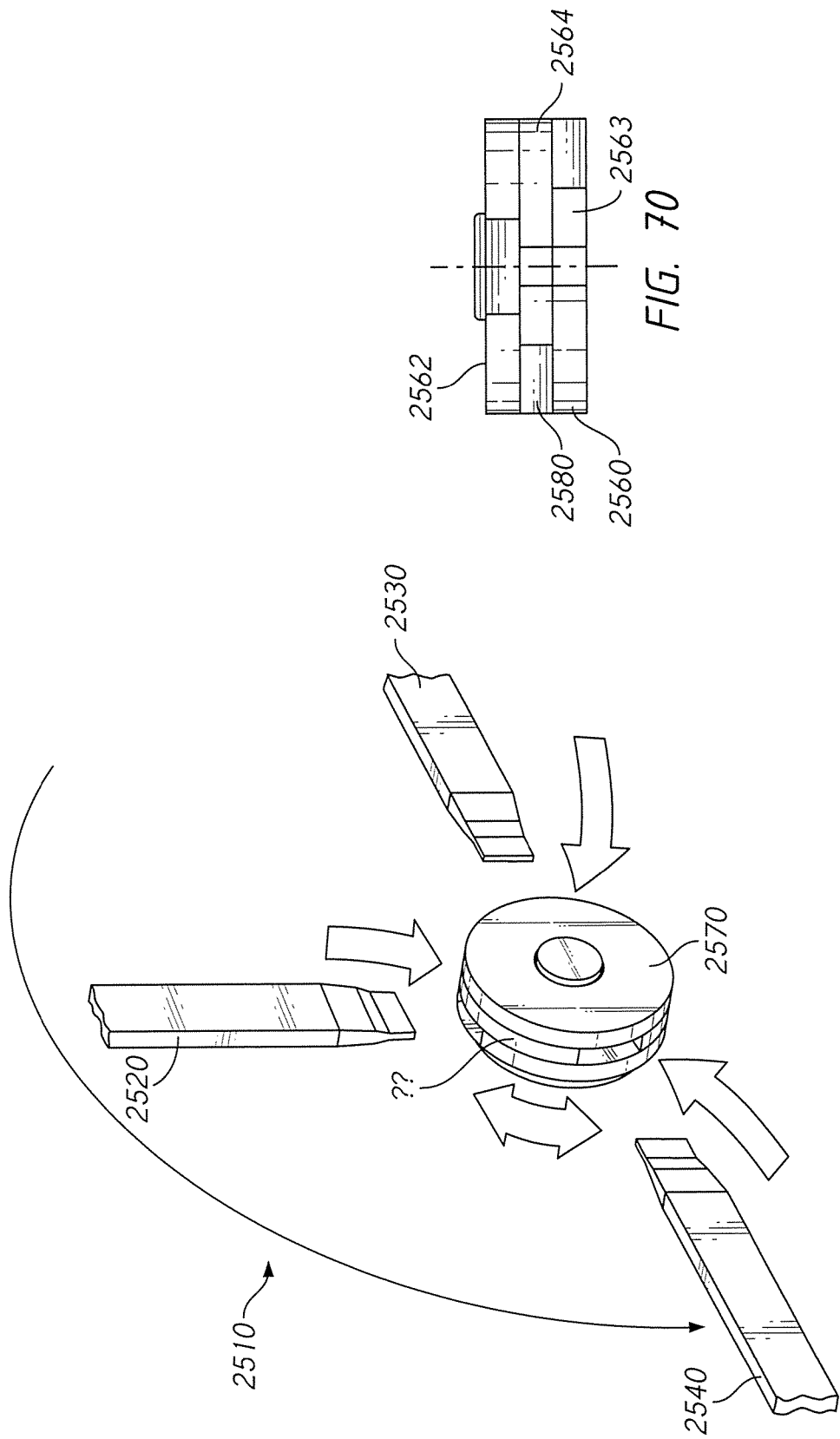

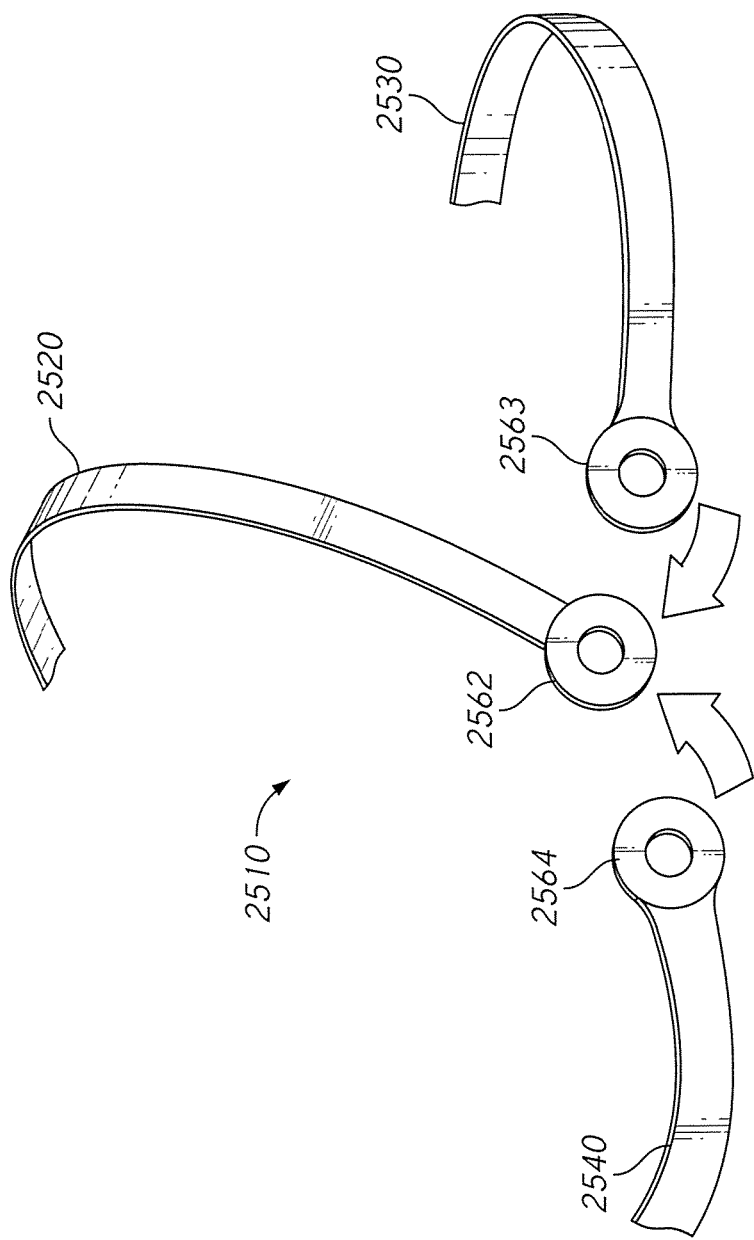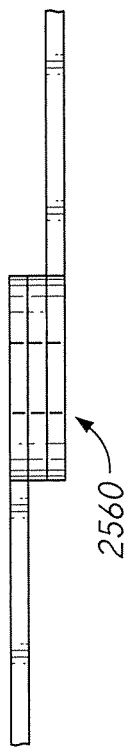

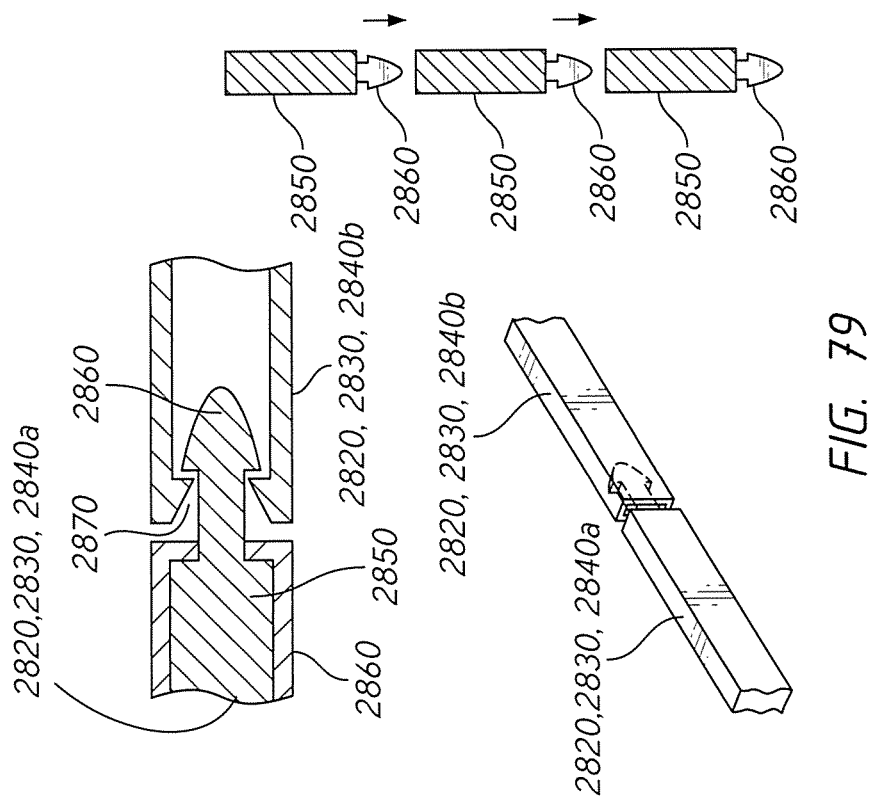
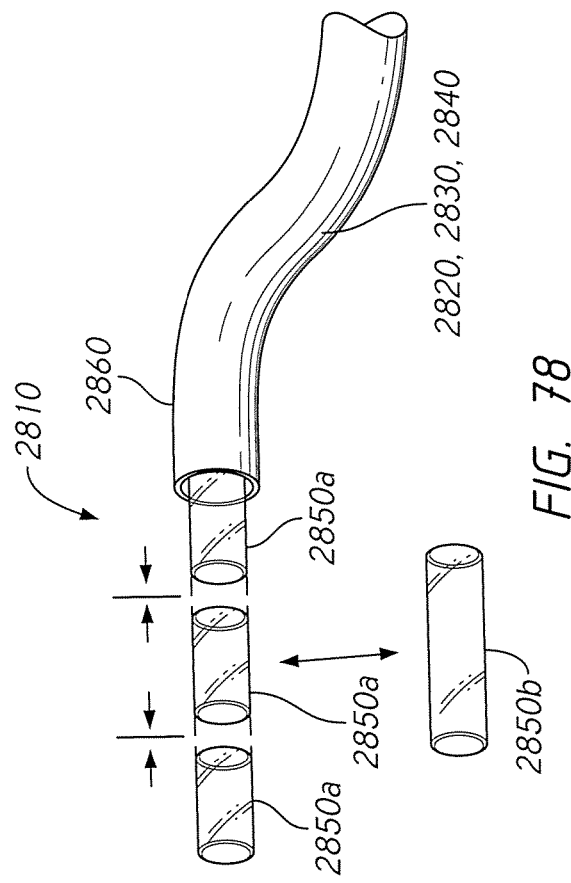
FIG. 79
FIG. 78

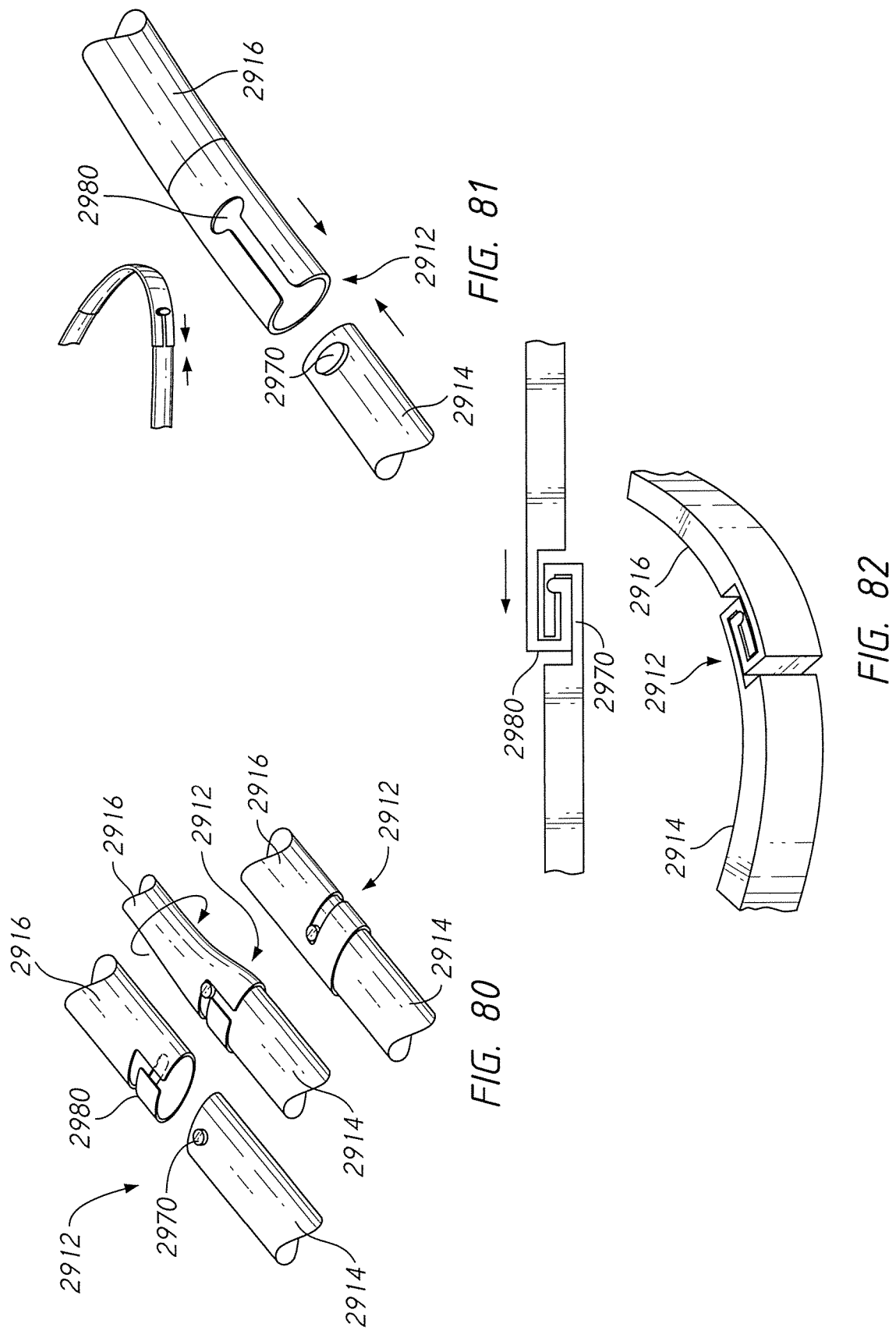

HEADGEAR ASSEMBLY

INCORPORATION BY REFERENCE TO ANY PRIORITY APPLICATIONS

This application is related to and claims the benefit of U.S. Provisional Patent Application Nos. 62/196,730, filed Jul. 24, 2015, and 62/364,247, filed Jul. 19, 2016, the entireties of which are hereby incorporated by reference herein and made a part of the present disclosure.

BACKGROUND

Technical Field

The present disclosure generally relates to a headgear assembly for use in securing a respiratory mask to a user's face. More particularly, the present disclosure relates to a headgear assembly that is customizable to fit a range of head sizes.

Description of the Related Art

Respiratory masks are used to provide respiratory therapies such as, but not limited to, continuous positive airway pressure (CPAP), non-invasive ventilation (NIV) or oxygen therapy to patients, or users. In CPAP therapy in particular a respiratory mask is secured to a user's face such that a supply of pressurized air is applied to their airways. A headgear assembly is used to secure the mask to the user's face.

Some headgear assemblies known in the art comprise a plurality of interconnected straps that extend over and around a user's head to secure the respiratory mask. The straps are generally made from a flexible and in some cases elasticated, such as Breath-o-Prene® brand breathable foam and fabric composite. The headgear assemblies are usually available in a range of sizes to suit users with differing head sizes. The size of headgear that is provided to a user is usually dictated by the size of the mask that they select.

The size of the headgear can be further adjusted to fit each individual user's head size, via an adjustment mechanism. The adjustment mechanisms used in the prior art headgear assemblies usually includes a buckle arrangement such that a pair of headgear straps pass through the buckle and double back on themselves, wherein they are secured in place by a fastener such as Velcro® or Paiho™ brand hook and loop fasteners. Adjustment mechanisms such as these provide continuous adjustment and in some configurations form the means for connecting the mask to the headgear assembly.

The problem with such headgear assemblies is that they require frequent adjustment by the user to maintain the correct sizing and thus a comfortable fit. This is a result of the fasteners (e.g., hook and loop) slipping over time or the need to disassemble the headgear from the mask for cleaning. Since continuous adjustment is provided it is difficult to replicate the exact sizing setting when the headgear assembly has been disassembled for cleaning, as there are usually no sizing indicators provided. The material of the headgear is also prone to losing its elasticity as a result of wear and tear which may result in the straps requiring tightening to maintain the level of fit and comfort between the user and the mask. The need to adjust the sizing of the headgear assembly before every use of the respiratory mask may waste time and cause frustration for the user, especially if they are unable to replicate their desired fit. This in turn may discourage the user from using their respiratory mask and thus compromises the therapy that they receive and their health.

It is therefore an object of the invention to provide a headgear assembly that overcomes or ameliorates at least one of the disadvantages of the prior art, or alternatively to provide the public with a useful choice.

BRIEF SUMMARY

In an aspect of the present disclosure, a headgear assembly for a respiratory mask is provided comprising a hub configured to connect a plurality of straps. The hub allows the headgear assembly to be modular.

In some configurations, the straps of the headgear assembly include a top strap configured to extend over the top of a user's head, in use, and a rear strap configured to extend around the rear of the user's head, in use.

In some configurations, the straps are flexible, inelastic and of a fixed length.

In some configurations, the straps have a connector element at each end.

In some configurations, the hub is provided in a plurality of sizes.

In some configurations, the hub comprises a top strap extension, rear strap extension and front strap extension.

In some configurations, the hub comprises a top strap extension, rear strap extension and two front strap extensions.

In some configurations, the front strap extensions are spaced apart by a support member.

In some configurations, the front strap extensions are elongate and separated by an angle.

In another aspect of the present disclosure, a headgear assembly for a respiratory mask is provided comprising a rear strap that extends between a pair of opposing hubs and passes about the rear of a user's head, and one or more front straps being configured to extend across a user's face to secure the respiratory mask in place. The hubs are provided in a plurality of sizes, such that the size of the headgear is determined by the size of the hubs. Such a configuration can allow the headgear assembly to be fitted to the user once and not require any further sizing adjustments.

In some configurations, the headgear assembly further comprises a top strap configured to extend between the hubs and across the top of the user's head in use.

In another aspect of the present disclosure, a headgear assembly for a respiratory mask is provided, comprising a pair of first hubs each having a first top strap extension and a first rear strap extension, and a pair of second hubs each having a second top strap extension and a second rear strap extension. The second top strap extension has a greater length than the first top strap extension, and the second rear strap extension has a greater length than the first rear strap extension.

In another aspect of the present disclosure, a headgear assembly for a respiratory mask is provided, comprising a plurality of straps that are configured to engage a user's head and support the respiratory mask. The straps are connected by a pair of hubs, wherein the hubs are provided in a plurality of sizes and are configured to determine the size of the headgear.

In another aspect of the present disclosure, a headgear assembly for a respiratory mask is provided, comprising a plurality of top straps provided in a range of sizes.

In some configurations, the headgear assembly further comprises a plurality of rear straps provided in a range of sizes.

In some configurations, one of the top straps is selectively connected between a pair of hubs.

In some configurations, one of the top straps and rear straps is selectively connected between a pair of hubs.

In another aspect of the present disclosure, a headgear assembly for a respiratory mask is provided, comprising a hub having a plurality of connection points.

In some configurations, the connection points are configured to be connected to one or more straps.

In another aspect of the present disclosure, a headgear assembly includes an interchangeable hub that is substantially rigid. A plurality of inelastic straps includes a top strap, rear strap and at least one front strap. The interchangeable hub provides a connection between the straps and defines an angle of each pair of the straps relative to one another. The interchangeable hub determines a size of the headgear by a spacing of the straps relative to one another.

In some configurations, a plurality of interchangeable hubs are provided or made available in a range of sizes, each of the interchangeable hubs comprising a connection point for each strap.

In some configurations, each of the interchangeable hubs comprises a plurality of connection points for each strap.

In some configurations, the interchangeable hub is a smart hub configured to detect movement, store data and communicate with an external computer device or system.

In some configurations, the straps are provided in a range of sizes so that straps can be used interchangeably as the top strap, the rear strap or the front strap when assembled.

In some configurations, a push fit connection is provided between the hub and each of the straps.

In some configurations, the hub and each of the straps include complementary magnetic connectors, wherein a position of the magnets within the hub determines the size of the headgear.

In some configurations, a heat shrink connection is provided between the hub and each of the straps.

In some configurations, a threaded connection is provided between the hub and each of the straps, between portions of one or more of the straps or between a pair of the straps.

In some configurations, one or both of the hub and at least one of the straps are injection-molded inside a fabric sleeve.

In another aspect of the present disclosure, a headgear assembly includes a strap connection hub that is substantially rigid and a plurality of inelastic straps. The hub connects the straps together and defines an angle between the straps. The headgear assembly can be constructed in a selected one of a plurality of possible sizes by connection of each of the straps to the hub in a selected one of a plurality of possible relative positions or by adjustment of the angle.

In some configurations, the hub comprises a mounting location for each of the plurality of straps, wherein the mounting location comprises a plurality of connection posts and the strap comprises a plurality of holes configured to receive the connection posts.

In some configurations, the hub comprises a front portion and a back portion that are configured to be connected together and located on opposing sides of the strap to hide the connection between the hub and the strap.

In some configurations, the hub comprises a mounting location for each of the plurality of straps, wherein the mounting location comprises a plurality of connection holes and the strap comprises a protrusion configured to engage one of the connection holes.

In some configurations, the hub comprises a plurality of stacked, rotatable discs, wherein each of the discs comprises a strap connection configured to connect one of the straps to the disc.

In some configurations, a connection between the hub and each of the straps comprises a magnetic connection.

In some configurations, the hub comprises a cutting mechanism to trim at least one of the straps to a length to suit a user.

In some such configurations, the cutting mechanism is configured to cut the strap and lock it in position relative to the hub in one action.

In another aspect of the present disclosure, a headgear assembly includes a unitary strap structure comprising an integrally-formed, inelastic top strap, rear strap and front strap. A spacer element joins ends of the straps or portions thereof and determines a size of the headgear assembly depending on a length of the spacer element used.

In some configurations, the spacer element is provided in a plurality of standard sizes.

In some configurations, the spacer element is customized for a particular user. The customization can include a length of the spacer element, identification information or size information.

In some configurations, the headgear assembly includes at least two spacer elements that connect a plurality of unitary strap structures.

In some configurations, the spacer elements have a push button to release a connection with the strap.

In some such configurations, the strap is adjustable in position with respect to the spacer element.

In some configurations, the headgear assembly comprises a push fit connection between the strap and the spacer.

In another aspect of the present disclosure, a headgear assembly includes a plurality of inelastic straps and a substantially rigid strap connection hub that connects the plurality of straps together at an angle relative to one another. The headgear assembly further includes a spacer element positioned between at least one of the straps and the hub. The spacer elements are provided or made available in a plurality of lengths to allow an effective length of the strap to be varied depending on the spacer element used.

In some configurations, the hub comprises a plurality of connector inserts and each of the straps has a hollow end configured to receive the connector insert. The spacer elements are tubular and are configured to fit over the connector inserts.

In some configurations, the straps are provided in a single size.

In another aspect of the present disclosure, a mask assembly includes a unitary inelastic headgear structure comprising a top strap, a rear strap and a front strap. The mask assembly also includes an interchangeable mask frame that connects a seal cushion to the headgear structure. The interchangeable mask frame is provided or made available in a plurality of sizes or lengths and a size of the mask frame selected determines a size of the headgear.

In some configurations, the headgear structure is a bifurcated structure.

In some configurations, the headgear structure comprises an upper front strap and a lower front strap.

In another aspect of the present disclosure, a headgear strap comprises a plurality of elongate, inelastic chain links. The headgear strap further comprises a connector arrangement for connecting a selected number of the chain links together to create the desired length of the headgear strap.

In some configurations, the connector arrangement comprises a sleeve that accepts the chain links.

In some configurations, the connector arrangement comprises an interconnection between the chain links.

In some such configurations, the interconnection comprises a male connector on one end of the chain link and a complementary connector on the other end of the chain link.

In another aspect of the present disclosure, a headgear assembly comprises a unitary inelastic strap structure comprising at least a top strap, a rear strap and a front strap. The headgear assembly further includes an interchangeable hub that fits over a junction between the top strap and the rear strap to define an angle between the straps. The hub can be provided or made available in several sizes defining several different angles between the straps.

Further aspects of the disclosure, which should be considered in all its novel aspects, will become apparent from the following description.

BRIEF DESCRIPTION OF THE DRAWINGS

The present disclosure will now be described by way of example only with reference to the figures, in which:

FIGS. 3a, 3b and 3c show side views of the hub of the headgear assembly of FIGS. 2a and 2b.

FIG. 11 is a side view of a headgear assembly having an interchangeable hub that orients two straps of the headgear assembly relative to one another.

FIG. 12 is a perspective view of a portion of the headgear assembly of FIG. 11.

FIG. 13 is a side view of the headgear assembly of FIG. 11 including a different version of the interchangeable hub.

FIG. 14 is a perspective view of a portion of the headgear assembly of FIG. 13.

FIG. 19 is a perspective view of a headgear assembly having an interchangeable spacer element.

FIG. 20 is a perspective view of various interchangeable spacer elements for use with the headgear assembly of FIG. 19.

FIG. 21 is a sectional view of a connection between a spacer element and a top strap of the headgear assembly of FIG. 19 taken along the line 21-21 of FIG. 19.

FIG. 22 is a perspective view of a portion of a headgear assembly having multiple interchangeable spacer elements configured for insertion into a rear strap of the headgear assembly.

FIG. 26 is a perspective view of a headgear assembly configured to incorporate a customized spacer element.

FIG. 27 is a side view of the customized spacer element of FIG. 26.

FIG. 28 is perspective view of a headgear assembly configured to incorporate spacer elements in one or more straps of the headgear assembly.

FIG. 29 illustrates a connection between the spacer element and strap portions of the headgear assembly of FIG. 28.

FIG. 32 is a perspective view of a headgear assembly configured to incorporate a spacer element in one or more straps of the headgear assembly.

FIG. 33 is a top view of a connection between the spacer element and strap portions of the headgear assembly of FIG. 32.

FIG. 34 is a sectional view of the connection between the spacer element and the strap portions of the headgear assembly of FIG. 32 taken along line 34-34 of FIG. 32.

FIG. 41 is a perspective view of a headgear assembly that includes a strap connector hub on each side of the headgear assembly. The strap connector hub is configured to receive one of a plurality of interchangeable strap locator inserts.

FIG. 42 illustrates an interior of the strap connector hub including the insert.

FIG. 43 illustrates the interchangeable inserts.

FIG. 47 is a perspective view of a headgear assembly that includes a strap connector hub on each side of the headgear assembly. The strap connector hub is configured to receive one or more straps of the headgear assembly in a plurality of possible positions relative to the hub.

FIG. 48 is an exploded view of a portion of the headgear assembly of FIG. 47 illustrating a connection between the hub and the straps.

FIG. 49 is a side view illustrating the connection between the hub and a strap of the headgear assembly of FIG. 47.

FIG. 50 is a side view of a portion of a headgear assembly that includes a strap connector hub on each side of the headgear assembly. The strap connector hub is configured to receive a strap of the headgear assembly in one of a plurality of possible positions.

FIG. 51 is a side view of the strap of the headgear assembly of FIG. 50.

FIG. 53 is a side view of a portion of a headgear assembly that includes a strap connector hub on each side of the headgear assembly. The strap connector hub is configured to receive a strap of the headgear assembly in one of a plurality of possible positions and includes a magnetic connection to secure an excess portion of the strap.

FIG. 54 is a rear view of the hub and strap of the headgear assembly of FIG. 53 with an excess portion of the strap disconnected.

FIG. 55 is a rear view of the hub and strap of FIG. 54 with the excess portion of the strap connected to the hub.

FIG. 58 is a perspective view of a threaded adjustment mechanism between portions of a headgear assembly.

FIG. 60 is a side view of a headgear assembly having a ratchet connection between a rear portion of the headgear assembly and a front portion of the headgear assembly.

FIG. 61 is a perspective view of a headgear assembly having strap connector hubs on each side of the headgear that adjustably support a top strap and incorporate mechanisms to trim or assist in trimming of excess portions of the top strap.

FIG. 62 is an enlarged view of an alternative hub of the headgear assembly of FIG. 61.

FIG. 63 is a side view of an alternative hub of the headgear assembly of FIG. 61.

FIG. 64 is a perspective view of another alternative hub of the headgear assembly of FIG. 61.

FIG. 65 is a side view of the hub of FIG. 64.

FIG. 66 is a side view of a component of a headgear assembly that is configured to be trimmed to size in accordance with a measurement of an individual user.

FIG. 67 is a view of a user being measured for individualization of the component of the headgear assembly of FIG. 66.

FIG. 68 illustrates the headgear component being trimmed.

FIG. 69 is a perspective view of a portion of a headgear assembly incorporating a strap connector hub that permits angular adjustment between the straps.

FIG. 70 is a top view of the hub of FIG. 69.

FIG. 71 is a side view of an alternative of the headgear assembly of FIG. 69 incorporating a strap connector hub having elements that are integral or unitary with the straps.

FIG. 72 is a top view of the hub of FIG. 71.

FIG. 78 illustrates an adjustable length strap for a headgear assembly.

FIG. 79 illustrates an interconnecting arrangement between link members of the strap of FIG. 78.

FIG. 80 illustrates a connection arrangement between straps or strap portions of a headgear assembly.

FIG. 81 illustrates another connection arrangement between straps or strap portions of a headgear assembly.

FIG. 82 illustrates still another connection arrangement between straps or strap portions of a headgear assembly.

DETAILED DESCRIPTION

Figure 1A:
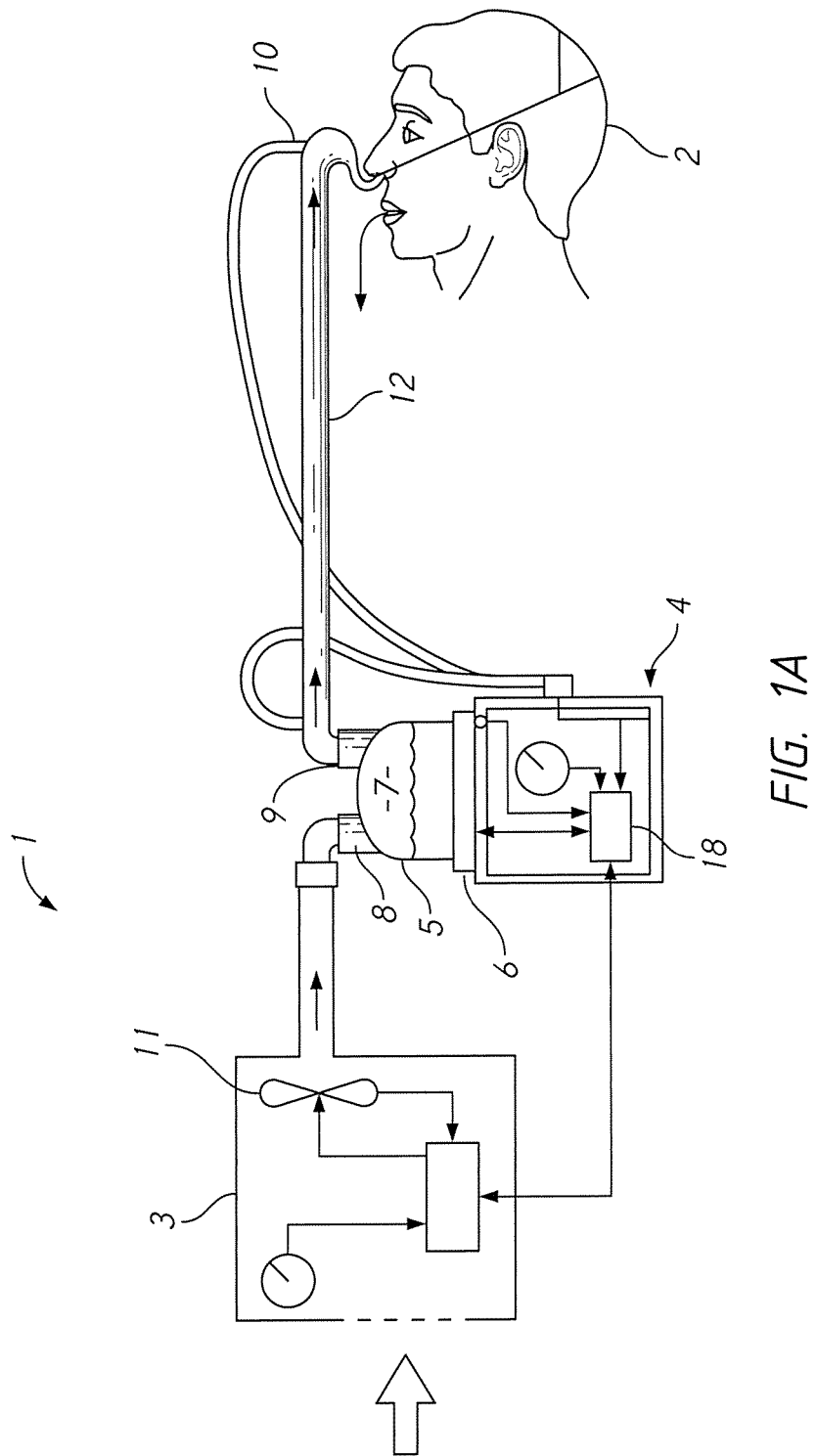
FIG. 1a shows a schematic view of a respiratory therapy system.

FIG. 1A shows a schematic view of a typical respiratory therapy system 1 for providing a stream of heated humidified gases at a pressure above atmospheric to a user 2. The system 1 includes a gases supply unit or blower unit 3 which in use receives gases from atmosphere and passes these through a fan unit 11 or similar inside the blower unit so that when the gases leave the blower unit 3, they are at a pressure above atmospheric, and are flowing at a certain flow rate. A humidifier unit 4 is located downstream from the blower unit 3, and in use receives the flow of pressurised gases from the blower unit 3. The humidifier unit 4 includes a water chamber 5 which in use contains a volume of water 7. The volume of water 7 in the chamber 5 is in use heated—in the embodiment shown in FIG. 1, the water 7 is heated by a heater plate 6 located underneath the chamber 5. The gases from the blower unit 3 pass into the chamber 5 via an entry port 8, the gases passing through the chamber 5 and across the surface of the water 7, becoming heated and humidified as they do so. The gases then pass out of the humidifier chamber 5 via a humidifier outlet port 9.

It should be noted that a modular humidification system has been described above—that is, a system where the humidifier unit 4 is a separate unit to the blower unit 3. An integrated humidification system could also be used—that is, a system where the blower unit and the humidifier unit are two integral parts of a single unit, or where the blower unit and the humidifier unit are rigidly attached or connected together in use.

Furthermore, it is preferable, although not necessary, that the overall respiratory system have a modular configuration. In the preferred embodiment the individual components are releasably interconnected to form the complete respiratory system. The modularity of the preferred system allows individual components to be maintained and replaced as necessary. It also permits components to be interchanged to meet individual user requirements. This is particularly useful in institutional applications, where a base unit (such as the blower and humidifier unit) can be used for different recipients at different times while the patient interface is interchanged to suit the particular user.

In use, a main supply conduit 12 is connected to the humidifier outlet 9. The heated and humidified gases stream exits the humidifier unit 4 via the humidifier outlet 9 and enters the main supply conduit 12, passing along the supply conduit 12 to an interface assembly 10 which is connected to the user end of the supply conduit 12.

Figure 1B:
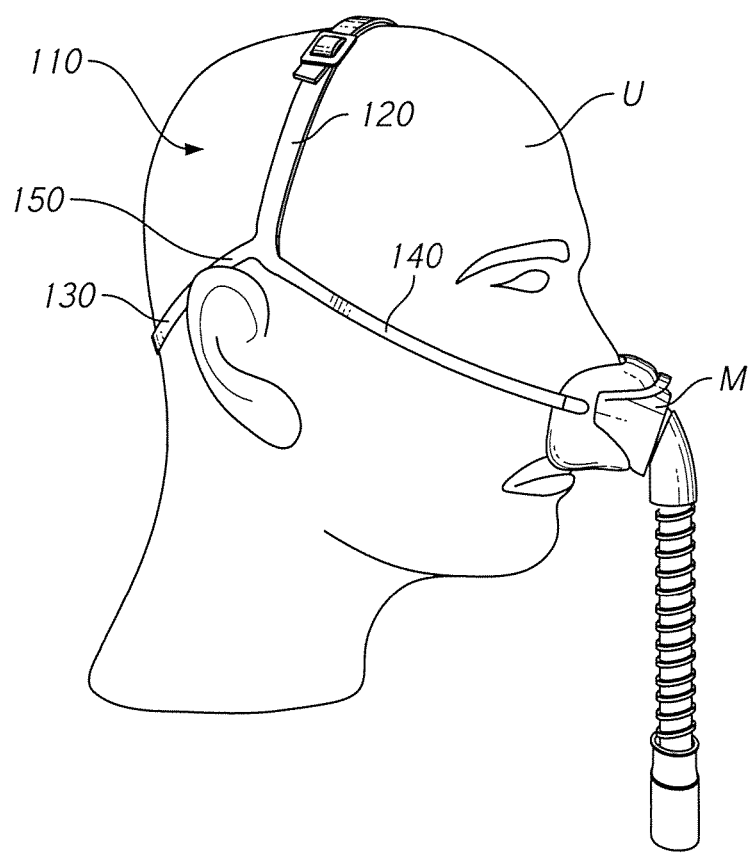
FIG. 1b shows a perspective view of a headgear assembly of the prior art.

FIG. 1B shows a headgear assembly 110 configured to secure a mask M to a user's face. The headgear assembly 110 comprises a top strap 120, a rear strap 130 and front straps 140 (only one shown).

Top strap 120 and rear strap 130 meet at a junction 150 above the ear of a user U, in use, forming a bifurcated rear portion. Top strap 120 comprises two portions, each extending from respective junctions 150 on each side of the headgear. Top strap 120 is adjustably connected by means such as a buckle at a top of the user's head. Rear straps 130 may be permanently or adjustably connected at the rear of the user's head. Front straps 140 extend from the junction 150, across the users cheeks and attach to a mask M, such that the mask M is secured to the user's head by the headgear assembly 110. Headgear assembly 110 can be made of a soft, flexible and elastic material, such as Breath-O-Prene® brand breathable foam and fabric composite. Headgear assembly 110 may be formed from a single sheet of material or from multiple pieces that are attached together.

Headgear assembly 110 can be fitted to a user's head size by adjusting the connections between the top straps 120 and rear straps 130. The size of the headgear assembly 110 is continuously adjustable and may creep during use. It may be necessary for users to adjust the sizing every time they use headgear arrangement 110, in order to achieve the best fit. Additionally, it may be necessary to re-fit the headgear assembly 110 after it has been cleaned. The need to adjust the sizing of headgear assembly 110 so frequently can be a hassle for users as it takes time and they may not be able to repeatably achieve a fitting that is effective and comfortable. It is also common for such headgear assemblies 110 to be provided in a range of sizes to better accommodate users with a range of different head sizes.

Figure 2A:
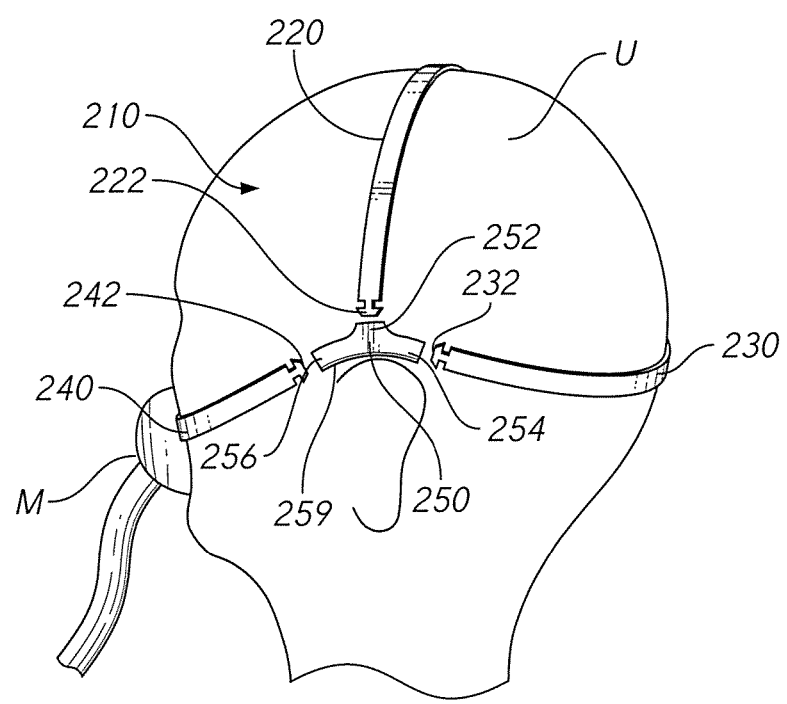
FIG. 2a shows a perspective view of a headgear assembly of the present disclosure.
Figure 2B:
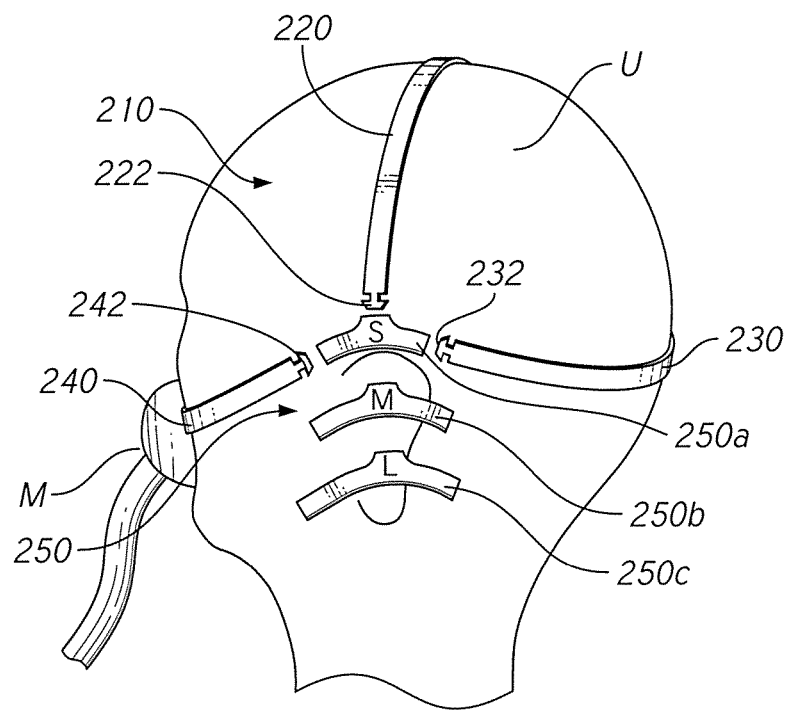
FIG. 2b shows a perspective view of another headgear assembly of the present disclosure.

FIG. 2A shows a first non-limiting exemplary embodiment of a headgear assembly 210 of the present disclosure, being configured to secure a respiratory mask M to a user's face. Headgear assembly 210 comprises a top strap 220 and a rear strap 230, ends of which are configured to be joined together by a hub 250 located on each side of a user's head, in use. When top strap 220 and rear strap 230 are connected together by hub 250 a bifurcated structure is formed. In at least some embodiments, when assembled, headgear assembly 210 forms a three-dimensional shape configured to closely follow the shape and contours of the head of the user. One side of the headgear assembly 210 is illustrated in FIGS. 2A and 2B; however, the other side of the headgear assembly 210 can be a mirror image of the illustrated side or can be of another suitable arrangement.

Top strap 220 and rear strap 230 comprise elongate and inelastic straps that are flexible and of a fixed length. Ends of straps 220 and 230 include a connector element 222, 232, allowing for connection to hubs 150.

Hubs 250 comprise a top strap extension 252, a rear strap extension 254, and a lower edge 259. Hubs 250 are configured to be positioned above the user's ear in use such that lower edge 259 is above the user's ear. Such a position limits or reduces the possibility of contact between the user's ears, for example when a user sleeps on their side, which may be undesirable to some users. Top strap extension 252 is configured to extend vertically upward from the user's ear in use. Rear strap extension 254 is configured to extend rearwardly of the user's ear in use. In some embodiments, rear strap extension 254 extends rearwardly and downwardly from the user's ear in use. In at least some embodiments, lower edge 259 is curved to follow the approximate shape of the user's ear.

Top strap 220 is configured to extend over a top of a head of a user U, in use, and has a length that is less than the distance between the top of the user's U ears. The length of top strap 220 cooperates with top strap extension 252 of hub 250 to form a total length such that, when assembled, hubs 250 are positioned above the user's ear as described above. In other words, top strap 220 dictates the vertical orientation of hubs 250 (when the user is sitting upright).

Rear strap 230 is configured to pass about the rear of the head of the user U, in use, and has a length that is less than the distance between the user's ears (i.e., the distance from ear-to-ear extending around the rear of the user's head). The length of rear strap 230 cooperates with rear strap extension 254 to form a total length that extends from a position approximately above the user's ear, around the rear of the user's head, to a similar position approximately above the other ear of the user. In other words, rear strap 230 dictates the fore and aft orientation of hub 250 (when the user is sitting upright). In at least some embodiments, rear strap 230 has a length such that, when connected to rear strap extensions 254, top strap extension 252 of hub 250 is relatively aligned with a vertical axis of the user's ear (when sitting upright).

In at least some embodiments, top strap 220 and rear strap 230 are the same fixed length. In some embodiments, top strap 220 and rear strap 230 are different fixed lengths.

Further, in other embodiments, top strap 220 is longer than rear strap 230. Still further, in additional embodiments, rear strap 230 is longer than top strap 220.

Top strap extension 252 of each hub 250 is configured to connect to connector elements 222 of top strap 220. Rear strap extension 254 is configured to connect to connector elements 232 of the rear strap 230. As top strap 220 and rear strap 230 are of a fixed length, the size of hub 250, top strap extension 252, and rear strap extension 254 determine the overall size of the headgear.

In at least some embodiments, connector elements 222 and 232 of top strap 220 and 230 are the same, for example a male or female connector. Top strap extension 252 and rear strap extension of hub 250 include a corresponding male or female connector. In such an embodiment, both top strap 220 or rear strap 230 are connectable to either the top strap extension 252 or rear strap extension 254.

In other embodiments, top strap 220 and rear strap 230 include different connector elements 222, 232. Top strap extensions 252 are configured to connect to top strap connector 222 and rear strap extensions 254 are configured to connect to rear strap connector elements 232.

In at least some embodiments, top strap 220 and rear strap 230 have different connector elements 222, 232 at each end of the respective straps. Two hubs 250 are provided, a first hub 250 includes a top strap extension 252 having a first top connector element and a second hub 250 includes a top strap extension having a second top connector element. The different connector elements 222 of top strap 220 are connectable to only one of the first and second top connector elements of the first and second hubs 240. Similarly, the first hub 250 includes rear strap extension 254 having a first rear connector element and the second hub 250 includes a rear strap extension having a second rear connector element. The different connector elements 232 of rear strap 230 are connectable to only one of the first and second rear connector elements. In such an embodiment, having different connector elements limits the possibility of incorrect or unintended assembly. In at least some embodiments, hubs 250 are made of a semi-rigid plastic material such as, but not limited to, nylon, polyethylene or polypropylene. Hubs 250 may have some flexibility to allow hubs 250 to conform to the curvature of the user's head. Such a construction, in part, allows headgear assembly 210 to maintain a 3D structure when not in use. It is advantageous for headgear assembly 210 to maintain a 3D structure when not in use as it minimises tangled straps and improves the ease with which it can be placed over the head of a user.

FIGS. 2B-3C show a non-limiting exemplary embodiment of a headgear assembly 210 that is provided with hubs 250 in a plurality of sizes, including, but not limited to, small 250a, medium 250b and large 250c. Hub sizes 250a, b and c allow a user to construct headgear assembly 210 in multiple sizes. In alternative embodiments, different hub sizes allow a manufacturer to assemble multiple sizes of headgear using fewer or common parts.

Each of the hub 250 sizes includes top strap extension 252 and a rear strap extension 254. Hubs 250 can also include a label 258a, b or c to indicate a particular size or configuration of said hub 250. Top strap extension 252a, b, c forms an extension to the length of top strap 220. Rear strap extension 254a, b, c forms an extension to the length of rear strap 230. Top strap extension 252a and rear strap extension 254a of small hub 250a each have a first height Ha and first length RLa, respectively. Top strap extension 252b and rear strap extension 254b of the medium interchangeable hub 250b each have a second height Hb and length RLb, respectively. Top strap extension 252c and rear strap extension 254c of small hub 250c each have a third height Hc and length RLc, respectively. The first second and third heights and lengths of each of the strap extensions can vary independently of each other, i.e. the height Ha,b,c of top strap extension 252a, b and c varies less than the length RLa,b,c of the rear strap extensions 254a, b and c.

Each headgear assembly 210 may be provided to a user in a disassembled configuration as a kit that includes a top strap 220, rear strap 230 and a plurality of pairs of hubs 250 in differing sizes. The user selects which size hub 250a,b,c is required for the size of their head and assembles the top and rear straps 220, 230 to the hub 250a,b,c. Once a hub 250a,b,c has been selected and assembled with the top strap 220 and rear strap 230, the headgear assembly 210 should require no further adjustment to fit to the size of the user's head. This is advantageous as it reduces the time required for the user to fit the mask M each time they use it, and also prevents the loss of sizing settings during cleaning of the mask and headgear assembly 210.

Headgear assembly 210 is connected to the mask M by a pair of front straps 240 (only one shown). Front straps 240 extend forward of the user's ears, in use, and include a connection element 242 at least at one end, allowing connection to hub 250. An opposing end of front straps 240 includes a mask connection element (not shown) configured to connect to the mask M. The mask connection element may be the same as the connection element 242. Alternatively, front straps 240 may have different connector elements 242 at each end.

Hub 250 also includes a front strap extension 256 configured to connect to connector element 242 of front straps 240. Front strap extensions 256 have a length FLa,b,c which forms an extension to the length of front straps 240. The length of front strap extension 256 can vary between hub sizes 250a,b,c.

Connector elements 222, 232, 242 may be push fit connectors that are received by corresponding receiving elements (not shown) within the top, rear and front strap extensions 252, 254, 256. In other embodiments, top, rear, and front strap extension 252, 254, 256 are received within connector elements 222, 232, 242.

Connector elements 222, 232, 242 may be configured to provide a permanent connection between the hubs 240 and straps 220, 230 and 240 that cannot be disconnected, a temporary connection that can be repeatedly connected and disconnected, or a semi-permanent connection that allows for a limited number of disconnections or at least makes it difficult to disconnect. It may be desirable for the connection between straps 220, 230, 240 and hubs 250 to be semi-permanent. A semi-permanent connection may allow the hub 250 size to be changed during fitting of headgear assembly 210 to the user's head, whilst providing a stable size that does not require regular adjustment.

In some variations the top, rear and front straps 220, 230 and 240 can be made from a semi-rigid plastic such as, but not limited to, Nylon, polyethylene, polypropylene, or a thermoplastic elastomer such as Arnitel® TPE VT3108 or PEBAX®. Furthermore they may be covered in a fabric casing or skin to provide added comfort for the user. In some configurations, any one or all of the headgear straps disclosed herein, including but not limited to top straps, rear strap or front straps can be constructed of a relatively rigid or semi-rigid plastic base or core that is at least partially covered by a fabric or textile material. In some configurations, the fabric or textile material covers a substantial entirety of an inner and/or an outer surface of the strap. In some cases, the fabric or textile layers forms a tubular structure that encloses the plastic base or core. In some configurations, the material forming the plastic base is injected onto or into a space created by the fabric or textile layer(s) in a molten state and allowed to harden such that the fabric or textile layer(s) is fixed to the plastic base. Embodiments of and methods of creating such straps are disclosed in Applicant's U.S. Patent Publication No. 2016/0074614, entitled INTRAMOLD HEADGEAR, the entirety of which is incorporated by reference herein and made a part of the present disclosure. Such straps can be referred to herein as "intramolded" straps.

In some configurations, the front straps 240 (or other straps 230, 240) could incorporate a length adjustment arrangement, which can incorporated a directional lock (e.g., a one-way friction mechanism). In some configurations, the length adjustment arrangement can allow for automatic length adjustment of the headgear assembly 210. Examples of such an arrangement are disclosed in Applicant's U.S. Publication Nos. US2016/0082217 entitled AUTOMATICALLY ADJUSTING HEADGEAR FOR PATIENT INTERFACE and US2016/0144146 entitled HEADGEAR ASSEMBLIES AND INTERFACE ASSEMBLIES WITH HEADGEAR, the entireties of which are hereby incorporated by reference herein and made a part of the present disclosure.

The further headgear assemblies disclosed herein can be the same as or similar to the headgear assembly 210 of FIGS. 2A-3C or can have components or features that are the same as or similar to corresponding or similar components or features of the headgear assembly 210 of FIGS. 2A-3C. For example, as described above, the straps of any of the headgear assemblies disclosed herein can be intramolded. In addition, the headgear assemblies can include one or more length adjustment arrangements, which can be automatic length adjustment arrangements. In some configurations, the automatic length adjusting arrangements can be incorporated in the front strap(s) of the headgear assembly. The headgear assemblies can include a pair of front straps, or a single front strap that extends from one side of the headgear assembly to the other. The top strap extends over the user's head from one side to the other and can be positioned in any location on the user's head. That is, the top strap can be a forehead strap or a crown strap. The spacer elements or hubs can be semi-rigid and can be at least somewhat conformable to conform the user's head. Furthermore, components and features of one headgear assembly can be incorporated in other headgear assemblies or can be interchanged with corresponding or similar components or features.

Figure 4:
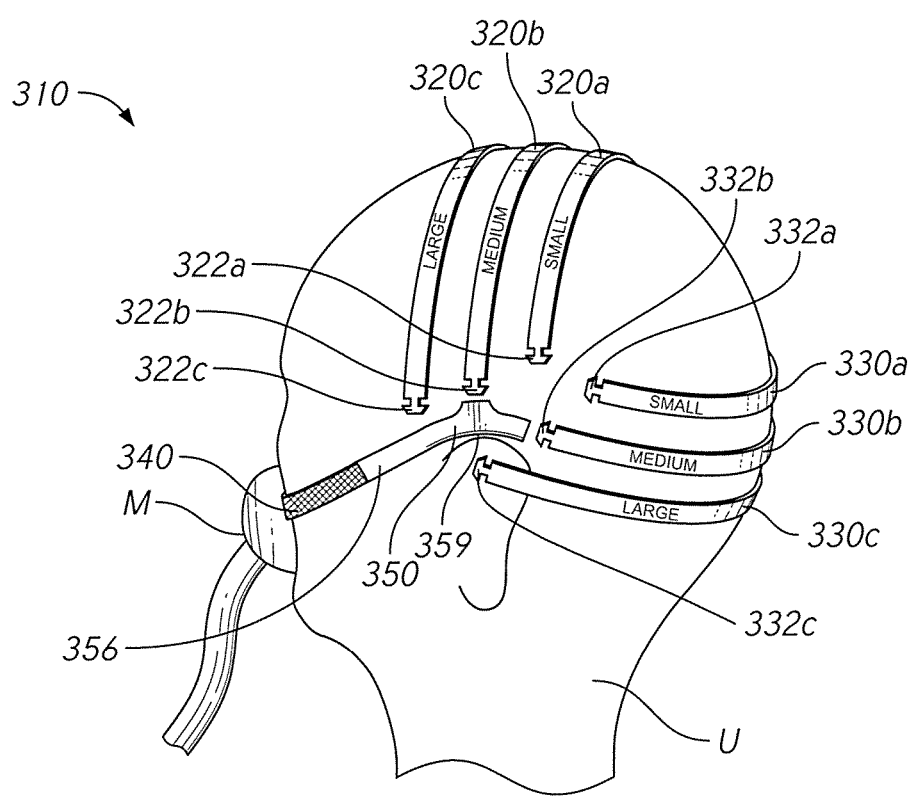
FIG. 4 shows a perspective view of another headgear assembly of the present disclosure.

FIG. 4 shows another non-limiting exemplary embodiment of a headgear assembly 310 of the present disclosure. Headgear assembly 310 comprises a top strap 320 provided in a plurality of sizes (e.g., small 320a, medium 320b and large 320c), a rear strap 330 also provided in a plurality of sizes (e.g., small 330a, medium 330b and large 330c) and a pair of front straps 340. Top strap 320 and rear strap 330 comprise an elongate and inelastic strap that is flexible. Top strap 320 and rear strap 330 have connector elements 322, 332 at each end that are configured to be joined to a pair of opposing hubs 350 (only one shown), such that a three dimensional (3D) structure is formed.

Hubs 350 are configured to be positioned above the user's ear, in use, such that lower edge 359 is above the user's ear. This position limits or reduces the possibility of contact between the user's ears, for example when a user sleeps on their side, which may be undesirable to some users. Top strap extension 352 is configured to extend vertically upward from the user's ear in use. Rear strap extension 354 is configured to extend rearwardly of the user's ear in use. In some embodiments, rear strap extension 354 extends rearwardly and downwardly from the user's ear in use. In at least some embodiments, lower edge 359 is curved to follow the approximate shape of the user's ear.

Top strap extension 352 is configured to connect to the connector element 322 of the top strap 320 and the rear strap extension 354 is configured to connect to the connector element 332 of the rear strap 330. The front strap extension 356 is configured to transition into the front straps 340. The connector elements 322 and 332 are shown as push fit connectors that are received by corresponding receiving elements (not shown) within the top and rear strap extensions 352, 354. Various combinations of connectors may be used, see e.g., discussion above related to FIG. 2A.

Top strap 320 is provided in a plurality of sizes, such as but not limited to, small 320a, medium 320b and large 320c. Top strap 320 is configured to extend over a top of a head of a user U, in use, and has a length that is less than the distance between the top of the user's U ears. The length of top strap 320 cooperates with top strap extension 352 of hub 350 to form a total length such that, when assembled, hubs 350 are positioned above the user's ear in use.

Rear strap 230 is configured to pass about the rear of the head of the user U, in use, and has a length that is less than the distance between the user's ears. The length of rear strap 230 cooperates with rear strap extension 254 to form a total length that extends from a position approximately above the user's ear, around the rear of the user's head, to a position approximately above the other ear of the user. Rear strap 330 is provided in a plurality of sizes, such as but not limited to, small 330a, medium 330b and large 330c.

A user selects one of top straps 320a, b and c to adapt the overall size of the headgear assembly 310 such that hubs 350 are located as described above. A user also selects one of rear straps 330a, b and c to adapt the overall size of the headgear assembly 310 such that hubs 350 are located as described above. Headgear assembly 310 thereby provides a headgear assembly that is customizable to each user U.

The length of the top and rear straps 320, 330 varies between sizes. For example, medium and large top straps 320b, c and rear straps 330b, c have a longer length than the small top strap 320a and rear strap 330a respectively.

Front straps 340 are configured to extend forward of the user's U ears, in use, and are attached to a mask M such that it is secured to the user's face. Front strap's 340 can be integrally formed with the hub 350, permanently attached to the hub 350 or removeably attached to hub 350 by a connector element (not shown) similar to connector elements 322 and 332. Further, the front straps may be of a similar or different construction to top strap 320 and/or rear strap 330.

Each headgear assembly 310 may be provided to the user in a disassembled configuration as a kit that includes a plurality of top straps 320 in a range of sizes, a plurality of rear straps 330 in a range of sizes, a pair of front straps 340 that are attached to a pair of interchangeable hubs 350. The user selects which top strap 320 size and which rear strap 330 size is required for the size of their head, and assembles them to the hub 250. Once the correct top strap 320 and rear strap 330 have been selected and assembled the headgear assembly 310 should require no further adjustment to fit to the size of the user's head.

Figure 5:
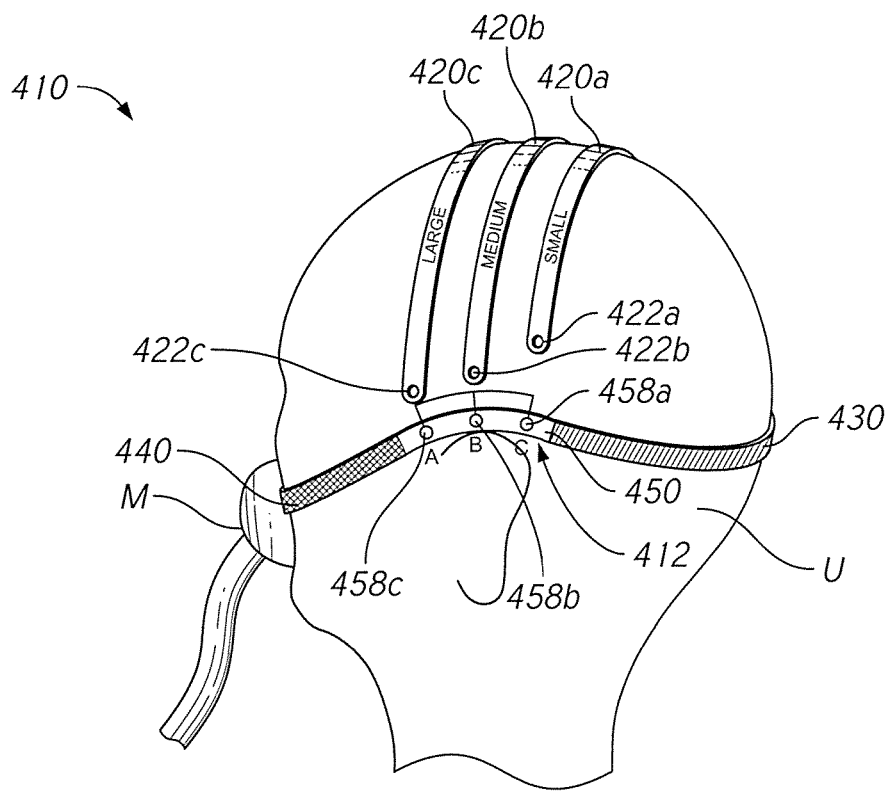
FIG. 5 shows a perspective view of another headgear assembly of the present disclosure.

FIG. 5 shows another non-limiting exemplary embodiment of a headgear assembly 410 according to the present disclosure. Headgear assembly 410 comprises a top strap 420 provided in a plurality of sizes (e.g., small 420a, medium 420b and large 420c), a rear strap 430, and a pair of hubs 450. Hubs 450 and rear straps 430 are joined to form a continuous strap 412 that extends from one side of the user U around the rear of the user's head to the other side of the user U. Front straps 440 are configured to extend forward of the user's U ears, in use, and are attached to the mask M such that it is secured to the user's face. Hubs 450 comprise an elongate strap portion that arches over the user's U ear, in use, and includes a plurality of connection points 458a, b, c. In a variation of this embodiment rear strap 430 and hubs 450 can be integrally formed as a single component.

Top strap 420 and rear strap 430 comprise elongate and inelastic straps that are flexible, and may be substantially straight or have a curvature.

Top strap 420 is configured to extend over the top of a head of a user U, in use, and has a length that is less than the distance between the top of the user's U ears. Top strap 420 is provided in a plurality of sizes, such as but not limited to, small 420a, medium 420b and large 420c wherein the size corresponds to a length of the strap. The different top strap sizes 420a, b and c, are configured to adapt the overall size of the headgear assembly 410 such that it can be customized to each user U. The top strap 420 includes an integrally formed connector element 422, which is configured to connect top strap 420 between the pair of hubs 450 at one of the corresponding connector points 458a, b, or c. The plurality of connector points 458 on the hub 450 allow the user U to select the location at which the top strap 420 is connected to the hub 450, such that a comfortable and stable fit is provided.

Each headgear assembly 410 may be provided to the user in a disassembled configuration as a kit that includes a plurality of top straps 420 in a range of sizes or configurations, and a continuous strap 412 that comprises the pair of hubs 450 and rear strap 430. The user selects which top strap 420 size is required for the size of their head (such that hubs 450 are positioned above the user's ears), and assembles the selected top strap 420a, b, or c to the hub 450 at a connector point 452a,b,c that is comfortable and stable. In at least some embodiments, connector point 452a, b, or c is selected so that, when assembled, top strap 420 is relatively aligned with a vertical axis of the user's ear while rear strap 430 is in contact with the rear of the user's head. In other words, top strap 420 dictates the vertical orientation of hubs 450 (when the user is sitting upright) and selection of connector point 452a, b, or c dictates the fore and aft orientation of top strap 420. Once the correct top strap 420 has been selected and assembled the headgear assembly 410 should require no further adjustment to fit to the size of the user's head.

Figure 6:
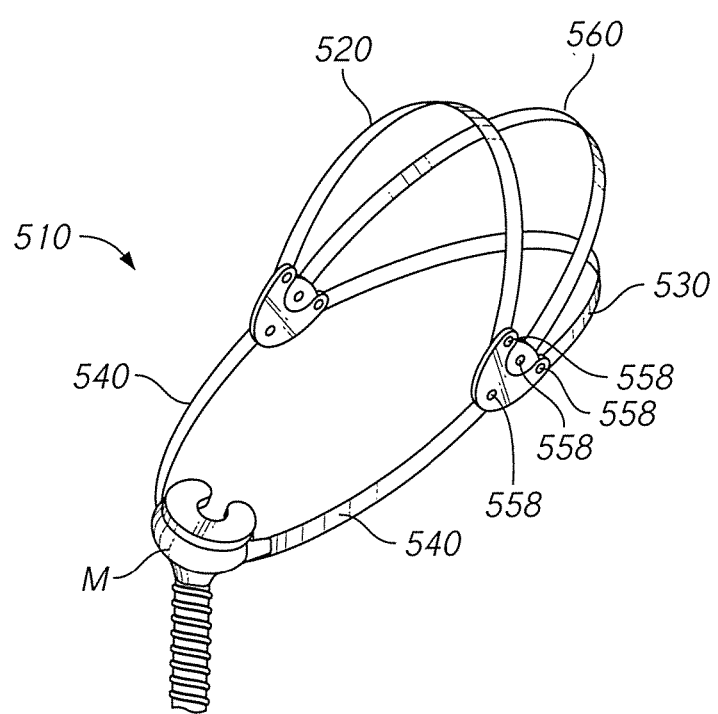
FIG. 6 shows a perspective view of another headgear assembly of the present disclosure.

FIG. 6 shows another non-limiting exemplary embodiment of a headgear assembly 510 according to the present disclosure. Headgear assembly 510 comprises a pair of hubs 550, a top strap 520, rear strap 530 and optional extra strap 560. The top strap 520, rear strap 530, and extra strap 560 comprise elongate and inelastic straps that are flexible, and are substantially straight, but may have a curvature in other variations of this embodiment.

Top strap 520 is configured to extend over the top of a user's head, in use, between hubs 550. Rear strap 530 is configured to extend around the rear of a user's head, in use, between hubs 550. Extra strap 560 can be selectively assembled such that it extends between hubs 550 and is positioned between top strap 520 and rear strap 530 to provide increased stability. Alternatively a user may choose to use only one of either the top strap 520 or rear strap 530.

Top strap 520, rear strap 530, and extra strap 560 may be substantially the same and thus interchangeable. The straps 520, 530, 560 may be provided in a plurality of lengths, such that a user can select the appropriate sizes for their head size (as discussed with respect to FIGS. 4 and 5, for example).

Hubs 550 are configured to be positioned above and/or behind the user's ears and include a plurality of connection points 558. Connection points 558 are configured to connect to a corresponding connection element of each of the top strap 520, rear strap 530, and extra strap 560. Hubs 550 are made of a semi-rigid material. Connection points 558 may, in some variations of the embodiment, allow the top straps 520, rear straps 530 and extra strap 560 to rotate relative to hub 550. The connections between hubs 550 and straps 520, 530, and 560 may be permanent or temporary.

Figure 7:
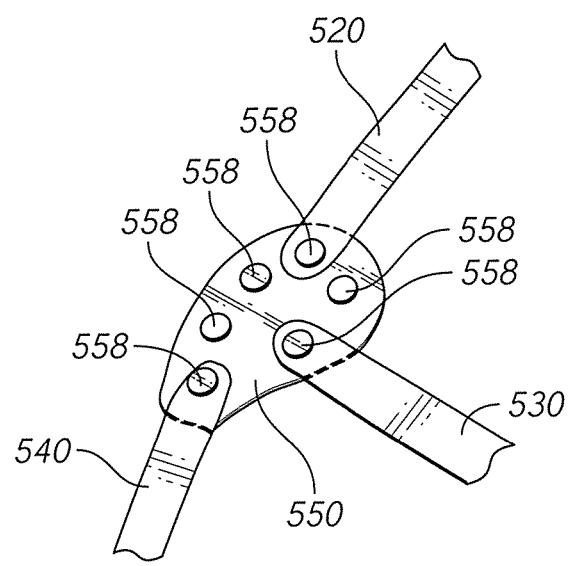
FIG. 7 shows a side view of a hub suitable for use in the headgear assembly of FIG. 6.

A variation of hub 550a is shown in FIG. 7. In this variation hub 550a includes additional connection points 558. The additional connection points allow the user to choose where top strap 520, rear strap 530 and extra strap 560 are connected to hub 550a. This allows the angle of the straps 520, 530, and 560 to be customised to each user.

Front straps 540 are configured to connect to hubs 550 at one of the connection points 558, at one end. Front straps 540 extend forward of the user's U ears, in use, and are attached to the mask M such that it is secured to the user's face, at the other end. In some embodiments, front strap 540 can be of the same construction as top strap 520, rear strap 530 and extra strap 560.

Figure 8:
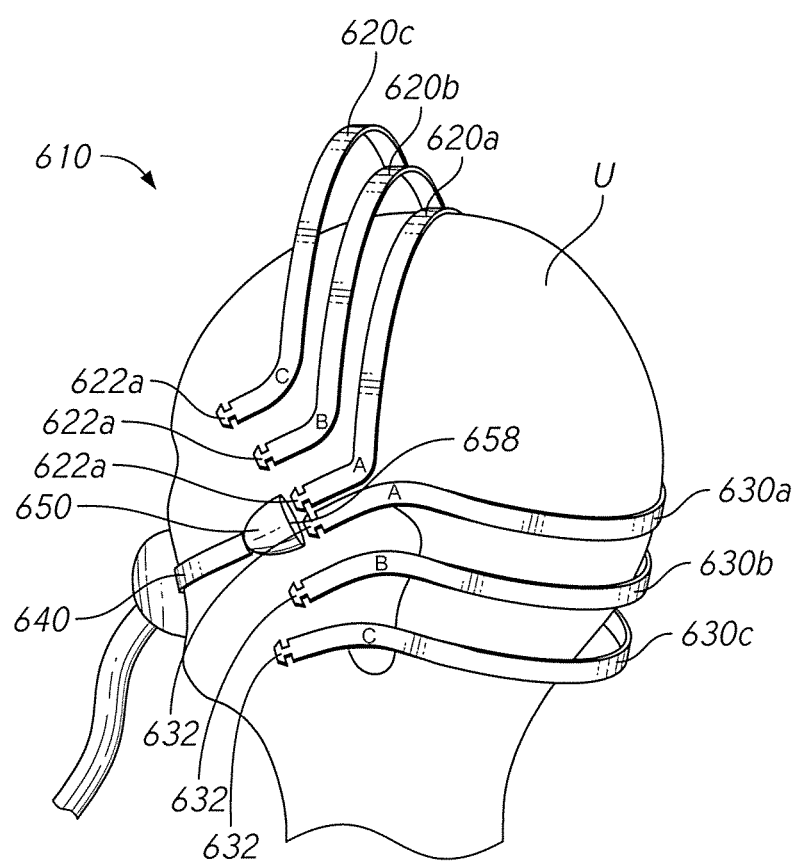
FIG. 8 shows a perspective view of another headgear assembly of the present disclosure.

FIG. 8 shows another non-limiting exemplary embodiment of a headgear assembly 610 of the present disclosure. The headgear assembly 610 comprises a plurality of top straps 620, a plurality of rear straps 530 and a pair of hubs 640. Top straps 620 and rear straps 630 have similar geometry and are thus interchangeable by changing their orientation. Top straps 620 and rear straps 630 comprise elongate curved straps that are made of an inelastic material and are provided in a plurality of different sizes, lengths, or configurations 620,a, b, c, 630a, b, c. Straps 620, 630 are configured to be connected to the hub 650. Top straps 620 are configured to curve upwards away from the hub 650, towards the top of the user's head, in use. Rear straps 630 are configured to curve downwards from hub 650, over the user's ear and around the rear of their head, in use.

Front straps 640 are configured to be attached to a mask M at one end and extend across the user's cheeks to connect to the hub 650 at the other end. In at least some embodiments, top, rear and (optionally) front straps 620, 630 and 640 are injection moulded plastic and may be covered in fabric for comfort.

Hubs 650 are connected to the front straps 640 at a first end and include a pair of connector points 658 at an opposing end. Connector points 658 are configured to connect to a connector element 622, 632 of top and rear straps 620, 630 respectively. Front straps 640 may be permanently connected to the hub 650, and in some embodiments may be integrally formed or over-moulded.

Figure 9:
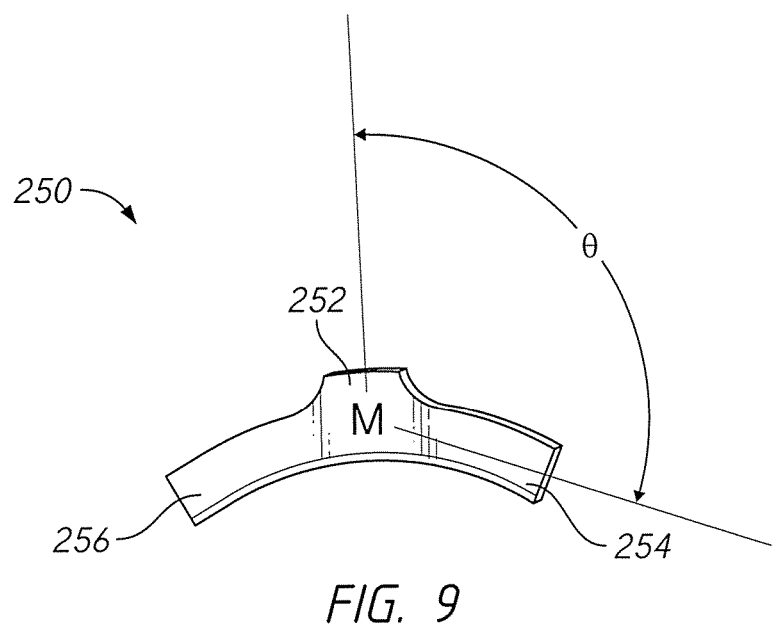
FIG. 9 shows another side view of the hub of the headgear assembly of FIGS. 2a to 3c.

FIG. 9 shows a hub 250 of the headgear assembly 210 (as shown in FIGS. 2A to 3C). Top strap extension 252 and rear strap extension 254 form an angle θ. Angle θ determines the angular spacing between top strap 220 and rear strap 230 and thus controls, in part, where top strap 220 and rear strap 230 contact the user's head, in use. The plurality of hub sizes 250a, b, c, may be provided in differing configurations wherein the angle θ changes between sizes. Or, alternatively hubs 250 can be provided in different angle configurations that are also available in different sizes.

In alternative embodiments not shown hubs 250 may be provided in a range of different sizing configurations. For instance, the height H of top strap extension 252 and length RL of rear strap extension 254 can be varied relative to each other, to provide at least 9 sizing configurations, as illustrated in the table below:

|  |  | Rear strap extension length | | |
| --- | --- | --- | --- | --- |
|  |  | Short | medium | long |
| Top strap extension length | Short | X | X | X |
|  | Medium | X | X | X |
|  | long | X | X | X |

Figure 10B:
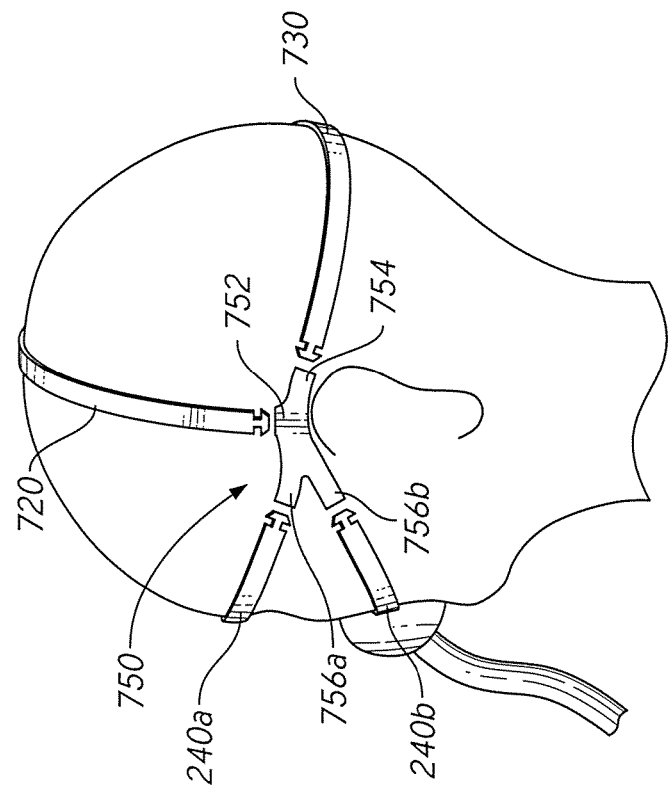
FIGS. 10a and 10b shows side views of another embodiment of the headgear of FIGS. 2a and 2b.
Figure 10A:
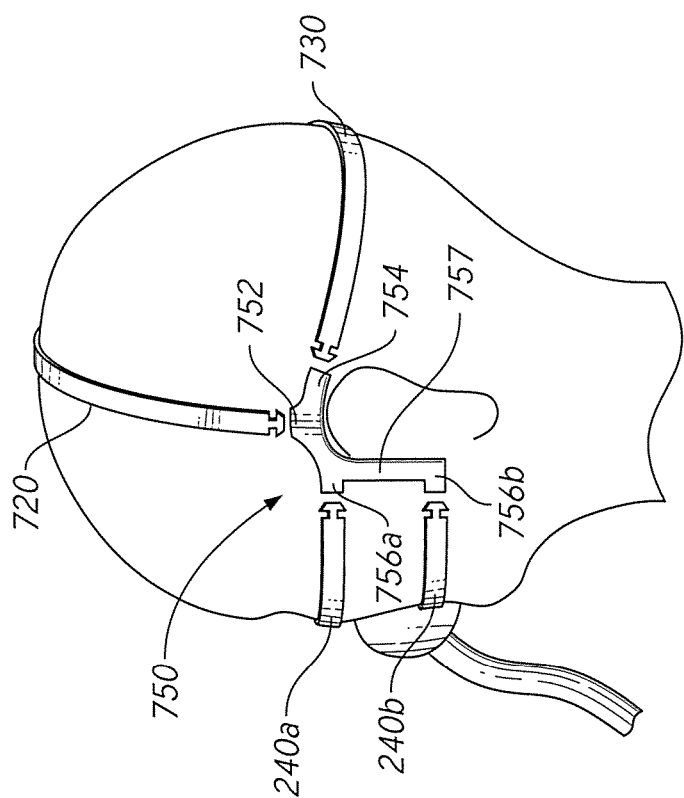

FIGS. 10a and 10b show two non-limiting exemplary embodiments of a hub 750, having different configurations. In these embodiments hub includes two front strap extensions 756a, b. Extending from each of the two front strap extensions 756 are upper and lower front straps 240a, b.

In the embodiment of FIG. 10a the hub 750 extends around the front and top of the user's ear, in use. An upper front strap extension 756a and a lower front strap extension 756b are vertically spaced apart by a support member 757. Upper front strap 240a extends from upper strap 756a to mask M (not shown). Lower front strap 756b extends forward from lower front strap extension 756b to the mask M (not shown). In at least some embodiments, upper and lower front straps 240a, b are substantially parallel with each other. In other embodiments, upper and lower front straps 240a, b converge in the forward direction. In other embodiments, upper and lower front straps diverge in the forward direction. In at least some embodiments, upper front straps 240a cross the user's cheeks below the eyes.

In the embodiment of FIG. 10b upper front strap extension 756a and lower front strap extension 756b are elongated and separated by an angle. Upper and lower front straps 240a, b extend forward in a diverging manner. In use, upper front strap 240a extends forward and upward, above the user's eyes and lower front straps extends forward and downward, across the user's cheek. In at least some embodiments, upper front straps connect to a T-piece or forehead support of a mask.

In at least some embodiments, hubs 750 of FIGS. 10a and 10b may further comprise different sizes in a manner similar to other embodiments disclosed herein.

Hub 750 can be semi-rigid such that front strap extensions 756 are stable and help to prevent rotation of a mask on the user's face.

The top straps 220, 320, 420, 520, 620, 720 and rear straps 230, 330, 430, 530, 630, 730 have been described as being inelastic. It is to be understood that in some alternative embodiments the straps may have a degree of elasticity.

FIGS. 11-14 illustrate another non-limiting exemplary embodiment of a headgear assembly 810 according to the present disclosure. One side of the headgear assembly 810 is illustrated in FIGS. 11-14; however, the other side of the headgear assembly 810 can be a mirror image of the illustrated side or can be of another suitable arrangement. The headgear assembly 810 is configured to support a respiratory interface or mask M of any type in position on the head of a user. The headgear assembly 810 comprises a pair of hubs 850, a front strap 840, a top strap 820 and a rear strap 830. The front strap 840, top strap 820 and rear strap 830 comprise elongate and, preferably, inelastic straps that can be flexible in a thickness or height direction. For example, if the straps 820, 830, 840 are intramolded straps, the plastic core can be configured to permit flexibility in a height direction in at least a portion of the straps 820, 830, 840 to allow for adjustment of a spacing or angle between the top strap 820 and the rear strap 830. One or more of the straps 820, 830, 840 can be constructed as a single or integrated piece. In some configurations, at least the top strap 820 and rear strap 830 are constructed as a single piece.

The top strap 820 is configured to extend over the top of a user's head, in use, between the hubs 850 on each side of the headgear assembly 810. The rear strap 830 is configured to extend around the rear of a user's head, in use, between the hubs 850. The hubs 850 are configured to be positioned above and/or behind the user's ears. The hubs 850 can be made of a semi-rigid or rigid material. The connections between hubs 850 and straps 820 and 830 may be permanent or temporary. For example, as illustrated in FIGS. 12 and 14, the hubs 850 can comprise a slot or other opening 860 that permits the strap 820, 830, 840 to be inserted into and removed from an interior space of the hub 850. A width of the slot 860 can be slightly less than a width of the strap 820, 830, 840 to define retention features 870 that reduce or eliminate unintentional disconnection of the hub 850 from the strap 820, 830, 840. Other arrangements can also be used, such as a two piece (halves) or clamshell hub 850, for example.

The hubs 850 are configured to orient the straps 820, 830, 840 relative to one another. Preferably, a system or kit comprises multiple hubs 850 configured to fit the same straps 820, 830, 840 wherein the different hubs 850 provide different orientations to the straps 820, 830, 840. For example, the hub 850a (FIGS. 11 and 12) can orient the top strap 820 and the rear strap 830 at a greater spacing or angle relative to the spacing or angle provided by the hub 850b (FIGS. 13 and 14). Increasing the angle between the straps 820, 830 decreases the length of the loop formed by the headgear 810 and the mask M and thus the overall size of the headgear 810 can be adjusted to fit an individual user by swapping the interchangeable hub 850.

A system or kit can comprise two, three, four or more hubs 850, along with the straps 820, 830, 840 and, in some cases, the mask M, to provide different for different sizes (e.g., Small, Medium, Large, Extra-Large) of the headgear assembly 810. The system or kit can include two or more (e.g., all) of the available hubs 850 or a selected pair of the available hubs 850. Such an arrangement can provide an advantage that the single headgear strap arrangement reduces manufacturing costs and inventory. The single headgear strap arrangement can simplify setup and/or fitting for the user. In addition, in some configurations, a range of headgear sizes can be provided in a single mask packaging or kit.

Figure 16A:
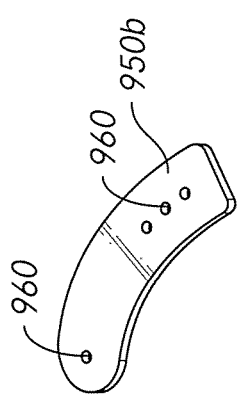
FIG. 16a is a side view of an alternative interchangeable hub for the headgear assembly of FIG. 15.
Figure 16B:
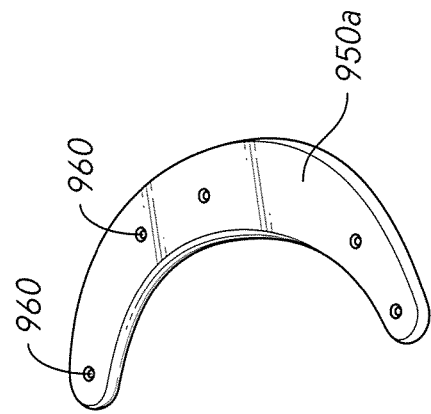
FIG. 16b is a side view of the interchangeable hub of FIG. 15.
Figure 15:
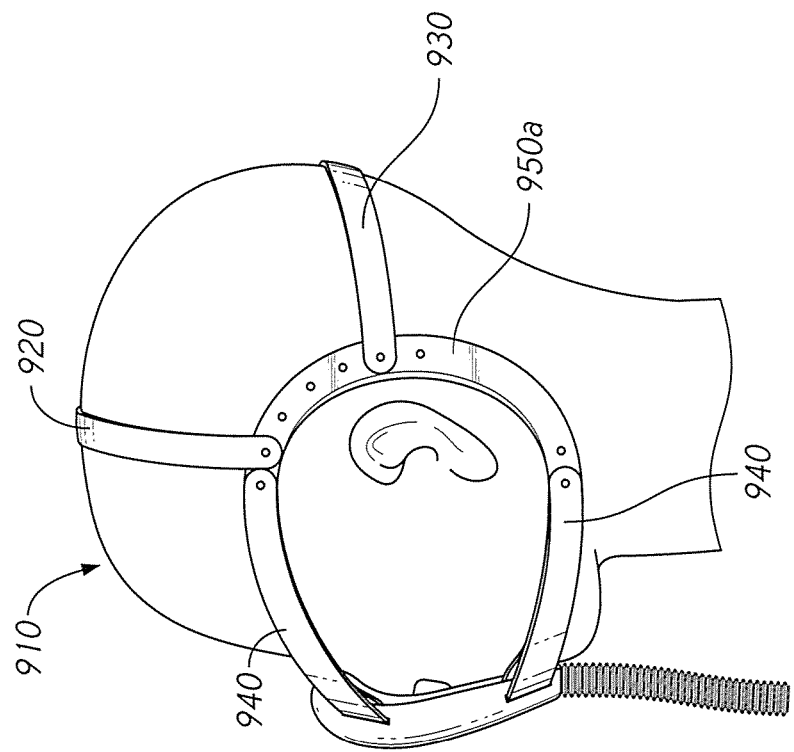
FIG. 15 is perspective view of a headgear assembly having another version of an interchangeable hub.

FIGS. 15, 16a and 16b illustrate a headgear arrangement 910 comprising multiple headgear straps, such as a top strap 920, a rear strap 930, one or more front straps 940 that can be coupled to a hub 950 on each side of the headgear arrangement 910. In some configurations, a plurality of types of hubs 950 can be provided in different sizes or configurations. For example, FIGS. 15 and 16b illustrate a first hub 950a that extends from a location above the user's U ear to a position below the user's U ear in use and is configured to be utilized with a full-face or oral-nasal mask M. FIG. 16a illustrates an alternative second hub 950b that is positioned above the user's U ear in use (e.g., in a position similar to the upper portion of the hub 950a in FIG. 15) and is configured to be utilized with a nasal mask M (e.g., a nasal or direct nasal mask). The second hub 950b can allow the use or one or more front straps 940 or strap portions with each hub 950*b* on each side of the headgear arrangement 910. Other optional hubs 950 can also be provided.

In addition or in the alternative, the headgear arrangement 910 can comprise different lengths of one or more of the straps 920, 930, 940 such that an overall size of the headgear arrangement 910 can be adjusted to suit an individual user U. Each hub 950 can comprise multiple headgear connection points 960 to allow further customization of the placement and relative positions of the straps 920, 930, 940. As with other arrangements disclosed herein, the different length of straps 920, 930, 940 and/or types of headgear connector hubs 950 can be made available as part of a system or can be provided together in a kit that provides sizing and/or type options for a user U of the kit.

In use, an appropriate hub style (e.g., 950*a*, 950*b*) is chosen depending on the type of mask interface M that is to be used. Straps 920, 930, 940 are connected between two of the hubs 950 and the mask interface M to form a top/crown strap 920, a rear strap 930 and front straps 940 as appropriate. As described above, the straps 920, 930, 940 may be provided in a single size for each strap location (i.e. top, rear, side, front, etc.) or alternatively the straps may be provided in a range of lengths that can be used as any of the strap types. As described above, in some configurations, the straps 920, 930, 940 can be intramolded and can include connectors at each end to connect to the interchangeable hub 950.

As described above, preferably, the interchangeable hubs 950 have different shapes and connection points 960 depending, for example, on the type of mask M with which the headgear assembly 910 is to be used. For example, a full-face mask M (FIG. 15) typically requires a lower (under ear) force vector to be applied to the mask M by the headgear assembly 910 in order to seal the mask M with the face of the user U. Therefore, a full-face interchangeable hub 950*a* can be configured to pass around the rear of a user's U ear such that front straps 940 can be connected both above and below the ears. An interchangeable hub 950*b* configured for use with a nasal or direct nasal (e.g., pillows) mask M may only extend above the ear.

FIGS. 17 and 18*a*-18*c* illustrate another headgear assembly 910 that is similar to the headgear assembly 910 of FIGS. 15, 16*a* and 16*b*. Accordingly, the same reference characters are used to refer to corresponding or similar components or features. The headgear assembly 910 of FIGS. 17 and 18*a*-18*c* comprises multiple headgear straps, such as a top strap 920, a rear strap 930, one or more front straps 940 that can be coupled to one of several types of hubs 950*a* (FIG. 18*a*), 950*b* (FIGS. 18*b*) and 950*c* (FIG. 18*c*) on each side of the headgear arrangement 910. Each hub 950*a*, 950*b*, 950*c* can comprise at least one strap connection point 960 for each strap 920, 930, 940 that is intended for use with the hub 950*a*, 950*b*, 950*c*.

Figure 18A:
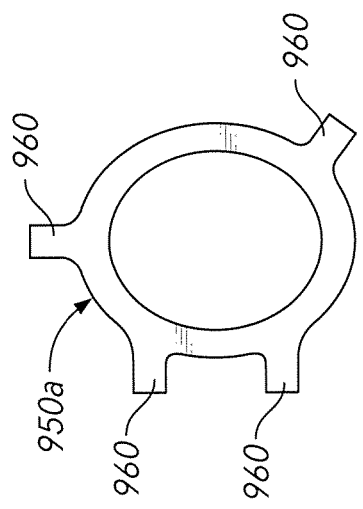
FIG. 18a is a side view of a first hub configured for use with the headgear assembly of FIG. 17.

The hubs 950*a*, 950*b*, 950*c* can be configured for use with different types of masks M. For example, the hub 950*a* of FIG. 18*a* is configured for use with a full face mask M and includes upper and lower connection points 960 for front straps 940 in addition to connection points for a top strap 920 and a rear strap 930. In the illustrated arrangement, the hub 950*a* defines an ear loop that surrounds the user's U ear; however, in other configurations the hub 950*a* may only partially surround the ear.

Figure 18B:
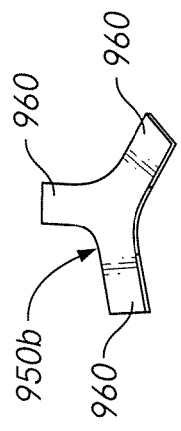
FIG. 18b is a side view of a second hub configured for use with the headgear assembly of FIG. 17.

The hub 950*b* of FIG. 18*b* is configured for use with a direct nasal or pillows mask M. The hub 950*b* can be substantially smaller than the hub 950*a* and can be configured to be positioned above the user's U ear in use. The hub 950*b* can define a single connection point 960 for a single front strap 940 (on each side of the headgear arrangement 910). The connection point 960 for the front strap 940 can be located relatively higher than the upper connection point 960 for the upper front strap 960 in FIG. 18*a* to provide a more upward force vector on the direct nasal mask M.

Figure 18C:
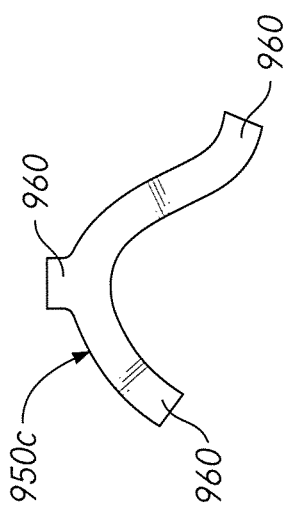
FIG. 18c is a side view of a third hub configured for use with the headgear assembly of FIG. 17.
Figure 17:
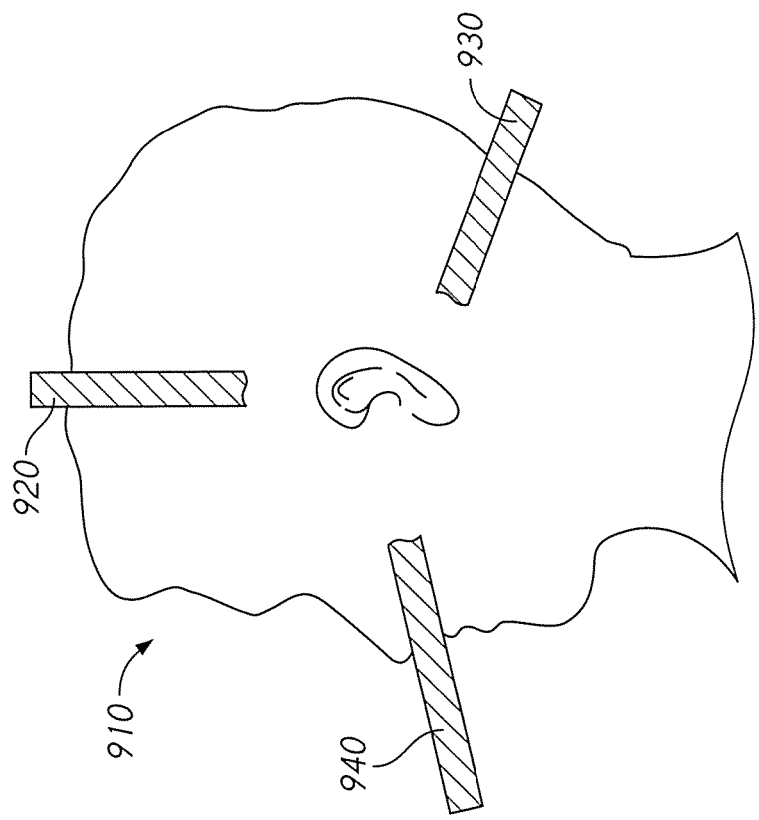
FIG. 17 is a side view of a portion of a headgear assembly configured to accept a plurality of interchangeable hubs.

The hub 950*c* of FIG. 18*c* can be configured for use with a nasal mask M, such as a non-direct nasal mask M. The illustrated hub 950*c* does not completely encircle the ear of the user U, but can be otherwise shaped or configured to locate the front strap 940, the top strap 920 and the rear strap 930 in a similar position to the upper front strap 940, the top strap 920 and the rear strap 930 in the hub 950*a* of FIG. 18*a*. That is, in some configurations, the hub 950*c* is sized and shaped similar to the hub 950*a*, but omits the lower forward portion of the hub 950*a*.

In some configurations, the front straps 940 (or other straps 930, 940) could incorporate a length adjustment arrangement, which can incorporated a directional lock (e.g., a one-way friction mechanism). Examples of such an arrangement are disclosed in Applicant's U.S. Publication Nos. US2016/0082217 entitled AUTOMATICALLY ADJUSTING HEADGEAR FOR PATIENT INTERFACE and US2016/0144146 entitled HEADGEAR ASSEMBLIES AND INTERFACE ASSEMBLIES WITH HEADGEAR, the entireties of which are hereby incorporated by reference herein and made a part of the present disclosure.

In some configurations, the headgear arrangements 910 can provide the advantage of a single range or system of headgear components that can be used for a range of masks M (e.g., different sizes and/or types of masks), which can reduces manufacturing costs. In addition, the illustrated headgear arrangement 910 could be useful in a hospital setting where the headgear is disposable, as the headgear can be assembled to suit each individual user U. In some configurations, a range of headgear sizes can be provided in a single mask packaging.

FIGS. 19-21 illustrate a headgear assembly 1010 configured to provide for simple and convenient size adjustment. The headgear assembly 1010 is configured to hold a mask M on the face of a user and, in the illustrated configuration, includes a top strap 1020, a rear strap 1030 and at least one front strap 1040. Two or more (e.g., three, four or more) spacer elements 1050 can be provided, each of which is configured for insertion within one or more of the straps 1020, 1030, 1040. A selected one of the available spacer elements 1050 can be inserted within the strap 1020, 1030, 1040 to fit the headgear assembly 1010 to a particular user.

In some configurations, the headgear assembly 1010 includes at least three spacer elements 1050*a*, 1050*b*, 1050*c*, as illustrated in FIG. 20. The spacer elements 1050*a*, 1050*b*, 1050*c* can be configured to correspond to small, medium and large configurations of the headgear assembly 1010, for example. Additional sizes of spacer elements 1050*a*, 1050*b*, 1050*c* can also be provided. Although illustrated in the top strap 1020, the spacer elements 1050*a*, 1050*b*, 1050*c* could also or alternatively be configured for insertion in any of the straps 1020, 1030, 1040. In addition, although illustrated in an intermediate portion (e.g., a center) of the strap 1020, the spacer elements 1050*a*, 1050*b*, 1050*c* could be configured for placement elsewhere within any one of the straps 1020, 1030, 1040 or at an intersection of two or more straps 1020, 1030, 1040.

The spacer elements 1050*a*, 1050*b*, 1050*c* can be configured to connect with the straps 1020, 1030, 1040 in any suitable manner. For example, in the illustrated arrangement, the spacer element 1050*a*, 1050*b*, 1050*c* is configured to be received within a receptacle or pocket 1068 (FIG. 21) in each portion of the strap(s) 1020, 1030, 1040. The strap

1020, 1030, 1040 can be secured within the pocket 1068 by a friction fit or by a suitable locking arrangement, if desired.

FIG. 22 illustrates an alternative headgear assembly 1010 that is similar to the headgear assembly 1010 of FIGS. 19-21. Accordingly, the same reference characters are used to indicate corresponding or similar components or features. The headgear assembly 1010 is illustrates a plurality of spacer elements 1050*a*, 1050*b*, 1050*c* configured for insertion within the rear strap 1030 of the headgear assembly 1010. In addition, the illustrated arrangement includes an interlocking connection between the strap 1030 and the spacer elements 1050*a*, 1050*b*, 1050*c*. In particular, the illustrate ends of the separated portions 1030*a*, 1030*b* of the rear strap 1030 include hook-type posts 1070 that are configured to engage complementary receptacles or pockets (not shown) in the spacer elements 1050*a*, 1050*b*, 1050*c*. The hook-type posts 1070 can include interlocking surfaces that engage corresponding interlocking surfaces of the receptacles in the spacer elements 1050*a*, 1050*b*, 1050*c* to inhibit undesired separation of the strap portion 1030*a*, 1030*b* and the spacer elements 1050*a*, 1050*b*, 1050*c*. However, preferably, manual force can overcome the locking force of the interlocking connection to allow deliberate separation of the strap portion 1030*a*, 1030*b* and the spacer elements 1050*a*, 1050*b*, 1050*c*.

Figure 24:
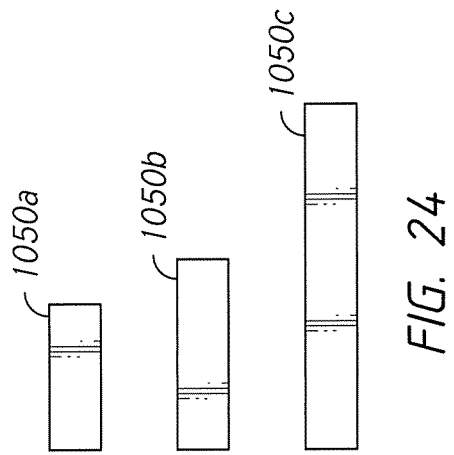
FIG. 24 illustrates top views of several interchangeable spacer elements configured for use with the headgear assembly of FIG. 23.
Figure 23:
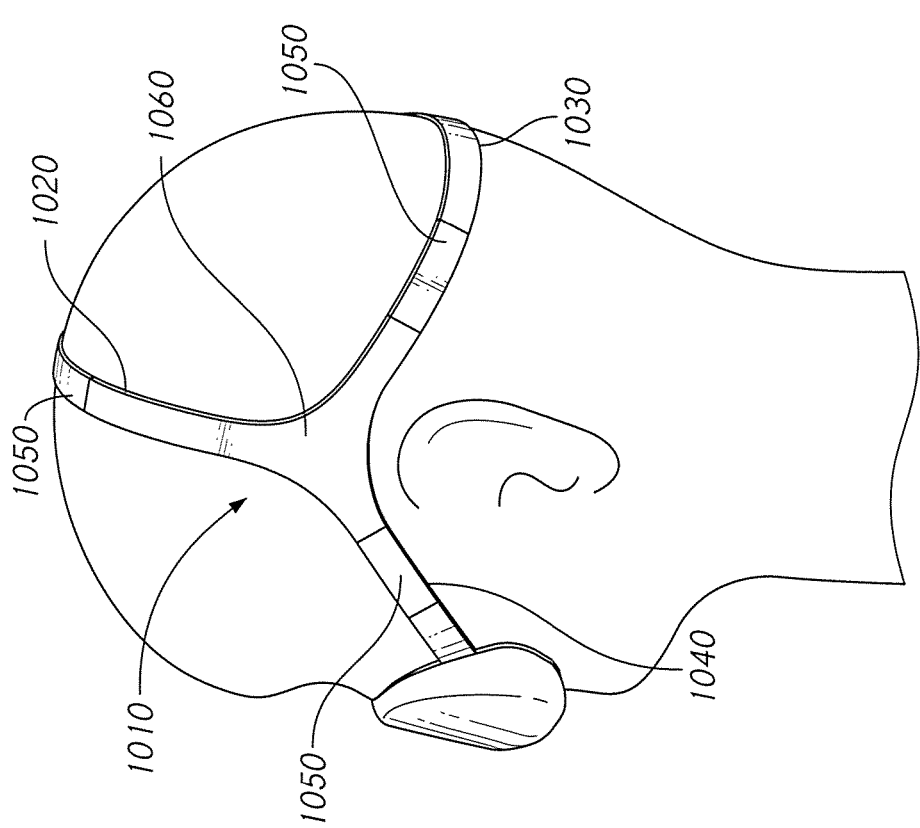
FIG. 23 is a perspective view of a headgear assembly configured to include interchangeable spacer elements in multiple straps of the headgear assembly.

FIGS. 23 and 24 illustrate another alternative headgear assembly 1010 that is similar to the headgear assemblies 1010 of FIGS. 19-22. Accordingly, the same reference characters are used to indicate corresponding or similar components or features. The headgear assembly 1010 of FIGS. 23 and 24 illustrates a plurality of spacer elements 1050*a*, 1050*b*, 1050*c* configured for insertion within one or all of the straps 1020, 1030, 1040 of the headgear assembly 1010. The spacer elements 1050*a*, 1050*b*, 1050*c* can be configured for one time or permanent connection to the strap 1020, 1030, 1040. Any suitable arrangement can be used, such as a permanent or destructible interlocking arrangement. In the illustrated arrangement, the headgear assembly 1010 comprises a side hub 1060 on each side that forms a portion of and interconnects the straps 1020, 1030, 1040. In addition, in some configurations, the straps 1020, 1030, 1040 can include a spacer element 1050*a*, 1050*b*, 1050*c* on each side of the headgear assembly 1010.

Figure 25:
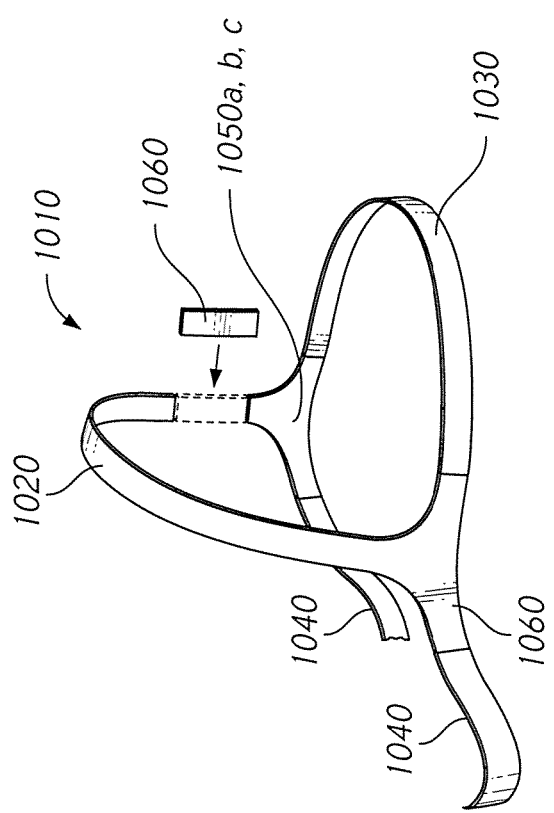
FIG. 25 is a perspective view of a headgear assembly configured to incorporate one of a plurality of spacer elements at an end of a strap of the headgear assembly.

FIG. 25 illustrates another alternative headgear assembly 1010 that is similar to the headgear assemblies 1010 of FIGS. 19-24. Accordingly, the same reference characters are used to indicate corresponding or similar components or features. The headgear assembly 1010 of FIG. 25 comprises a plurality of spacer elements 1050*a*, 1050*b*, 1050*c* having different lengths configured for insertion at the end of one or all of the straps 1020, 1030, 1040 of the headgear assembly 1010. In the illustrated arrangement, one of the available spacer elements 1050*a*, 1050*b*, 1050*c* is illustrated connecting the top strap 1020 to a side hub 1060. However, the spacer elements 1050*a*, 1050*b*, 1050*c* can be configured for insertion between any one of the straps 1020, 1030, 1040 and the side hubs 1060 or between any two straps 1020, 1030, 1040. A removable or permanent connection can be utilized.

In some configurations of the headgear assemblies 1010 of FIGS. 19-25, any one or more of the straps 1020, 1030, 1040 may be formed in two halves. That is, any one of the straps 1020, 1030, 1040 can have a left half and a right half. In some configurations, at least one of the straps 1020, 1030, 1040 can be formed as part of a side hub 1060. The spacer element 1050*a*, 1050*b*, 1050*c* acts as a connector and extender for the headgear straps 1020, 1030, 1040. The length of the straps 1020, 1030, 1040 and, therefore, the size of the headgear assembly 1010 can be altered by selecting a different size spacer element 1050*a*, 1050*b*, 1050*c*. The spacer elements 1050*a*, 1050*b*, 1050*c* can include receiving portions at each end that are configured to receive and retain the ends of the strap 1020, 1030, 1040 (see, reference number 1068 in FIG. 21). Alternatively, the ends of the strap 1020, 1030, 1040 may include retaining portions that receive the ends of the spacer elements 1050*a*, 1050*b*, 1050*c*. As described above, the receiving portions may provide a one-time/permanent connection between the straps 1050*a*, 1050*b*, 1050*c*, spacer element 1050*a*, 1050*b*, 1050*c* or hub 1060, or alternatively it may be possibly to repeatedly connect and disconnect the straps 1050*a*, 1050*b*, 1050*c*, spacer element 1050*a*, 1050*b*, 1050*c* or hub 1060. In some configurations, the spacer element 1050*a*, 1050*b*, 1050*c* can be made from a flexible plastic, such that it can conform to the curvature of the user's U head. In some configurations, the headgear assembly 1010 can have the advantage of fewer components to reduce manufacturing steps and cost. In addition, fewer components can also reduce the time it takes to assemble and fit the headgear assembly 1010 and mask M to a user U.

FIGS. 26 and 27 illustrate a headgear assembly 1110 having a headgear structure including one or more of a top strap 1120, rear strap 1130 and a front strap 1140. The headgear assembly 1110 also includes a spacer element 1150 that is configured to be coupled to the headgear structure. The spacer element 1150 along with the headgear structure (and, in some cases, the mask M) forms a closed loop. The spacer element 1150 can be created for a specific user U in a specific size (e.g., length) to create a desired circumference or length of the closed loop. For example, the spacer element 1150 can be custom made (e.g., 3D printed) after the user's U necessary or desired closed loop length is determined, taking into account the standard length of the headgear structure (and, in some cases, the mask M).

In some configurations, the combination of any one or more of the straps 1120, 1130, 1140 are formed as a unitary structure. Suitable connectors, such as any of those disclosed herein, can be provided at the ends of straps 1120, 1130, 1140 to connect to the spacer element 1150. The custom length of the spacer element 1150 can be based on user's U head circumference or other anatomic measurement. With reference to FIG. 27, the spacer element 1150 can have standard or custom information, such as the user's U name or other identification, brand or model (or other identifying) information of the headgear assembly 1110 and sizing information, such as the user's U head circumference or the spacer element 1150 length printed or embossed on the spacer element 1150.

FIGS. 28 and 29 illustrate a headgear assembly 1210 having a top strap 1220, a rear strap 1230 and at least one front strap 1240. The headgear assembly 1210 holds a mask M in place on the head of a user U. The headgear assembly 1210 comprises a plurality of spacer elements 1250 inserted within one of or between two of the straps 1220, 1230, 1240 of the headgear assembly 1210. In some configurations, the spacer elements 1250 are provided in several sizes or lengths to allow the size of the headgear arrangement 1210 to be adjusted.

With reference to FIG. 29, the headgear assembly 1210 can be configured such that the connection between the straps 1220, 1230, 1240 and the spacer element 1250 is a one-way connection or permanent connection. In the illustrated arrangement, the spacer element 1250 is a hollow or tubular structure that has an internal corrugated surface 1270 defining an interior space. The straps 1220, 1230, 1240 include connector ends 1280, each of which comprises a plurality of teeth 1282 configured to engage with corrugated surface 1270. In some configurations, the teeth 1282 are flat or sharply angled on one side to resist removal of the connector end 1280 from the spacer element 1250 and the teeth 1282 are tapered on an opposing side to aid insertion into the spacer element 1250. This arrangement could be reversed so that the straps 1220, 1230, 1240 have a recess at one end that receives a connector end 1280 of the spacer element 1250. In the illustrated arrangement, the straps 1220, 1230, 1240 are joined together by different length spacer elements 1250. The connection is permanent so that once fitted to the user U, the size of the headgear assembly 1210 is fixed and the user U does not have to size the headgear assembly 1210 again.

Figure 31:
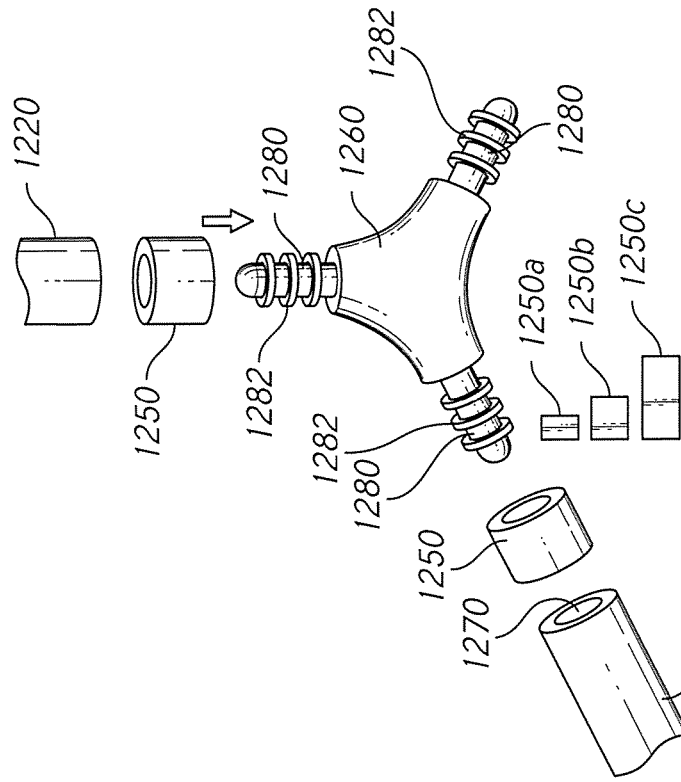
FIG. 31 illustrates a connection between the straps, spacer elements and the strap connector hub of the headgear assembly of FIG. 30.
Figure 30:
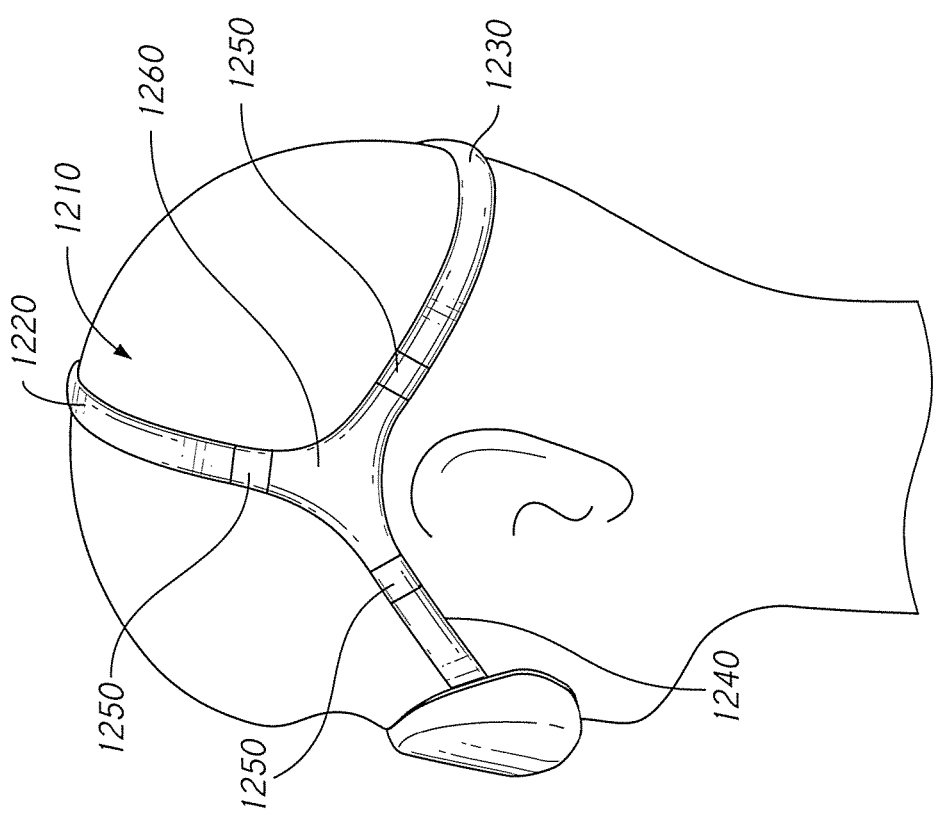
FIG. 30 is a perspective view of a headgear assembly configured to incorporate an interchangeable spacer element between a strap connector hub and one or more straps of the headgear assembly.

FIGS. 30 and 31 illustrate a headgear assembly 1210 that is similar to the headgear assembly 1210 of FIGS. 28 and 29. Accordingly, the same reference characters are used to indicate corresponding or similar components or features. The headgear assembly 1210 of FIGS. 30 and 31 includes, in some configurations, an interchangeable hub 1260 that forms a portion of or interconnects the top strap 1220, rear strap 1230 or front strap 1240. Several versions of the hub 1260 can be provided to, for example, accommodate different types of masks M (e.g., nasal, direct nasal or pillows or full face masks).

The illustrated hub 1260 includes a connector insert 1280 for each strap 1220, 1230, 1240. The headgear assembly 1210 also includes a plurality of spacer elements 1250, which may be provided in different lengths (e.g., small 1250*a*, medium 1250*b* and large 1250*c*). Each of the connector inserts 1280 preferably has a length that is greater than a length of the longest of the spacer elements 1250. Accordingly, a selected spacer element 1250 can be positioned between the strap 1220, 1230, 1240 and the hub 1260. The strap 1220, 1230, 1240 can be connected to the connector insert 1280 after the selected spacer element 1250 is positioned on the hub 1260. Thus, a spacer element 1250 can be selected to alter a length of the strap 1220, 1230, 1240 and, therefore, a size of the headgear assembly 1210.

In the illustrated arrangement, the straps 1220, 1230, 1240 and/or spacer elements 1250 are configured to be repeatedly or reversibly connectable to the hub 1260. Any suitable reversible connection can be used. In the illustrated arrangement, each of the connector inserts 1280 comprises a plurality of flanges 1282 configured to engage a surface 1270 defining an interior space of the strap 1220, 1230, 1240. The flanges 1282 can also engage an interior surface of the spacer elements 1250. The flanges 1282 can be relatively rigid or flexible. The illustrated arrangement could also be reversed.

In the illustrated arrangement, the spacer elements 1250 are hollow or tubular and configured to fit over the connector inserts 1280. The spacer elements 1250 can be positioned in between the hub 1260 and the straps 1220, 1230, 1240 and can restrict the amount of strap 1220, 1230, 1240 that can fit onto the connector inserts 1280 of the hubs 1260. The spacer elements 1250 can be available in a range of lengths to determine the length of the headgear straps 1220, 1230, 1240. The straps 1220, 1230, 1240 can have a connector end configured to engage the connector inserts 1280. For example, the connector ends of the straps 1220, 1230, 1240 can have an interior surface 1270 that defines an interior space configured to receive the connector insert 1280. In some configurations, at least the connector ends of the straps 1220, 1230, 1240 are flexible or elastic to stretch over and engage with the flanges 1282 of the connector inserts 1280.

In use, the straps 1220, 1230, 1240 are fitted over the connector inserts 1280 of the interchangeable hub 1260. The spacer elements 1250 fit over the connector inserts 1280 between the connector ends of the straps 1220, 1230, 1240 and the centre of the hub 1260. The length of the selected spacer elements 1250 determine how much of the strap 1220, 1230, 1240 is connected to the connector inserts 1280 of the interchangeable hubs 1260. The flanges 1282 on the connector inserts 1280 engage with the internal surface 1270 of the straps 1220, 1230, 1240 and resist removal so that the size of the headgear 1210 does not change unintentionally. In some configurations, the flanges 1282 (or whole interchangeable hub 1260) can be made of an elastomeric material such that the friction between the flanges 1282 and the straps 1220, 1230, 1240 is increased. The connection between the straps 1220, 1230, 1240 and the interchangeable hubs 1260 can be permanent or removable. In some configurations, the illustrated connection arrangement could be used without the spacer elements 1250 to join straps 1220, 1230, 1240 to interchangeable hubs 1260.

FIGS. 32-34 illustrate a headgear assembly 1310 having a top strap 1320, a rear strap 1330 and at least one front strap 1340. The headgear assembly 1310 holds a mask M in place on the head of a user U. The headgear assembly 1310 comprises a plurality of spacer elements 1350 inserted within one of or between two of the straps 1320, 1330, 1340 of the headgear assembly 1310. In some configurations, the spacer elements 1350 are configured to secure the straps 1320, 1330, 1340 in one of a plurality of possible positions relative to the spacer element 1350 to alter a length of the strap 1320, 1330, 1340 and, thus, a size of the headgear assembly 1310.

In particular, each end of the strap 1320, 1330, 1340 or a portion thereof configured to connect to the spacer element 1350 comprises a connector insert 1380 in the form of a flat strap having a corrugated surface 1382. Each spacer element 1350 includes a lock arrangement 1390 on each end configured to selectively engage the connector insert 1380 of a strap 1320, 1330, 1340. The lock arrangement 1390 can be actuated by a user-accessible push button 1392. The lock arrangement 1390 on one end of a spacer element 1350 is illustrated in FIG. 34. The lock arrangement 1390 of the other end can be the same or similar.

With reference to FIG. 34, the spacer element 1350 includes an interior space that accommodates the lock arrangement 1390 and the connector insert 1380 of the strap 1320, 1330, 1340. The spacer element 1350 includes a positioning structure 1370 configured to locate and support the connector insert 1380 within the interior space of the spacer element 1350. The push button 1392 of the lock arrangement 1390 defines an interior passage 1394 having a corrugated surface 1396 configured to engage the corrugated surface 1382 of the connector insert 1380.

A biasing element 1398 is configured to bias the push button 1392 into a locked position in which the corrugated surfaces 1382, 1396 are engaged and the strap 1320, 1330, 1340 is secured in a selected adjustment position relative to the spacer element 1350. The biasing element 1398 can be of any suitable arrangement, such as a spring. In the illustrated arrangement, the biasing element 1398 is unitarily-formed with a body of the spacer element 1350.

The interior passage 1394 is sized such that the connector insert 1380 can move away from the corrugated surface 1396 into a released position in which relative movement of the connector insert 1380 and the push button 1392 is permitted. A head 1393 of the push button 1392 is exposed so that a user can move the push button 1392 against the biasing force of the biasing element 1398 to release the connector insert 1380 and, thus, the strap 1320, 1330, 1340. With such an arrangement, the user U can select a position of the straps 1320, 1330, 1340 relative to the spacer element 1350 to adjust a length of the strap 1320, 1330, 1340 and, therefore, a size of the headgear assembly 1310.

In the illustrated arrangement, the connector insert 1380 and the push button 1392 include the corrugated surfaces 1382, 1396, respectively, on only one side. However, in some configurations, the corrugated surfaces 1382, 1396 are provided on at least one side and can be provided on multiple sides (e.g., opposing sides and/or adjacent sides). The spacer element 1350 preferably is hollow or tubular at least at the ends, but can be hollow along its entire length.

In use, the connector inserts 1380 of straps 1320, 1330, 1340 are pushed into the ends of the spacer element 1350. The corrugated surfaces 1382, 1396 of the connector insert 1380 and the push button 1392, respectively, engage one another in a ratchet manner during insertion. The push button 1392 can be pushed down to disengage the corrugated surfaces 1382, 1396 allowing the strap 1320, 1330, 1340 to be removed from the spacer element 1350. The biasing element 1398 supports the push button 1392 in an engaged position, where the head 1393 is raised from an outer surface of the spacer element 1350 and the corrugated surface 1396 of the push button 1392 is engaged with the corrugated surface 1382 of the connector insert 1380 so that the straps 1320, 1330, 1340 stay joined to the spacer elements 1350. The corrugated surfaces 1382, 1396 allow the connector insert 1380 to be engaged with the spacer element 1350 at a different length to alter the size of the headgear assembly 1310 and/or the spacer elements 1350 can be provided in a range of sizes. In some configurations, such an arrangement provides straps 1320, 1330, 1340 and spacer elements 1350 that are easy to connect and disconnect. In addition, the components (e.g., straps 1320, 1330, 1340 and spacers 1350) are reusable and/or replaceable.

Figure 36:
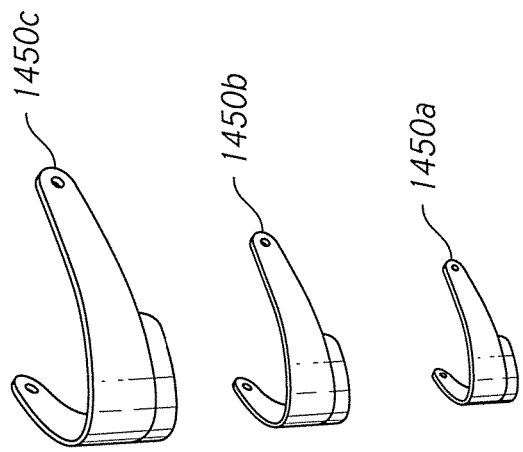
FIG. 36 illustrates several interchangeable mask frames configured for use with the headgear assembly of FIG. 35.
Figure 35:
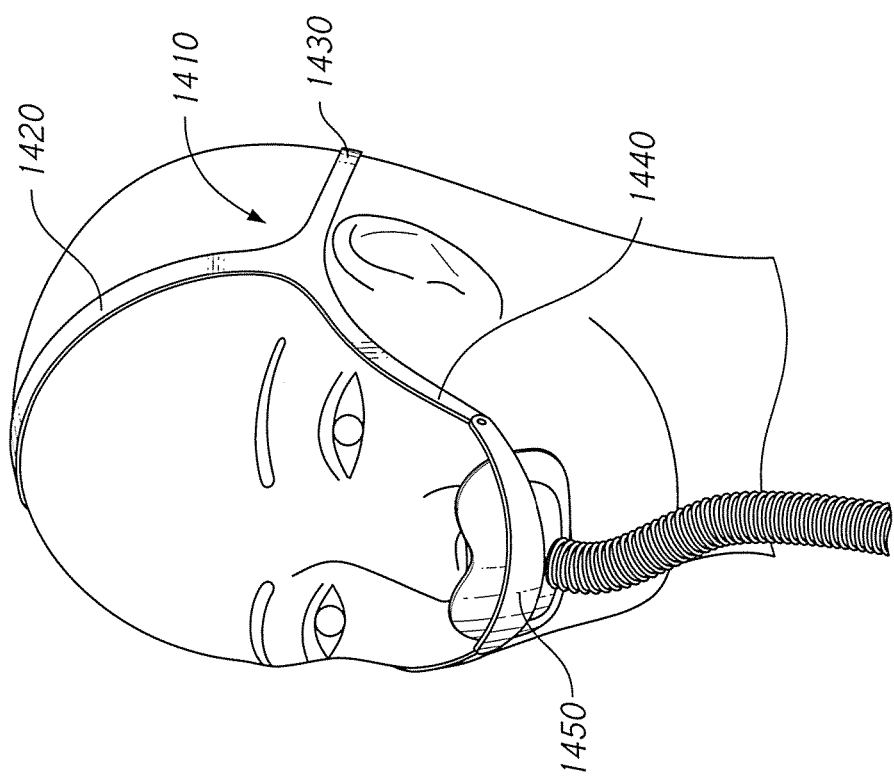
FIG. 35 is a perspective view of a headgear assembly configured to incorporate one of a plurality of interchangeable mask frames.

FIGS. 35 and 36 illustrate a headgear assembly 1410 having a top strap 1420, a rear strap 1430 and at least one front strap 1440. The headgear assembly 1410 holds a mask M in place on the head of a user U. The headgear assembly 1410 comprises a plurality of different sized spacer elements in the form of mask frames 1450. A selected mask frame 1450 can be utilized to secure the remaining headgear structure (e.g., the top strap 1420, the rear strap 1430 and the front strap 1440) to the mask M. In the illustrated arrangement, the mask frame 1450 is within the front strap 1440 or between the front straps 1440 on opposite sides of the headgear assembly 1410. The mask frame 1450 can be provided in different lengths (e.g., small 1450a, medium 1450b and large 1450c) to allow adjustment of a size of the headgear assembly 1410.

In some configurations, the assembly of the headgear 1410 and mask M includes a bifurcated headgear structure having a rear strap 1430, a top strap 1420 and a pair of front straps 1440. The headgear 1410 can be made from intramolded plastic and can be substantially inelastic. In some configurations, the headgear 1410 can be formed in a 3D structure, such as having a self-sustaining three-dimensional shape in which one side of the headgear assembly 1410 remains spaced apart from the other side of the headgear assembly 1410 in the absence of significant external forces. In some configurations, the headgear assembly 1410, apart from the mask frame 1450, has no adjustability and can be provided in a single size (or range of set sizes) for all users U.

The mask frame 1450 can include elongate arms portions that extend rearward towards the user's U cheeks. The length of the arms varies between frame sizes. In some configurations, the mask frame 1450 is designed as a universal connector configured to connect to all mask M seal sizes within a particular family of masks M, such as direct nasal, nasal and full face masks, for example. Such an arrangement can allow for fewer components to reduce manufacturing steps and cost. Fewer components also reduces the time it takes to assemble and fit the headgear 1410 and mask M to a user U. In some configurations, the headgear 1410 can remain on the user's U head whilst the frame 1450 is swapped in or out to achieve the correct sizing. In some configurations, the headgear assembly 1410 allows for easier access for a therapist, nurse or other caregiver to change the sizing, such as in a sleep lab or hospital environment. For example, the mask frame 1450 can be swapped whilst user U is reclined.

Figure 38:
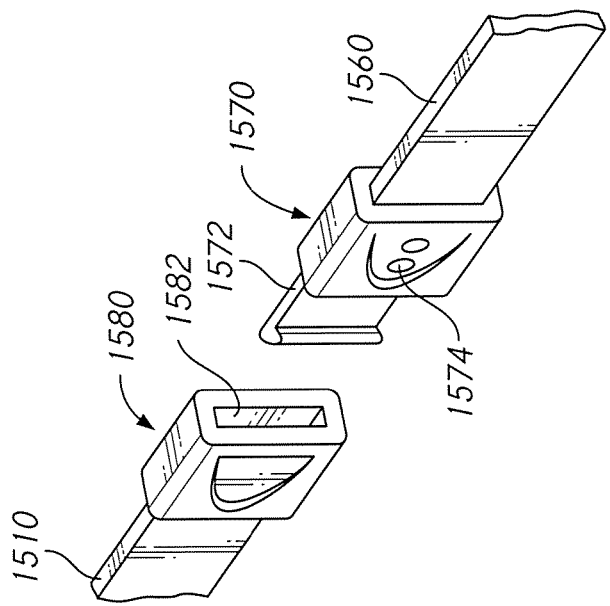
FIG. 38 illustrates a connection between the rear headgear portion and a mask frame of the headgear assembly of FIG. 37.
Figure 37:
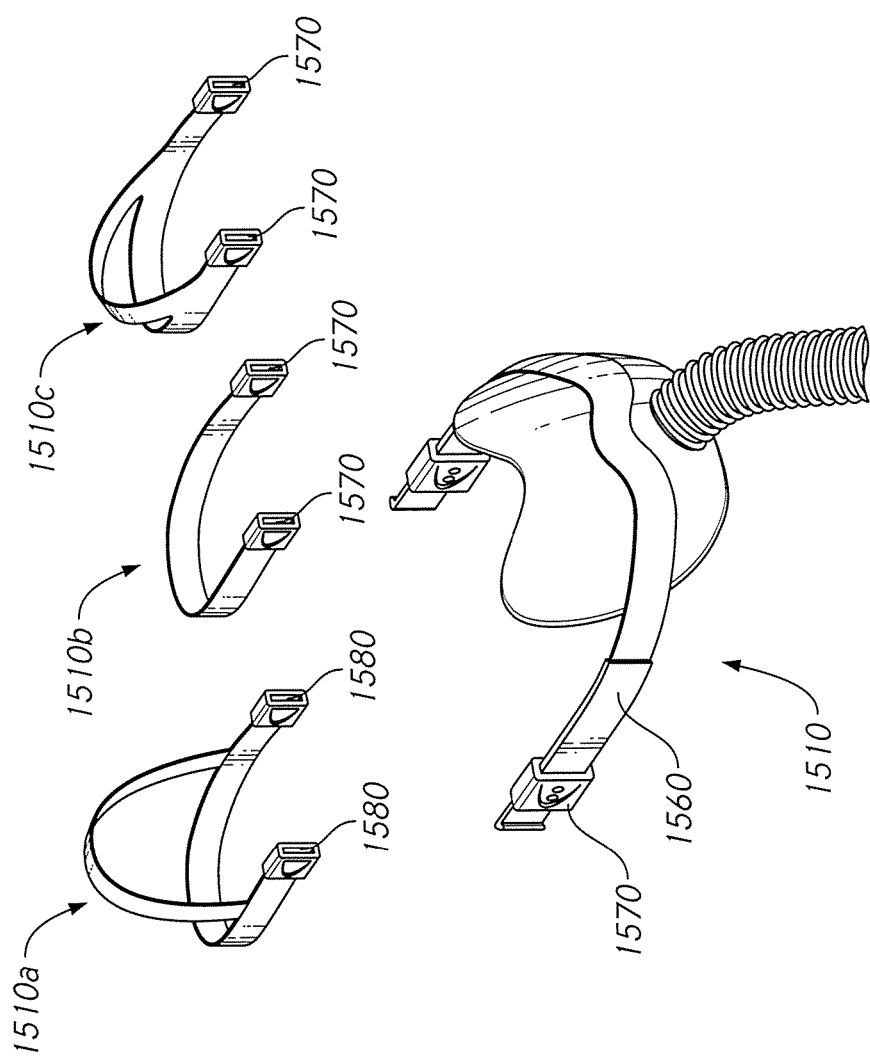
FIG. 37 is a perspective view of a headgear assembly configured to incorporate one of several interchangeable rear headgear portions.

FIGS. 37 and 38 illustrate system or kit having a plurality of headgear assemblies 1510a, 1510b, 1510c, each of which is configured to hold a mask M in place on the head of a user U. The illustrated mask M includes a connection portion, such as a frame 1560, which is configured to secure the mask M to the headgear assembly 1510a, 1510b, 1510c. The frame 1560 can be removably or permanently connected to the mask M. The headgear assemblies 1510a, 1510b, 1510c can have different sizes and/or shapes or configurations (e.g., single strap or bifurcated) so that the user U can select a desired headgear assembly 1510 from the available selection of headgear assemblies 1510a, 1510b, 1510c. Although three headgear assemblies 1510a, 1510b, 1510c are illustrated, any number of suitable headgear types or sizes can be provided.

Preferably, the connection between the frame 1560 of the mask M and the various headgear assemblies 1510a, 1510b, 1510c is universal among the available headgear assemblies 1510 such that the user U can select any one of the available headgear assemblies 1510. Any suitable connection mechanism can be used. For example, the headgear assembly 1510 and the frame 1560 are coupled by one or more interconnecting clip arrangements, each of which comprises a first clip member 1570 on the frame 1560 and a second clip member 1580 on the headgear assembly 1510. The illustrated first clip member 1570 includes a locking element or latch 1572 configured to be received within a cavity or receptacle 1582 of the second clip member 1570. The latch 1572 is configured to engage the second clip member 1580 and can be released by an actuator 1574 on the first clip member 1570. However, other suitable types of releasable connectors could also be used.

In some configurations, one or more of the headgear assemblies 1510 can include an adjustment mechanism to automatically adjust sizing, as described above. In some configurations, the combination of the mask M, the frame 1560 and the headgear assemblies 1510a, 1510b, 1510c provide the advantage of allowing a user U to choose the most appropriate headgear 1510a, 1510b, 1510c for them independent of the type of mask M. In some configurations, such as those involving multiple available sizes of headgear 1510, no adjustment of the headgear assembly 1510 is required. In many configurations, the mask M, the frame 1560 and the headgear assemblies 1510a, 1510b, 1510c are easy to assemble.

Figure 40:
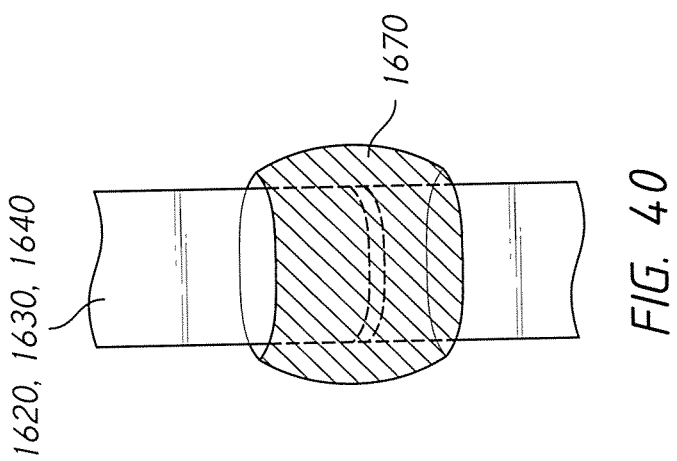
FIG. 40 illustrates a connection between a strap and the connector hub.
Figure 39:
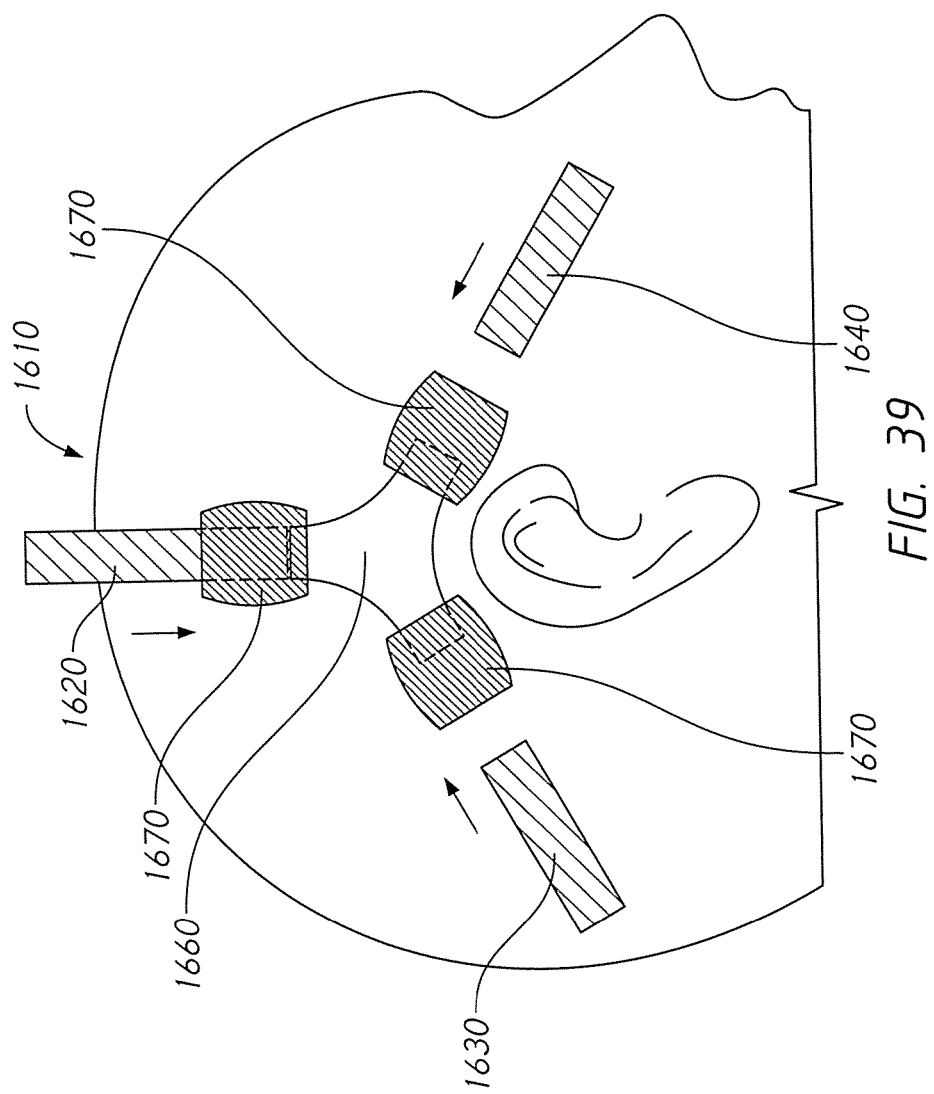
FIG. 39 is a perspective view of a headgear assembly configured to incorporate a strap connector hub on each side of the headgear assembly that connects straps of the headgear assembly. One or both of the connector hubs and straps can be provided in multiple lengths.

FIGS. 39 and 40 illustrate a headgear assembly 1610 having one or more straps that is permanently connectable to one another or another headgear component. In particular, the illustrated headgear assembly 1610 includes a plurality of straps, such as a top strap 1620, a rear strap 1630 and at least one front strap 1640. The headgear assembly 1610 holds a mask in place on the head of a user U. In the illustrated arrangement, the headgear assembly 1610 comprises at least one hub 1660 that interconnects the straps 1620, 1630, 1640 and can include a hub 1660 on each side of the headgear assembly 1610. Either one or both of the hub 1660 and the straps 1620, 1630, 1640 can be provided in multiple sizes (e.g., lengths) to allow adjustment of the size of the headgear assembly 1610. Alternatively, the straps 1620, 1630, 1640 can be provided in a single length that can be trimmed to size. The hub 1660 and the straps 1620, 1630, 1640 can be joined in a permanent fashion by a connector 1670, which can be a thermoplastic heat shrink tubing, for example. The connector 1670 can receive an end portion of each of the hub 1660 and the straps 1620, 1630, 1640 and can then be shrunk in size to join the components. In some configurations, the connector 1670 can be a molded component, which can be overmolded in some configurations. However, other suitable permanent connectors or connection arrangements can be used.

FIGS. 41-43 illustrate a headgear assembly 1710 having a plurality of straps that are interconnected by a component, which allows for adjustment of a position of the strap relative to the component. In particular, the illustrated headgear assembly 1710 includes a top strap 1720, a rear strap 1730 and at least one front strap 1740. The headgear assembly 1710 holds a mask M in place on the head of a user U. The headgear assembly 1710 comprises a strap connector hub 1760 that interconnects two or more of the straps 1720, 1730, 1740. The hub 1760 is configured to support one of a plurality of available inserts in the form of strap connector or spacer elements 1750. Each of the strap spacer elements 1750 is configured to position the straps 1720, 1730, 1740 at different locations relative to the hub 1760. A selected strap spacer element 1750 can be utilized to secure the straps 1720, 1730, 1740 at a selected location relative to the hub 1760 to allow adjustment of a size of the headgear assembly 1710.

For example, in the illustrated arrangement, three different strap spacer elements 1750a, 1750b, 1750c are provided and which can be interchanged within the hub 1760. In other configurations, a greater or lesser number of strap spacer elements 1750 can be provided. The strap spacer elements 1750a, 1750b, 1750c each comprise a suitable number of attachment locations for the given number of straps 1720, 1730, 1740. The attachment locations can be in the form of a recess 1770, which receives a connector end 1780 of the corresponding strap 1720, 1730, 1740. The recesses 1770 and the connector ends 1780 can have a retention arrangement configured to secure the connector end 1780 within the recess 1770. In the illustrated configuration, the retention arrangement is reversible and comprises attractive magnetic elements 1790 configured to attract one another with a magnetic force configured to secure the strap 1720, 1730, 1740 to the strap spacer element 1750a, 1750b, 1750c and hub 1760 against normal or expected forces, but that allows deliberate separation of the strap 1720, 1730, 1740 from the strap spacer element 1750a, 1750b, 1750c and hub 1760.

The recesses 1770 of the different strap spacer elements 1750a, 1750b, 1750c vary in depth such that a position of the straps 1720, 1730, 1740 relative to one another and to the hub 1760 is altered depending on which strap spacer element 1750a, 1750b, 1750c is selected. For example, the recesses 1770 of the small strap spacer element 1750a have the greatest depth to position the connector ends 1780 of the straps 1720, 1730, 1740 closest to one another and the recesses 1770 of the large strap spacer element 1750c have the shallowest depth to position the connector ends 1780 of the straps 1720, 1730, 1740 furthest from one another. The recesses 1770 of the medium strap spacer element 1750b have a depth between that of the small strap spacer element 1750a and the large strap spacer element 1750c.

In the illustrated configuration, the strap spacer elements 1750a, 1750b, 1750c are interchangeable within the hub 1760; however, different hubs 1760 could also be provided that include different strap spacer elements 1750a, 1750b, 1750c such that the entire hub 1760 is selected or interchanged instead of just the strap spacer element 1750a, 1750b, 1750c. In addition, a configuration in which a single strap spacer element 1750 includes multiple depth recesses 1770 (or another positioning arrangement) and can be adjusted to secure the strap 1720, 1730, 1740 in one of a number of different positions could also be used.

In some configurations, the headgear sizing adjustment mechanism includes the hub structure 1760 having a central aperture or space configured to receive one of a selected number of interchangeable inserts 1750. The headgear arrangement includes two or more divergent hub extending portions or arms that extend outwardly from the central aperture or space. The hub arms can be hollow such that a strap 1720, 1730, 1740 may pass through their length. The adjustment mechanism comprises one or more interchangeable inserts 1750 having a shape that fits within the aperture of the hub 1760 and a connection portion 1770 that aligns with each of the hub arms when assembled. Each of the connection portions 1770 can include a magnet 1790 that is configured to connect to a corresponding headgear strap 1720, 1730, 1740. The inserts 1750 can be provided in a range of different configurations such that the spacing between the connection portions 1770 is altered and thus the connection point with the headgear strap 1720, 1730, 1740 is moved. The headgear assembly 1710 can also include the plurality of straps 1720, 1730, 1740, which can be made of plastic and can be semi-rigid, such as intramolded straps. The straps 1720, 1730, 1740 can have magnets 1790 (for coupling with the magnets 1790 of the connection portions of the interchangeable insert 1750) located in at least one end. In some configurations, the headgear assembly 1710 provides an advantage that fewer components reduce manufacturing steps and cost. In addition, fewer components also reduce the time it takes to assemble and fit the headgear 1710 and mask M to a user U. The illustrated arrangement also simplifies the size adjustment of the headgear assembly 1710 by the user U needing only to switch the insert 1750.

Figures 44, 45, 46:
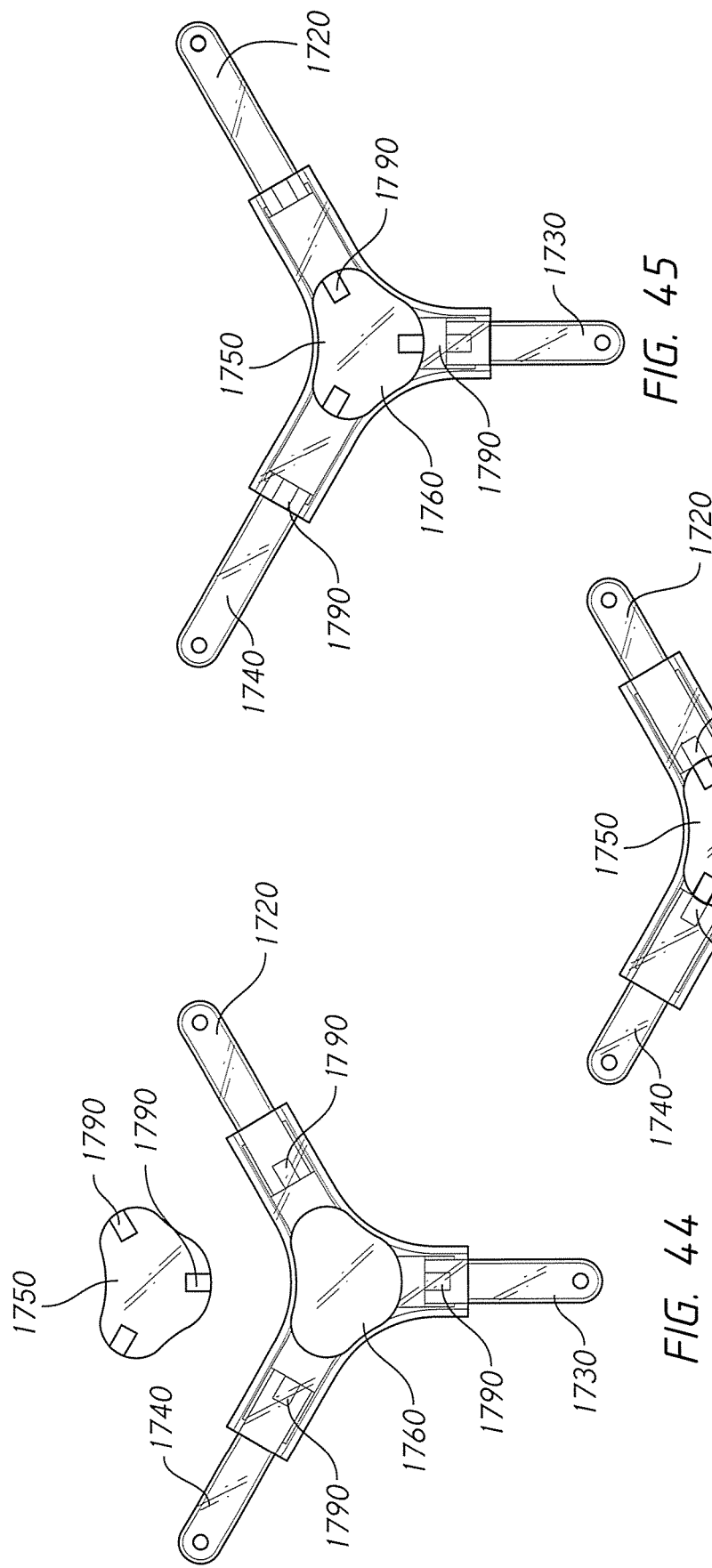
FIG. 44 illustrates the strap connector hub of FIGS. 41-43 with the insert disassembled from the hub.
FIG. 45 illustrates the strap connector hub of FIG. 44 with the insert assembled into the hub and the straps disengaged from the insert.
FIG. 46 illustrates the strap connector hub of FIG. 44 with the insert assembled into the hub and the straps engaged with the insert.

FIGS. 44-46 illustrate the connector hub 1760, strap spacer element or insert 1750 and straps 1720, 1730, 1740 in a disassembled state (FIG. 44), an assembled-disengaged state (FIG. 45) and an assembled—engaged state (FIG. 46). The disassembled state illustrates the insert 1750 removed from the hub 1760. However, the straps 1720, 1730, 1740 are assembled to the hub 1760. In some configurations, the straps 1720, 1730, 1740 are movable relative to the hub 1760, but are permanently assembled to the hub 1760. In the assembled-disengaged state, the insert 1750 is positioned within the hub 1760, but the straps 1720, 1730, 1740 are not engaged with the insert 1750. In the assembled-engaged state, the insert 1750 is positioned within the hub 1760 and the straps 1720, 1730, 1740 are engaged with the insert 1750.

FIGS. 47-49 illustrate a headgear assembly 1810 having a plurality of straps that are interconnected by a component, which allows for adjustment of a position of the strap relative to the component. In particular, the illustrated headgear assembly 1810 includes a top strap 1820, a rear strap 1830 and at least one front strap 1840. The headgear assembly 1810 holds a mask M in place on the head of a user U. The headgear assembly 1810 comprises a strap connector hub 1860 that interconnects two or more of the straps 1820, 1830, 1840 and allows for the position of the straps 1820, 1830, 1840 to be adjusted relative to the hub 1860.

In the illustrated arrangement, the hub 1860 is a two piece arrangement including, for example, a back 1862 and a front 1864 that can be selectively coupled to sandwich the strap(s) 1820, 1830, 1840 therebetween or separated to allow adjustment of the strap(s) 1820, 1830, 1840. The back 1862 and the front 1864 cooperate to form an interior space between them when coupled. The back 1862 and the front 1864 can be coupled in any suitable manner; however, in the illustrated arrangement the back 1862 includes a connector post 1866 configured to receive a fastener 1868 (or, possibly, a complementary connector post), such as a screw.

At least one of the back 1862 and the front 1864 include a plurality of adjustment pins 1870 for each strap 1820, 1830, 1840 and configured to engage corresponding adjustment holes 1880 of the strap 1820, 1830, 1840. The adjustment holes 1880 are spaced along a length of the strap 1820, 1830, 1840. The size of the headgear assembly 1810 can be adjusted by varying the number of adjustment holes 1880, within the straps 1820, 1830, 1840, that are engaged with the adjustment pins 1870 of the hub 1860. The more pins 1870 and holes 1880 that are engaged, the shorter the straps 1820, 1830, 1840 will be and smaller the headgear assembly 1810, and vice-versa. The back 1862 and front 1864 covers hide the connection between the hub 1760 and straps 1820, 1830, 1840.

FIGS. 50 and 51 illustrate a headgear assembly 1910 having at least one strap that is connected to a component in a manner that allows for adjustment of a position of the strap relative to the component. In particular, the illustrated headgear assembly 1910 includes a top strap 1920, a rear strap 1930 and at least one front strap 1940. The headgear assembly 1910 comprises a strap connector hub 1960 that interconnects two or more of the straps 1920, 1930, 1940 and allows for the position of at least one of the straps 1920, 1930, 1940 to be adjusted relative to the hub 1960. In the illustrated configuration, the top strap 1920 is adjustable relative to the hub 1960. In some configurations, the top strap 1920 is permanently connected to the hub 1960 once assembled. However, in other configurations, the connection between the top strap 1920 and the hub 1960 can be reversible and reusable.

In the illustrated configuration, the hub 1960 includes a plurality of spaced-apart sizing holes 1970a, 1970b, 1970c and the strap 1920 includes a push button, clip or protrusion 1980 that fits through and is retained by a selected one of the sizing holes 1970a, 1970b, 1970c. In use, the user selects which sizing hole 1970a, 1970b, 1970c to connect the push button 1980 to in order to select a length of the top strap 1920. Such an arrangement provides for an easy to operate method of size selection or adjustment of the headgear assembly 1910.

Figure 52:
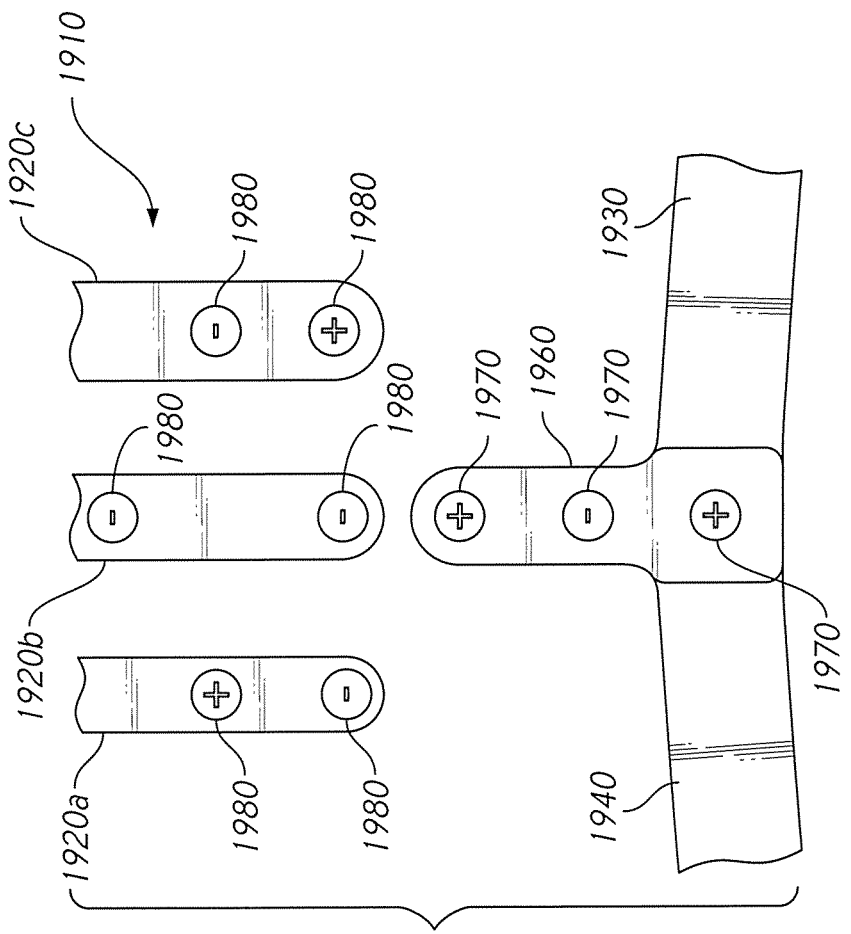
FIG. 52 is a side view of a portion of a headgear assembly that includes a strap connector hub on each side of the headgear assembly. The strap connector hub is configured to receive a strap of the headgear assembly in one of a plurality of possible positions utilizing a magnetic connection between the strap and the connector hub.

FIG. 52 illustrates a similar headgear assembly 1910 to the arrangement of FIGS. 50 and 51. Accordingly, the same reference numbers indicate corresponding or similar components or features. In the headgear assembly 1910 of FIG. 52, the hub 1960 is permanently assembled to the front strap 1940 and the rear strap 1930. The hub 1960 includes one or more embedded magnets 1970 that can be hidden from the outside of the hub 1960. The top strap 1920a, 1920b, 1920c can be provided in range of sizes or lengths and can have embedded magnets 1980 at the ends. The magnets 1980 in the selected top strap 1920a, 1920b, 1920c connects to a corresponding magnet 1970 in the hub 1960. The magnets 1970, 1980 can be arranged so that each size of strap 1920a, 1920b, 1920c can only be connected to the magnets 1970 in the hub 1960 in one position relative to the hub 1960. For example, the small strap 1920a connects to the lower two magnets 1970 of the hub 1960, the medium strap 1920b connects to the uppermost and lowermost magnets 1970 and the large strap 1920c connects to the upper two magnets 1970. Such an arrangement provides an easy to operate, slim and unobtrusive adjustable headgear assembly 1910.

FIGS. 53-55 illustrate a headgear assembly 2010 having at least one strap that is connected to a component in a manner that allows for adjustment of a position of the strap relative to the component. In particular, the illustrated headgear assembly 2010 includes a top strap 2020, a rear strap 2030 and at least one front strap 2040. The headgear assembly 2010 comprises a strap connector hub 2060 that interconnects two or more of the straps 2020, 2030, 2040 and allows for the position of at least one of the straps 2020, 2030, 2040 to be adjusted relative to the hub 2060. In the illustrated configuration, the top strap 2020 is adjustable relative to the hub 2060.

In the illustrated arrangement, the hub 2060 includes a protrusion or sizing post 2070 that is configured to engage a selected one of a plurality of sizing slots or holes 2080a, 2080b, 2080c formed in and spaced along the length of the top strap 2020 to allow a size of the headgear assembly 2010 to be adjusted. The top strap 2020 also includes an end portion 2090 that can be folded over to a side of the hub 2060 opposite the sizing post 2070 and can be secured to the hub 2060 by a suitable retention arrangement. In the illustrated configuration, the end portion 2090 of the top strap 2020 is secured to the hub 2060 by cooperating magnets 2092.

In some configurations, the rear strap 2030 and the front strap 2040 are permanently connected to the hub 2060. The straps 2030, 2040 could be over-molded, welded, sewn or otherwise attached to the hub 2060. In some configurations, the headgear assembly 2010 provides the advantage of fewer components required, which results in a simplified system. In addition, only one size of the strap 2020 and the hub 2060 is required to cover at least a portion of a particular user population.

Figure 57:
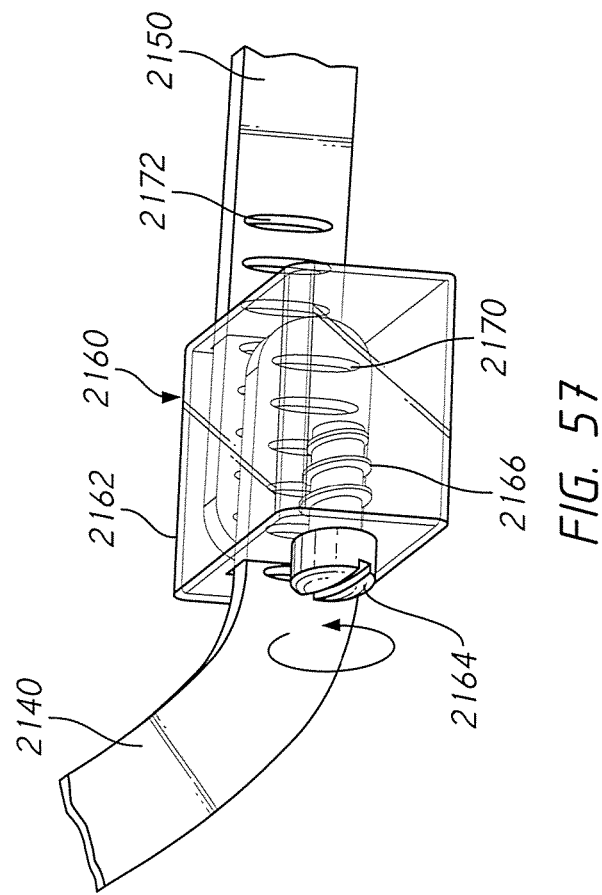
FIG. 57 is an enlarged view of an adjustment mechanism of the headgear of FIG. 56.
Figure 56:
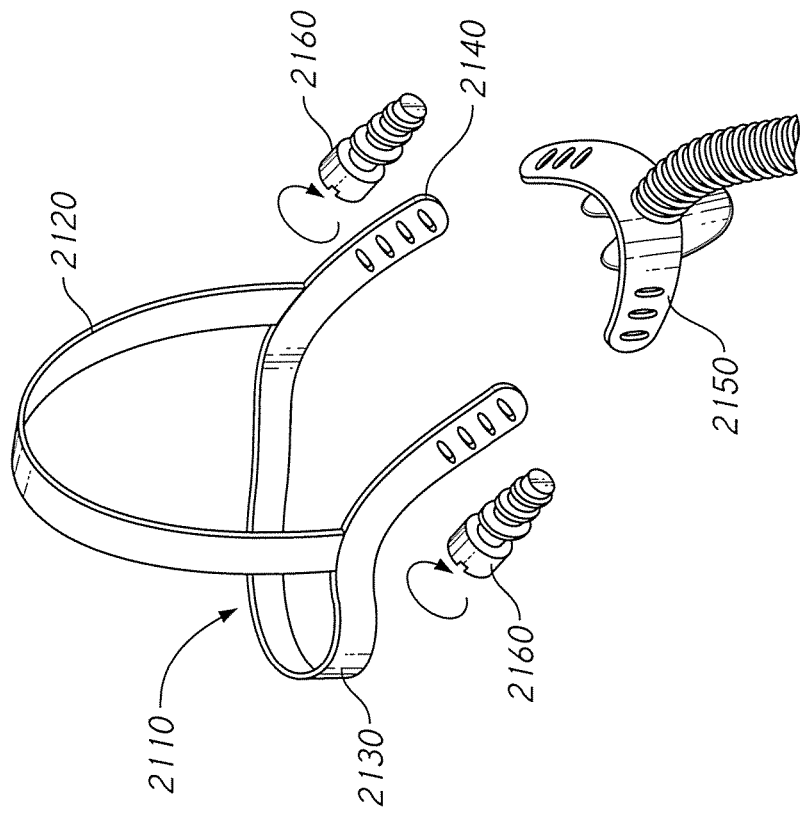
FIG. 56 is a perspective view of a headgear assembly including an adjustable connection between a rear portion of the headgear assembly and a mask frame portion.

FIGS. 56 and 57 illustrate a headgear assembly 2110 and mask M that are configured to allow for adjustment of a position of the headgear assembly 2110 relative to the mask M. In particular, the illustrated headgear assembly 2110 includes a top strap 2120, a rear strap 2130 and a front strap 2140 on each side of the headgear assembly 2110. The illustrated mask M includes a mask frame 2150 having rearwardly-extending side arms, each of which is configured to connect to the front strap 2140 of the headgear assembly 2110. The mask frame 2150 can be considered as a portion of the mask M or a portion of the headgear assembly 2110.

The illustrated headgear assembly 2110 comprises an adjustment mechanism 2160 associated with each front strap 2140 and each side arm of the mask frame 2150. Each adjustment mechanism 2160 comprises a housing 2162 that is configured to receive the front strap 2140 and the side arm of the mask frame 2150. In some configurations, each of the front strap 2140 and the side arm of the mask frame 2150 is movable relative to the housing 2162; however, in other arrangements only one of the front strap 2140 and the side arm of the mask frame 2150 is movable relative to the housing 2162. For example, the side arm of the mask frame 2150 can be fixed to the housing 2162.

The adjustment mechanism 2160 operates similar to a hose clamp mechanism and, in the illustrated arrangement, comprises a worm gear device in the form of a screw 2164 having a shaft with a helical thread 2166. The thread 2166 is configured to engage apertures or notches 2170 in the front strap 2140 such that rotation of the screw 2164 causes translation of the front strap 2140 relative to the housing 2162. With such an arrangement, the mask frame 2150 can be moved relative to the front strap 2140 to effectively adjust a length of the front strap 2140 and, therefore, a size of the headgear assembly 2110. Rotation of the screw 2164 in one direction moves the mask M closer to the headgear assembly 2110 and rotation of the screw 2164 in the opposite direction moves the mask M further from the headgear assembly 2110.

In some configurations, the side arm of the frame 2150 can alternatively or additionally include a plurality of apertures or notches 2172. The notches 2172 can be engaged by the screw 2164 (e.g., by a side of the screw 2164 opposite that which engages the front strap 2140) such that the side arm of the frame 2150 also translates relative to the housing 2162 in response to rotation of the screw 2164. In some configurations, a separate worm gear or screw can be provided to move the side arm of the frame 2150 relative to the housing 2162 such that the front strap 2140 and the frame 2150 can be separately adjusted relative to the housing. The illustrated adjustment mechanism 2160 advantageously also acts as a connector between the headgear assembly 2110 and the mask frame 2150. Such an arrangement can be set once then doesn't need to be adjusted again. In addition, the illustrated arrangement provides continuous adjustment to fit a wide range of users. In other configurations, the adjustment mechanism 2160 can be configured to allow length adjustment of two straps or two strap portions.

Figure 59:
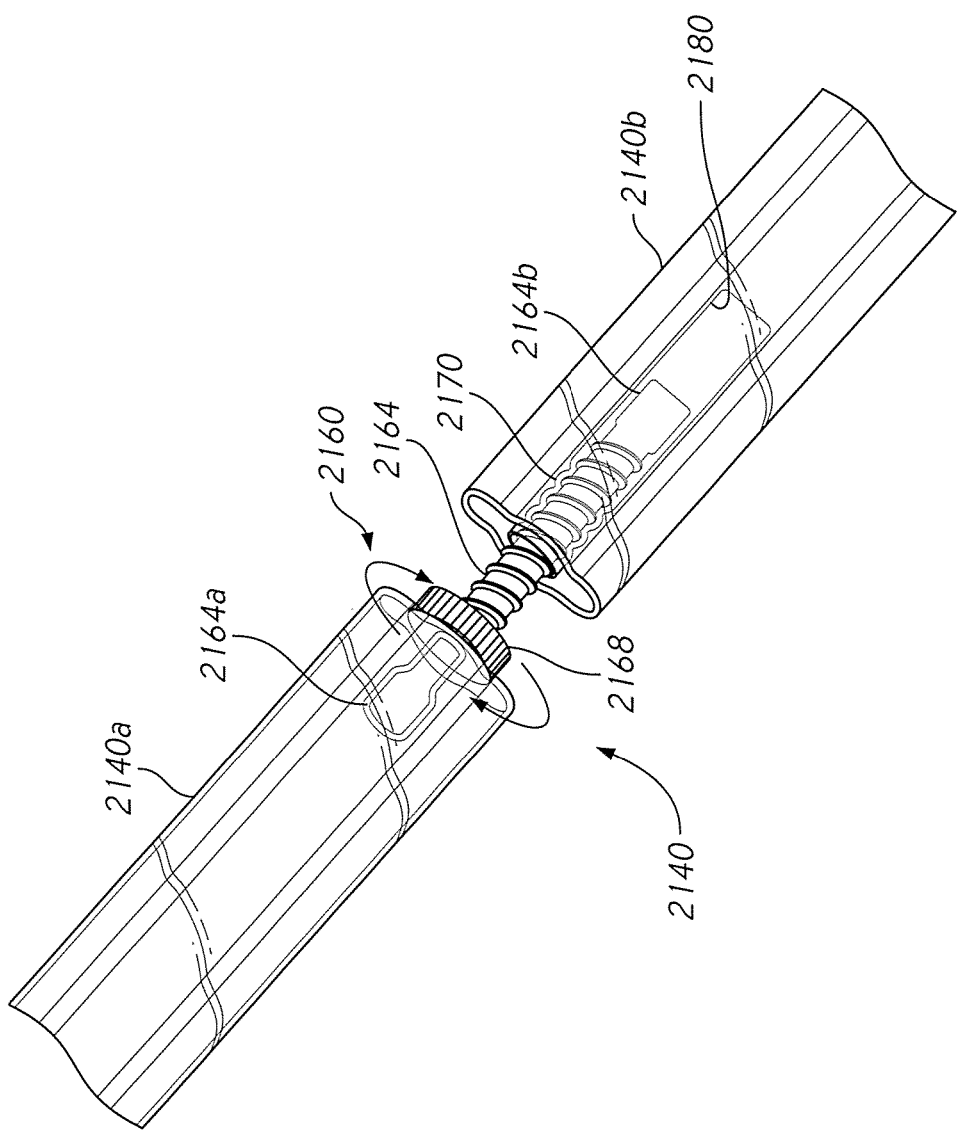
FIG. 59 is a perspective view of another threaded adjustment mechanism.

FIGS. 58 and 59 illustrate additional headgear assemblies 2110 having threaded adjustment arrangements 2160. Accordingly, the same reference numbers are used to refer to corresponding or similar components or features. The headgear assemblies 2110 of FIGS. 58 and 59 illustrate the threaded adjustment arrangements 2160 in between two strap portions 2140a, 2140b. However, the threaded adjustment arrangements 2160 could also be provided between two separate straps or between a strap and another component, such as a mask frame or a strap connector hub, for example.

With reference to FIG. 58, the threaded adjustment arrangement 2160 comprises a threaded member or threaded core 2164 carried by the first strap portion 2140a and engaging a threaded aperture 2170 of the second strap portion 2140b such that rotation of the threaded core 2164 moves the strap portions 2140a, 2140b toward or away from each other depending on the direction of rotation of the threaded core 2164. The threaded core 2164 extends through the first strap portion 2140a to an inset dial 2168, which is coupled to the threaded core 2164 and can be utilized by the user to rotate the threaded core 2164 to adjust an effective length of the strap 2140.

The threaded adjustment arrangement 2160 of FIG. 59 is substantially similar to the arrangement 2160 of FIG. 58 except the dial 2168 is located at an end of the first strap portion 2140a instead of being inset. In addition, FIG. 59 illustrates that the threaded element 2164 includes enlarged ends 2164a, 2164b that limit axial movement of the threaded element 2164 relative to the respective strap portions 2140a, 2140b. The enlarged end 2164a secures the threaded element 2164 in a fixed position relative to the strap portion 2140a. The enlarged end 2164b is located within an elongate passage 2180 defined within an interior of the second strap portion 2140b. The enlarged end 2164b allows limited axial movement of the threaded element 2164 between the ends of the passage 2180. Accordingly, the enlarged end 2164b can prevent separation of the threaded element 2164 and the second strap portion 2140b. The illustrated threaded adjustment mechanisms 2160 provide fine length adjustment of the strap 2140 or of the headgear assembly 2110.

FIG. 60 illustrates a headgear assembly 2210 and mask M that are configured to allow for adjustment of a position of the headgear assembly 2210 relative to the mask M. In particular, the illustrated headgear assembly 2210 includes a top strap 2220, a rear strap 2230 and a front strap 2240 on each side of the headgear assembly 2210. The illustrated mask M includes a mask frame 2250 that is connected to the front strap 2240 of the headgear assembly 2210. The mask frame 2250 can be considered as a portion of the mask M or a portion of the headgear assembly 2210.

The illustrated headgear assembly 2210 comprises an adjustment mechanism 2260 associated with each side of the headgear assembly 2210 and configured to allow a position of the front strap 2240 to be adjusted relative to a remainder of the headgear assembly 2210 (e.g., the top strap 2220 and/or rear strap 2230). In the illustrated configuration, a strap connection hub 2261 supports a ratchet mechanism 2262, which receives the front strap 2240. At least a portion of the front strap 2240 that engages the ratchet mechanism 2262 is in the form of a rack having a plurality of protrusions 2264 that can be engaged by a pawl of the ratchet mechanism 2262. As described herein, any one or more of the straps 2220, 2230, 2240 can be semi-rigid, such as intramolded. The ratchet mechanism 2262 can have a push button or levered release system configured to release the pawl from engagement with the protrusions 2264 of the front strap 2240.

FIGS. 61-65 illustrate a headgear assembly 2310 having at least one strap that is connected to a component in a manner that allows for adjustment of a position of the strap relative to the component. In particular, the illustrated headgear assembly 2310 includes a top strap 2320, a rear strap 2330 and at least one front strap 2340. The headgear assembly 2310 comprises a strap connector hub 2360 on each side that interconnects two or more of the straps 2320, 2330, 2340 and allows for the position of at least one of the straps 2320, 2330, 2340 to be adjusted relative to the hub 2360. In the illustrated configuration, the top strap 2320 is adjustable relative to the hubs 2360.

In the illustrated arrangement, each of the hubs 2360 includes an internal passage that receives the top strap 2320. The top strap 2320 can be slid through the passage of the hubs 2360 until a desired length of the top strap 2320 extending between the hubs 2360 is achieved. Each hub 2360 can include an arrangement for locking the top strap 2320 in the desired position relative to the hub 2360. An excess length 2320a of the top strap 2320 can be trimmed either manually or by a cutting or scoring mechanism built into the hub 2360. For example, the hub 2360 can have a push button 2362 (FIG. 62) or buttons (FIGS. 64 and 65) that actuate a lock mechanism to lock the top strap 2320 relative to the hub 2360. The lock mechanism can comprise teeth or serrations that engage the top strap 2320, for example.

FIGS. 66-68 illustrate a component 2412 of a headgear assembly 2410 that is configured to support a mask on the face of a user. The component 2412 can define any portion of the headgear assembly 2410 that influences a fit or size of the headgear assembly 2410. In the illustrated arrangement, the component 2412 is a side portion of the headgear assembly 2410 that defines at least portions of a top strap 2420, rear strap 2430 and a front strap 2440. The straps 2420, 2430, 2440 can be formed as a unitary structure, such as by intramolding. In some configurations, the component 2412 defines one half or substantially one half of the headgear assembly 2410. The length of one or more of the straps 2420, 2430, 2440 can be longer than necessary for some, most or all users and can be intended to be trimmed to size prior to use.

The component 2412 or components 2412 that make up the headgear assembly 2410 can be trimmed to size based on actual size measurements of the head of the intended user U. For example, with reference to FIG. 67, a scanner S can be used to measure the user's U head and determine a sizing parameter or parameters. The component(s) 2412 can then be trimmed at a particular location based on the sizing parameter(s), as illustrated in FIG. 68. The trimmed component 2412 can be coupled to another (trimmed or untrimmed) component 2412 or other portion of the headgear assembly 2410. The coupling can be done in any suitable manner, such as sewing, welding, or using a fastener, for example.

In some configurations, the component(s) 2412 are provided in a single size with the straps 2420, 2430, 2440 being longer than required. In some configurations, instead of 3D scanning the user's U head, a photo of the side of the head could be used to establish head dimensions for cutting, possibly along with an indicator of scale. In some configurations, the headgear assembly 2410 provides the advantages of fewer components and/or an individual fit for each user U. The component 2412 can include sizing marks to facilitate trimming and an algorithm can be utilized to determine and identify the locations for trimming. The sizing marks are not necessarily directly related to the measurements of the user U, but can be related by the algorithm.

FIGS. 69 and 70 illustrate a headgear assembly 2510 having two or more straps configured to be adjustable in orientation relative to one another. In particular, the headgear 2510 includes a top strap 2520, rear strap 2530 and a front strap 2540, two or more of which are adjustable in angle relative to one another. In the illustrated arrangement, an end of each of the straps 2520, 2530, 2540 is connected to a strap connection hub 2560 on each side of the headgear 2510. The hub 2560 includes a portion 2562, 2563, 2564 that is associated with a particular one of the straps 2520, 2530, 2540. In the illustrated configuration, the portions 2562, 2563, 2564 are in the form of discs that are rotatable relative to one another. In the illustrated arrangement, the discs 2562, 2563, 2564 are rotatably coupled at a central connection point 2570, such as by a fastener. Rotation of a disc 2562, 2563, 2564 relative to the other discs 2562, 2563, 2564 causes rotation of the strap 2520, 2530, 2540 associated with the particular disc 2562, 2563, 2564 relative to the other straps 2520, 2530, 2540. Accordingly, with such an arrangement, the orientation of or angles between the straps 2520, 2530, 2540 can be adjusted as desired by or for the user U. Once adjusted, the straps 2520, 2530, 2540 can be fixed in position by locking the relative position of the discs 2562, 2563, 2564, such as by using the fastener at the central connection point 2570.

In some configurations, the straps 2520, 2530, 2540 can be provided in a range of predetermined lengths for selection by or for the user U. As described herein, the straps 2520, 2530, 2540 can be intramolded. Each disc 2562, 2563, 2564 has a connection point 2580 for a strap 2520, 2530, 2540. The connection between the disc 2562, 2563, 2564 and the strap 2520, 2530, 2540 can be permanent or removable and can be of any suitable arrangement, such as a snap-fit connection, for example. In use, the straps 2520, 2530, 2540 can be selected to match the size of the user's U head and connected to the connection points 2580 of the hub 2560. The angle between each of the straps 2520, 2530, 2540 can be adjusted by rotating the discs 2562, 2563, 2564 of the hub 2560. Such an arrangement can provide a headgear assembly 2510 that is highly adjustable to each user's U head shape and/or size.

FIGS. 71 and 72 illustrate a headgear assembly 2510 that is similar to the headgear assembly 2510 of FIGS. 69 and 70. Accordingly, the same reference numerals are used to indicate corresponding or similar components or features. In the arrangement of FIGS. 71 and 72, each of the discs 2562, 2563, 2564 is integrated or unitarily formed with a respective one of the straps 2520, 2530, 2540. The hub 2560 is created when the straps 2520, 2530, 2540 are coupled to one another at the central connecting point 2570 of the discs 2562, 2563, 2564. Such an arrangement may allow the discs 2562, 2563, 2564 to be made thinner than those in which the separate straps 2520, 2530, 2540 need to be connected to the discs 2562, 2563, 2564. The thinner hub 2560 resulting from the thinner discs 2562, 2563, 2564 can be less obtrusive and more comfortable for the user. The discs 2562, 2563, 2564 can be joined by any suitable arrangement, such as magnetic or snap-fit connecting features or any other suitable fastener (e.g., one or more screws).

Figure 73:
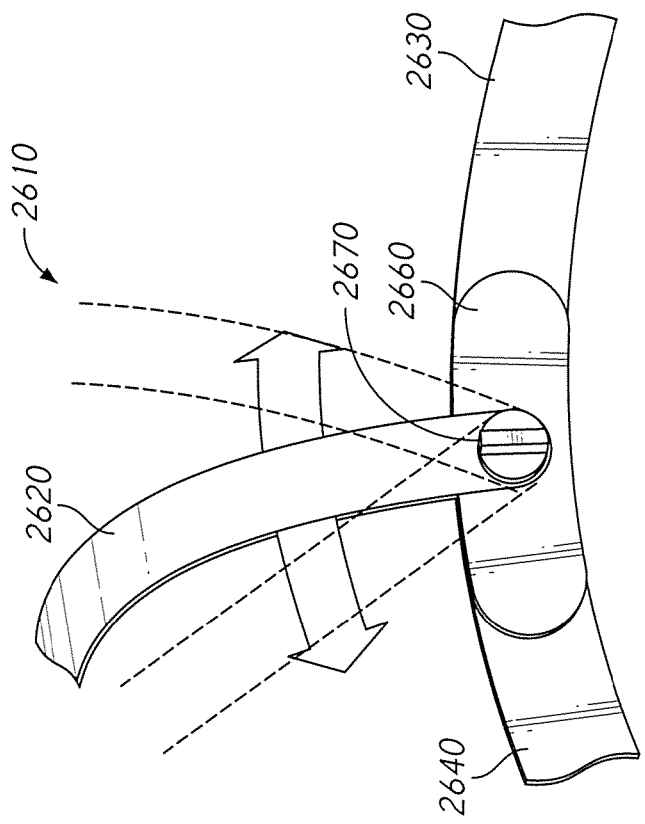
FIG. 73 is a side view of a portion of a headgear assembly having an angle adjustable top strap.
Figure 74:
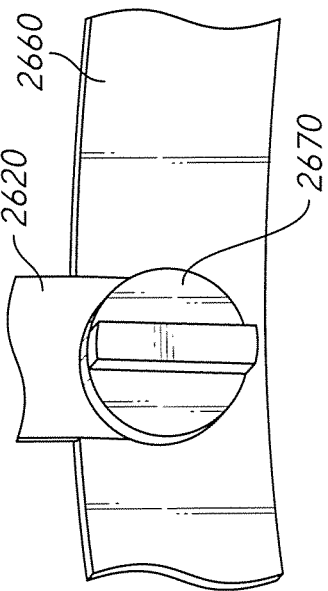
FIG. 74 is a side view of the angle adjuster of the headgear assembly of FIG. 73.

FIGS. 73 and 74 illustrate a headgear assembly 2610 having two or more straps configured to be adjustable in orientation relative to one another. In particular, the headgear 2610 includes a top strap 2620, rear strap 2630 and a front strap 2640, two or more of which are adjustable in angle relative to one another. In the illustrated arrangement, an end of the top strap 2620 is connected to the rear strap 2630 and/or front strap 2640 either directly or through a strap connection hub 2660 on each side of the headgear 2610. A knob 2670 can couple the top strap 2620 to the rear strap 2630, front strap 2640 or hub 2660. Rotation of the knob 2670 causes rotation of the top strap 2620 such that an angle or orientation of the top strap 2620 can be adjusted relative to the rear strap 2630, front strap 2640 or hub 2660. In some configurations, the knob 2670 includes an interlocking gear mechanism with the hub 2660. The knob 2670 can be pulled outwards away from the hub 2660 and turned to adjust the angle of the top strap 2620. The knob 2670 can be pushed inwards to lock the position of the top strap 2620. In some configurations, the top strap 2620 may be rotatable separately from the knob 2670 and the knob 2670 may simply operate to secure the top strap 2620 in a desired position once adjusted. In some configurations, two or more of the rear strap 2630, front strap 2640 and hub 2660 are formed as an integrated or unitary structure.

Figure 75:
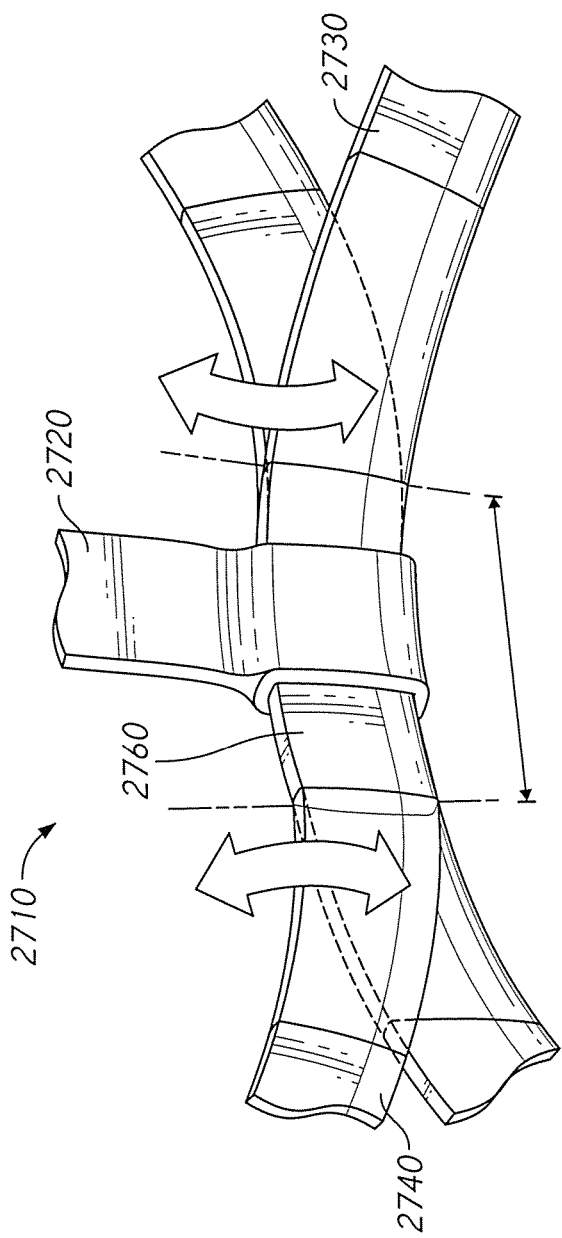
FIG. 75 is a side view of a portion of a headgear assembly having a strap connector hub and at least one strap that is configured to be coupled to the hub in at least two orientations.
Figure 77:
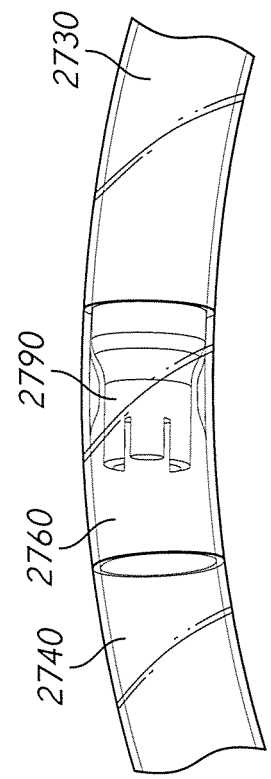
FIG. 77 illustrates a second type of connection between the hub and the strap in the headgear assembly of FIG. 75.
Figure 76:
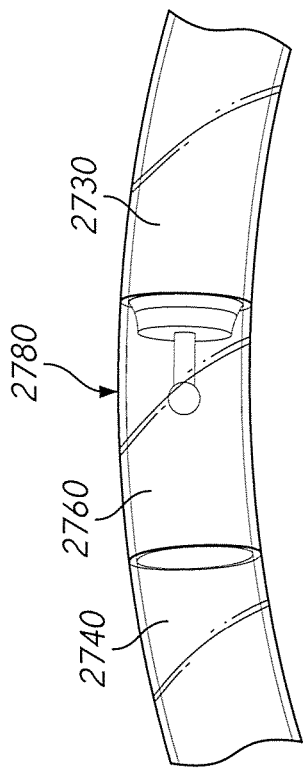
FIG. 76 illustrates a first type of connection between the hub and the strap in the headgear assembly of FIG. 75.

FIGS. 75-77 illustrate a headgear assembly 2710 having two or more straps that can be altered in orientation relative to one another. In particular, the headgear 2710 includes a top strap 2720, rear strap 2730 and a front strap 2740, two or more of which are adjustable in orientation relative to one another. In the illustrated arrangement, an end of the top strap 2720 is connected to the rear strap 2730 and the front strap 2740 through a strap connection hub 2760 on each side of the headgear 2710. The rear strap 2730 and/or the front strap 2740 have a non-linear shape relative to a longitudinal axis of the hub 2760. In the illustrated arrangement, the rear strap 2730 and the front strap 2740 are curved; however, in other configurations, the rear strap 2730 and the front strap 2740 can be straight, but oriented at an angle relative to a longitudinal axis of the hub 2760. The rear strap 2730 and/or the front strap 2740 can be connected to or oriented relative to the hub 2760 in one of at least two relative orientations, as illustrated in FIG. 75.

In some configurations, the rear strap 2730 and/or the front strap 2740 can be coupled to the hub 2760 by a swivel connector that permits rotational movement of the rear strap 2730 or the front strap 2740 relative to a longitudinal axis of the hub 2760. Any suitable type of connector can be used, such as a snap-fit connector, for example. With reference to FIG. 76, the rear strap 2730 and/or the front strap 2740 can be connected to the hub 2760 by a ball joint connector 2780, in which the strap 2730, 2740 includes a male connector portion and the hub 2760 includes a female connector portion, or vice-versa. With reference to FIG. 77, the rear strap 2730 and/or the front strap 2740 can be connected to the hub 2760 by a cylindrical swivel clip connector 2790, in which the strap 2730, 2740 includes a male connector portion and the hub 2760 includes a female connector portion, or vice-versa. While only one connector 2780, 2790 is illustrated in FIGS. 76 and 77, each strap 2730, 2740 that is adjustably connected to the hub 2760 can include a suitable connector 2780, 2790. As described herein, one or more of the straps 2720, 2730, 2740 can be intramolded. Such an arrangement allows for the simple and convenient adjustment of an orientation or angle of the top strap 2720 relative to the front strap 2740 and/or the rear strap 2730.

FIGS. 78 and 79 illustrate headgear assemblies 2810 comprising a plurality of spacer elements or chain links 2850 that can be stacked together in a selected quantity to result in a desired length of a headgear strap or a desired size of the headgear 2810. The strap can be a top strap 2820, a rear strap 2830, a front strap 2840 or another strap or portion of the headgear 2810. In the illustrated arrangement, the strap 2820, 2830, 2840 comprises a connection member or arrangement to connect a desired number of the spacer elements 2850. In the illustrated arrangement, the connection member or arrangement is in the form of an outer sheath, sock or sleeve 2860 that is configured to accept a plurality of spacer elements 2850. In some configuration, the connection member is a fabric sock or sleeve. The spacer elements 2850 can be provided in different sizes (e.g., lengths), such as a short spacer element 2850a or a medium spacer element 2850b. Other sizes can also be provided. A user U can select a particular number of a particular size or sizes of spacer elements 2850 to create a strap 2820, 2830, 2840, or portion thereof, of a desired length. In some configurations, the spacers 2850 can be configured to be coupled together, such as by a snap-fit connection. Each spacer 2850 can include a male snap-fit connector portion 2860 and a female snap-fit connector portion 2870 such that the spacers 2850 can be stacked and secured to one another, as illustrated in FIG. 79. The snap-fit connection can act as the connection member or arrangement or can be used in addition to a sheath, sock or sleeve 2860.

FIGS. 80-82 illustrate a number of strap connection arrangements 2912 configured to connect two straps or strap portions of a headgear assembly. The strap connection arrangements 2912 can be configured to connect a strap to another component or any two components of a headgear assembly. In the illustrated arrangement, the strap connection arrangements 2912 are illustrated in the context of connecting a pair of straps 2914, 2916; however, the arrangements 2912 can be applied to other components, as well. FIG. 80 illustrates a twist lock arrangement in which one strap 2914 includes a protrusion 2970 that is received within a curved slot 2980 of the other strap 2916. The strap 2914 can be rotated to move the protrusion 2970 to the end of the slot 2980 and lock the straps 2914, 2916 together.

In the arrangement 2912 of FIG. 81, the strap 2916 includes a keyhole shaped slot 2980 having an enlarged end configured to receive the protrusion 2970 of the strap 2914. The end of the strap 2916 can be configured to flex to allow the protrusion 2970 to be passed through the narrower entrance of the slot 2980 and into the enlarged end of the slot 2980.

In the arrangement 2912 of FIG. 82, the strap 2914 includes a hook end 2970 that engages a hook end 2980 of the strap 2916. The hook ends 2970, 2980 can be engaged by a push fit motion in which the hook ends 2980 can be pushed past one another and allowed to return to engage one another.

Figure 85:
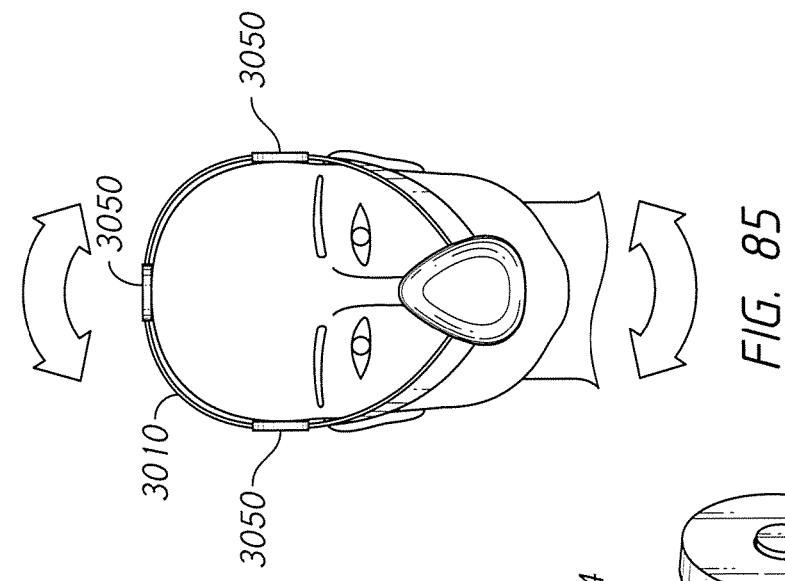
FIG. 85 is a front view of the user and headgear assembly of FIG. 85.
Figure 84:
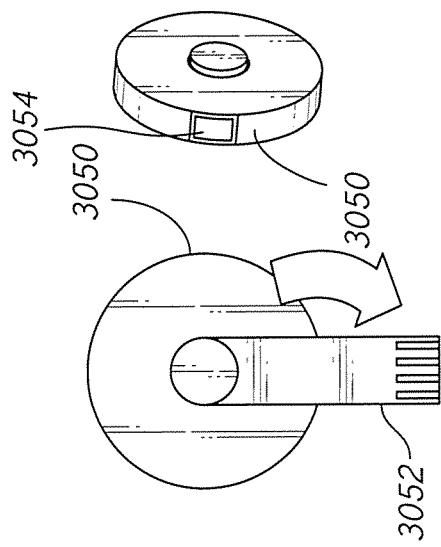
FIG. 84 illustrates the smart connection hub separately from the headgear straps.
Figure 83:
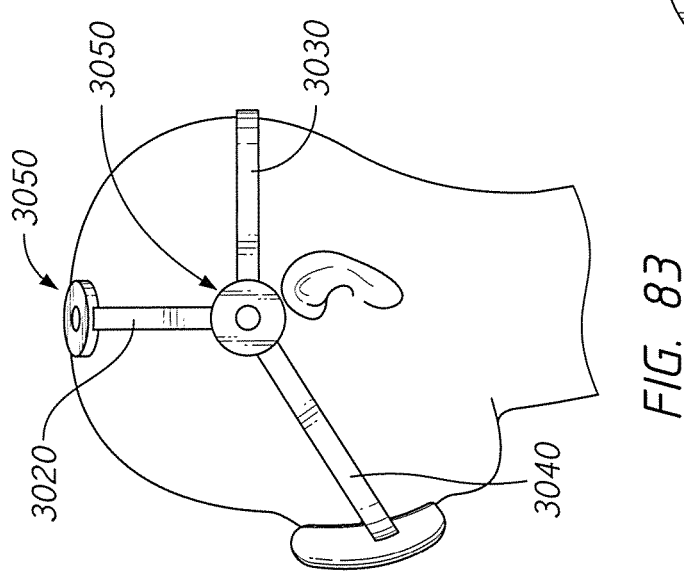
FIG. 83 is a side view of a headgear assembly having one or more smart connection hubs configured to connect straps of the headgear assembly and track user movement.

FIGS. 83-85 illustrate a headgear assembly 3010 configured to hold a mask M on the head of a user U and incorporating one or more smart hubs 3050 configured to detect and store information regarding movement of the user U or other physiological parameters that can be used to measure compliance or efficacy of therapy. In some configurations, the smart hubs 3050, directly or in combination with another system, can utilize information from the blower unit 3 (e.g., CPAP, FIG. 1) to detect a position of the user U when a leak occurs. This information can be utilized to address the leaks. In some configurations, the smart hubs 3050 can connect together straps or strap portions of the headgear 3010. For example, the headgear 3010 can comprise a top strap 3020, a rear strap 3030 and at least one front strap 3040. In the illustrated arrangement, the headgear assembly 3010 includes a smart hub 3050 on each side of the headgear assembly 3010 positioned above the user's U ear. Each of the side smart hubs 3050 connects the top strap 3020, the rear strap 3030 and one of the front straps 3040. In addition, a smart hub 3050 is located within the top strap 3020 on the top of the user's U head. The connection between the smart hubs 3050 and the straps 3020, 3030, 3040 can be permanent or removable and can be of any suitable arrangement, such as any of those described herein.

With reference to FIG. 84, one or more of the smart hubs 3050 can include a memory, which can be accessed by one or more ports, such as one or both of a male USB port 3052 and a female USB port 3054. In some configurations, the smart hubs 3050 can be configured for wireless communication with computers or other devices by any suitable protocol, such as Bluetooth, for example. In some configurations, the smart hubs 3050 can detect and/or hold data and information about the patient and can also track signals and movement. For example, the smart hubs 3050 can include a gyroscope and accelerometer and can be programmed to track movements and sleeping positions.

Figure 86:
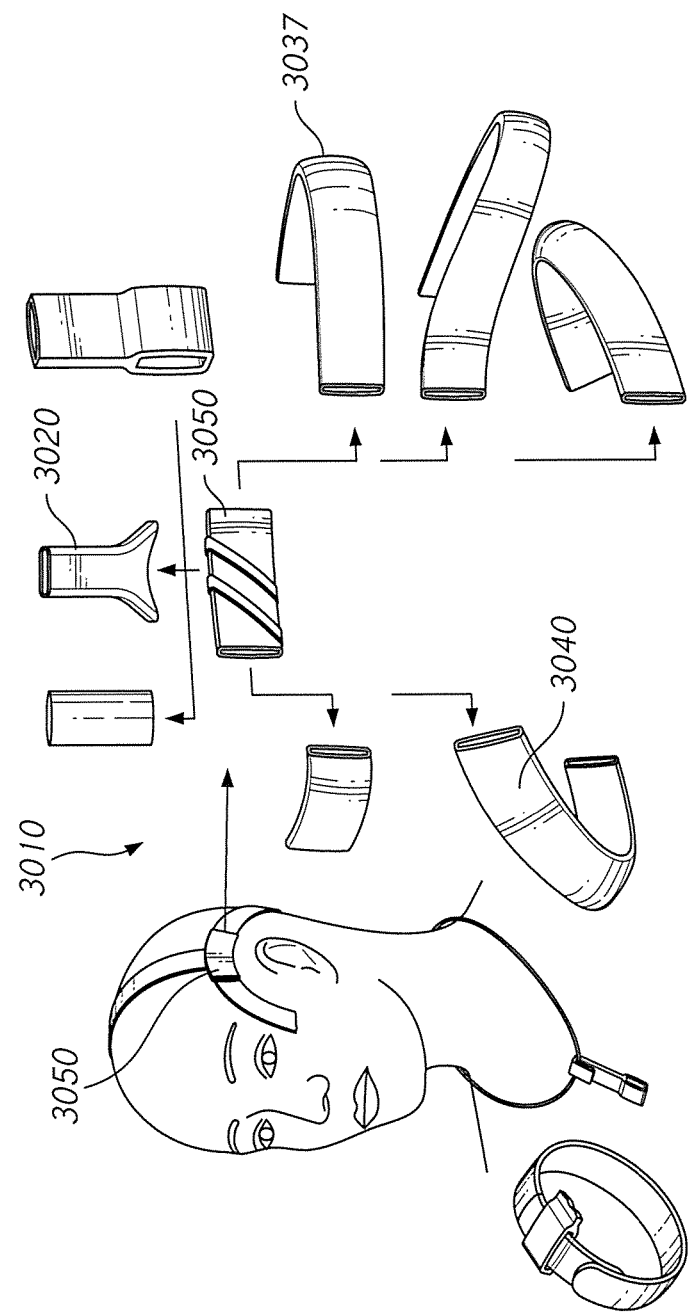
FIG. 86 illustrates another headgear assembly having a smart connection hub that connects straps of the headgear assembly.
Figure 87:
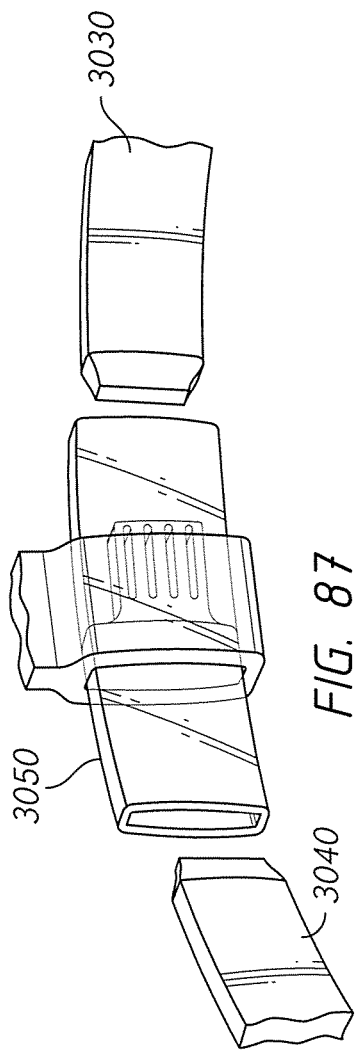
FIG. 87 is an enlarged view of the smart connection hub and a connection with the straps.

FIGS. 86 and 87 illustrate a headgear assembly 3010 that is similar to the headgear assembly 3010 of FIGS. 83-85. Accordingly, the same reference numerals are used to indicate corresponding or similar components or features. In the configuration of FIGS. 86 and 87, the smart hub 3050 or smart hubs 3050 in the headgear assembly 3010 can be individualized to fit an individual user's U head shape, such as by custom forming or 3D printing, for example. Other features, such as color, material, finish, etc. can be individualized. The individualized smart hubs 3050 can be configured to store information relating to the user U and his or her treatment for use in monitoring treatment. The user U can utilize the smart hub 3050 with different, in some cases replaceable, headgear components. For example, the user U can retain the smart hub 3050 when one or more of the other straps 3020, 3030, 3040 are replaced. The smart hub 3050 can also be used without the headgear, such as worn as a necklace or bracelet to track movement or for other uses. For example, the user U may wish to transmit information to a caregiver (e.g., during a doctor's appointment) by physically transporting the smart hub 3050 to the doctor's office. Allowing incorporation of the smart hub 3050 into an item other than the headgear, including wearable items such as a necklace or bracelet, makes the smart hub 3050 more portable than a headgear assembly while also reducing the likelihood of being lost. FIG. 86 illustrates different top strap 3020, rear strap 3030 or front straps 3040 that can be coupled to the smart hub 3050. FIG. 87 illustrates that the straps 3030, 3040 can be removable from the smart hub 3050.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to." Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Language of degree used herein, such as the terms "approximately," "about," "generally," and "substantially," as used herein represent a value, amount or characteristic close to the stated value, amount or characteristic that still performs a desired function or achieves a desired result. The deviation from the stated value, amount or characteristic could, for example, reflect acceptable tolerances, conversion factors, rounding off, measurement error, or other factors known to those of skill in the art. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A headgear assembly comprising:
    an interchangeable hub that is substantially rigid;
    a plurality of inelastic straps comprising a first top strap, a second top strap, a first rear strap, and a second rear strap and at least one front strap;
    wherein the interchangeable hub comprises a first connection point for the first or second top strap, a second connection point for the first or second rear strap, and a third connection point for the at least one front strap, the interchangeable hub configured to define an angle of each pair of the plurality of inelastic straps relative to one another, wherein the interchangeable hub is configured to determine a size of the headgear assembly by a spacing of the straps relative to one another;
    wherein the plurality of inelastic straps are provided in a range of strap sizes; and
    wherein the first top strap or the second top strap is configured to extend over a top of a head of a user and vertically upward from an ear of the user when in use by the user who is sitting upright,
    wherein the plurality of inelastic straps provided in the range of sizes have the same shape and are configured to be used interchangeably as the top strap, the rear strap or the front strap when assembled; wherein the first top strap and first rear strap are configured to fasten to the interchangeable hub for a first user of a first head size,
    the second top strap and second rear strap are configured to fasten to the interchangeable hub for a second user of a second head size, wherein a length of the first top strap is different from a length of the second top strap, and a length of the first rear strap is different from a length of the second rear strap.

2. The headgear assembly of claim 1, further comprising a plurality of interchangeable hubs provided in a range of hub sizes, each of the interchangeable hubs comprising a first connection point for the top strap, a second connection point for the rear strap, and a third connection point for the at least one front strap.

3. The headgear assembly of claim 1, further comprising a push fit connection between the interchangeable hub and each of the plurality of inelastic straps.

4. The headgear assembly of claim 1, wherein one or both of the interchangeable hub and at least one of the plurality of inelastic straps are injection-molded inside a fabric sleeve.

5. The headgear assembly of claim 1, wherein the first and second top straps comprises a first top strap connector element and the first and second rear straps comprises a first rear strap connector element, the first top strap connector element configured to connect to the interchangeable hub and the first rear strap connector element configured to connect to the interchangeable hub.

6. The headgear assembly of claim 5, wherein the first top strap connector element is configured to connect to the first connection point of the interchangeable hub and the first rear strap connector element is configured to connect to the second connection point of the interchangeable hub.

7. The headgear assembly of claim 5, wherein the first and second top straps comprises a second top strap connector element, the first top strap connector element and the second top strap connector element being the same.

8. The headgear assembly of claim 5, wherein the first and second top straps comprises a second top strap connector element, the first top strap connector element and the second top strap connector element being different from each other.

9. The headgear assembly of claim 5, wherein the first and second rear straps comprises a second rear strap connector element, the first rear strap connector element and the second rear strap connector element being the same.

10. The headgear assembly of claim 5, wherein the first and second rear straps comprises a second rear strap connector element, the first rear strap connector element and the second rear strap connector element being different from each other.

11. The headgear assembly of claim 5, wherein the first top strap connector element and the first rear strap connector element are interchangeable.

12. The headgear assembly of claim 5, wherein the first top strap connector element and the first rear strap connector element are not interchangeable.

13. The headgear assembly of claim 5, wherein the first top strap connector element is configured to connect to the first connection point for the top strap but not the second connection point for the rear strap.

14. The headgear assembly of claim 5, wherein the first rear strap connector element is configured to connect to the second connection point for the rear strap but not the first connection point for the top strap.

* * * * *

UNITED STATES PATENT AND TRADEMARK OFFICE
CERTIFICATE OF CORRECTION

PATENT NO. : 11,844,903 B2
APPLICATION NO. : 15/746240
DATED : December 19, 2023
INVENTOR(S) : Paul Mathew Freestone et al.

It is certified that error appears in the above-identified patent and that said Letters Patent is hereby corrected as shown below:

On the Title Page

Column 1 (Inventors), Line 9, delete "(AU);" and insert -- (NZ); --.

In the Specification

Column 19, Line 48, delete "(FIGS." and insert -- (FIG. --.

Column 37, Line 37, delete "that that" and insert -- that --.

In the Claims

Column 38, Line 47, Claim 5, delete "comprises" and insert -- comprise --.

Column 38, Line 48, Claim 5, delete "comprises" and insert -- comprise --.

Column 38, Line 59, Claim 7, delete "comprises" and insert -- comprise --.

Column 38, Line 63, Claim 8, delete "comprises" and insert -- comprise --.

Column 38, Line 67, Claim 9, delete "comprises" and insert -- comprise --.

Column 39, Line 4, Claim 10, delete "comprises" and insert -- comprise --.

Signed and Sealed this
Twentieth Day of February, 2024

Katherine Kelly Vidal
*Director of the United States Patent and Trademark Office*